US010479825B2

(12) United States Patent
Crowe et al.

(10) Patent No.: US 10,479,825 B2
(45) Date of Patent: Nov. 19, 2019

(54) ANTIBODY-MEDIATED NEUTRALIZATION OF MARBURG VIRUS

(71) Applicants: VANDERBILT UNIVERSITY, Nashville, TN (US); THE BOARD OF REGENTS OF THE UNIVERSITY OF TEXAS SYSTEM, Austin, TX (US)

(72) Inventors: James E. Crowe, Nashville, TN (US); Andrew I. Flyak, Nashville, TN (US); Alexander Bukreyev, Galveston, TX (US); Philipp Ilinykh, Galveston, TX (US)

(73) Assignees: VANDERBILT UNIVERSITY, Nashville, TN (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/553,311

(22) PCT Filed: Feb. 25, 2016

(86) PCT No.: PCT/US2016/019644

§ 371 (c)(1),
(2) Date: Aug. 24, 2017

(87) PCT Pub. No.: WO2016/138312

PCT Pub. Date: Sep. 1, 2016

(65) Prior Publication Data

US 2018/0312574 A1 Nov. 1, 2018

Related U.S. Application Data

(60) Provisional application No. 62/120,657, filed on Feb. 25, 2015.

(51) Int. Cl.

| | |
|---|---|
| ***C07K 16/10*** | (2006.01) |
| ***A61P 31/14*** | (2006.01) |
| ***C12Q 1/70*** | (2006.01) |
| ***C07K 16/46*** | (2006.01) |
| *A61K 39/00* | (2006.01) |

(52) U.S. Cl.

CPC .............. *C07K 16/10* (2013.01); *A61P 31/14* (2018.01); *C07K 16/468* (2013.01); *C12Q 1/701* (2013.01); *A61K 2039/505* (2013.01); *C07K 2317/21* (2013.01); *C07K 2317/31* (2013.01); *C07K 2317/33* (2013.01); *C07K 2317/34* (2013.01); *C07K 2317/55* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 2006/0269977 A1 | 11/2006 | Sawadaishi et al. |
| 2007/0042383 A1 | 2/2007 | Kapur et al. |
| 2008/0095775 A1 | 4/2008 | Lewis et al. |
| 2011/0296543 A1 | 12/2011 | Chang et al. |
| 2012/0156239 A1 | 6/2012 | Sullivan et al. |

FOREIGN PATENT DOCUMENTS

| | | |
|---|---|---|
| WO | WO 2006/120230 | 11/2006 |
| WO | WO 2015/123777 | 8/2015 |

OTHER PUBLICATIONS

Flyak et al., Mechanism of Human Antibody-Mediated Neutralization of Marburg Virus, 2015, Cell, vol. 160, No. 5, pp. 893-903.*

DiNapoli et al., Respiratory tract immunization of non-human primates with a Newcastle disease virus-vectored vaccine candidate against Ebola virus elicits a neutralizing antibody response, 2011, Vaccine, vol. 29, pp. 17-25.*

"A0A059LH78_9CHLO", UniProtKB/TrEMBL Accession No. A0A059LH78, dated Oct. 19, 2014.

Cook and Lee. "The secret life of viral entry glycoproteins: moonlighting in immune evasion." *PLoS pathogens* 9.5 (2013): e1003258.

Dias, João M., et al. "A shared structural solution for neutralizing ebolaviruses." *Nature structural and molecular biology* 18.12 (2011): 1424.

Dye, John M., et at "Postexposure antibody prophylaxis protects nonhuman primates from filovirus disease." *Proceedings of the National Academy of Sciences* 109.13 (2012): 5034-5039.

Extended European Search Report issued in European Application No. 16756393.1, dated Oct. 12, 2018.

Flyak et al., "Mechanisms of Antibody Neutralization of Marburg Virus in a Survivor of Natural Infection", poster presented at the $6^{th}$ International Symposium on Filoviruses, Galveston, Texas, 2014.

Flyak, Andrew I., et al. "Mechanism of human antibody-mediated neutralization of Marburg virus." *Cell* 160.5 (2015): 893-903.

Fusco, Marnie L., et al. "Protective mAbs and cross-reactive mAbs raised by immunization with engineered Marburg virus GPs." *PLoS pathogens* 11.6 (2015): e1005016.

Hashiguchi, Takao, et al. "Structural basis for Marburg virus neutralization by a cross-reactive human antibody." *Cell* 160.5 (2015): 904-912.

Hevey, Michael, Diane Negley, and Alan Schmaljohn. "Characterization of monoclonal antibodies to Marburg virus (strain Musoke) glycoprotein and identification of two protective epitopes." *Virology* 314.1 (2003): 350-357.

International Preliminary Report on Patentability issued in International Application PCT/US16/19644, dated Sep. 8, 2017.

International Search Report and Written Opinion issued in International Application No. PCT/US16/19644, dated Aug. 5, 2016.

Invitation to Pay Additional Fees issued in International Application No. PCT/US16/19644, dated May 23, 2016.

Kajihara, Masahiro, et al. "Inhibition of Marburg virus budding by nonneutralizing antibodies to the envelope glycoprotein." *Journal of virology* (2012): JVI-01896.

(Continued)

*Primary Examiner* — Benjamin P Blumel

(74) *Attorney, Agent, or Firm* — Parker Highlander PLLC

(57) ABSTRACT

The present disclosure is directed to antibodies binding to *Marburg* virus (MARV) glycoprotein (GP) and methods of use therefore.

24 Claims, 22 Drawing Sheets

Specification includes a Sequence Listing.

(56) References Cited

OTHER PUBLICATIONS

Kajihara, Masahiro, et al. "Novel mutations in Marburg virus glycoprotein associated with viral evasion from antibody mediated immune pressure," *Journal of General Virology* 94.4 (2013): 876-883.
Lee, Jeffrey E., et al. "Structure of the Ebola virus glycoprotein bound to an antibody from a human survivor." *Nature*454.7201 (2008): 177.
Marceau, Caleb D., et al. "Novel neutralizing monoclonal antibodies protect rodents against lethal filovirus challenges." *Trials in Vaccinology* 3 (2014): 89-94.
Maruyama, Toshiaki, et al. "Ebola virus can be effectively neutralized by antibody produced in natural human infection." *Journal of virology* 73.7 (1999): 6024-6030.
Marzi, Andrea, et al. "Protective efficacy of neutralizing monoclonal antibodies in a nonhuman primate model of Ebola hemorrhagic fever." *PloS one* 7.4 (2012): e36192.
Mucin, Charles D., et al. "Structures of protective antibodies reveal sites of vulnerability on Ebola virus." *Proceedings of the National Academy of Sciences* 111.48 (2014): 17182-17187.
Nakayama, Eri, et al. "Antibody-dependent enhancement of Marburg virus infection," *The Journal of infectious diseases*204.suppl_3 (2011): S978-S985.
Olinger; Gene Garrard, et al. "Delayed treatment of Ebola virus infection with plant-derived monoclonal antibodies provides protection in rhesus macaques." *Proceedings of the National Academy of Sciences* 109.44 (2012): 18030-18035.
Partial Supplementary European Search issued in European Application No. 16756393.1, dated Jun. 26, 2018.
Pettitt, James, et al. "Therapeutic intervention of Ebola virus infection in rhesus macaques with the MB-003 monoclonal antibody cocktail." *Science translational medicine* 5.199 (2013): 199ra113-199ra113.
Qiu, Xiangguo, et al. "Reversion of advanced Ebola virus disease in nonhuman primates with ZMapp." *Nature* 514.7520 (2014): 47.
Qiu, Xiangguo, et al. "Successful treatment of Ebola virus—infected cynomolgus macaques with monoclonal antibodies." *Science translational medicine* 4.138 (2012): 138ra81-138ra81.
Saphire, Erica Ollmann "An update on the use of antibodies against the filoviruses." *Immunotherapy*5.11 (2013): 1221-1233.

* cited by examiner

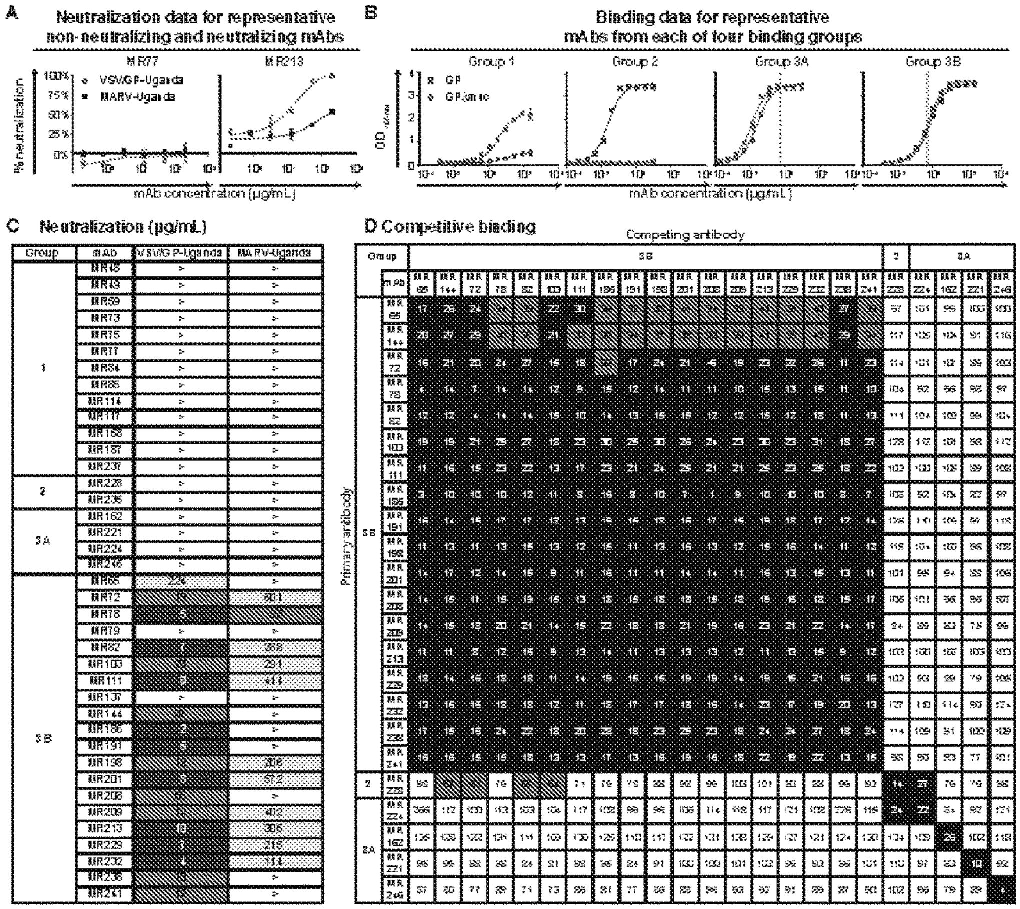
FIGS. 1A-D

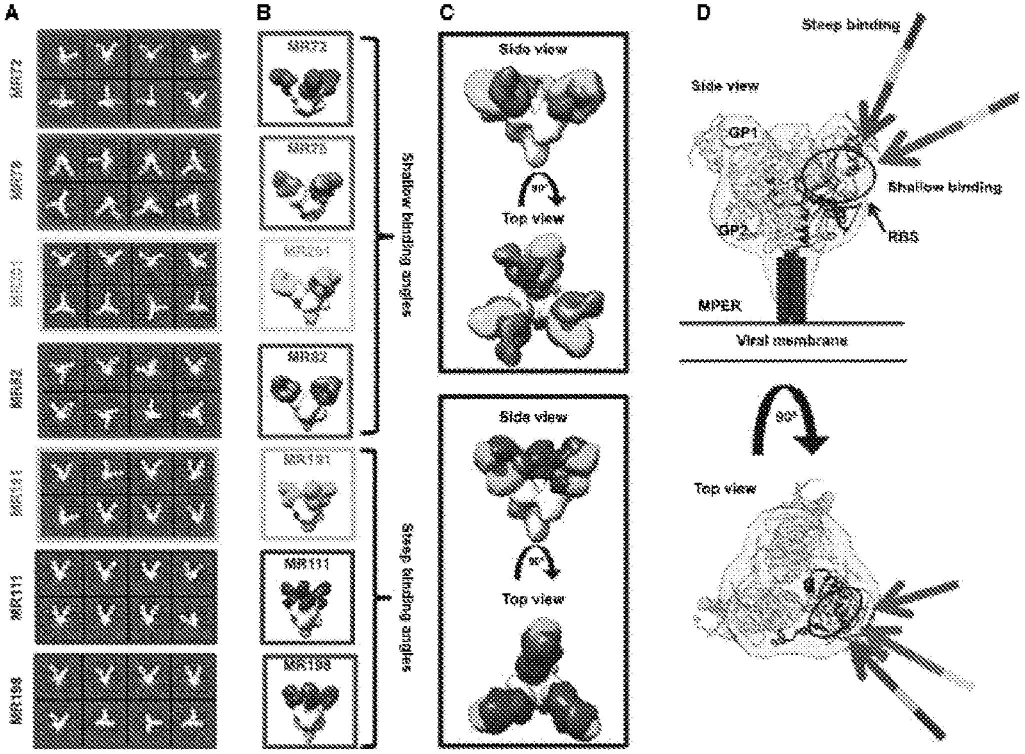
FIGS. 2A-D

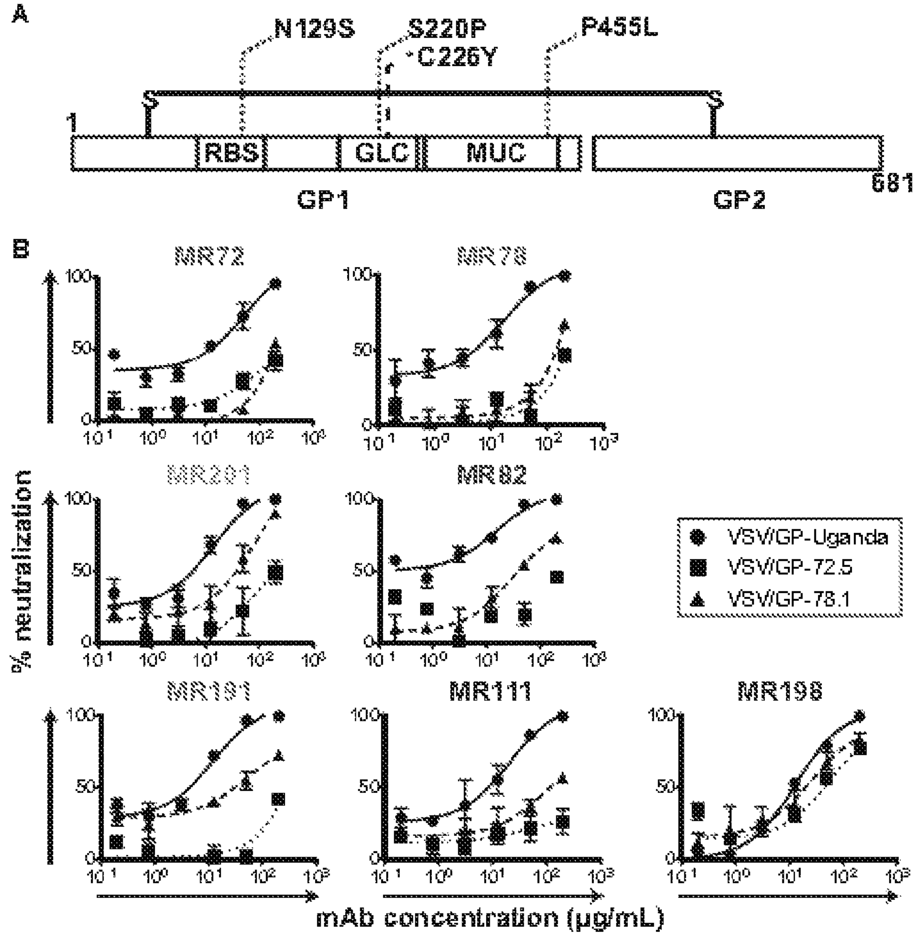
FIGS. 3A-B

Figure 4A:
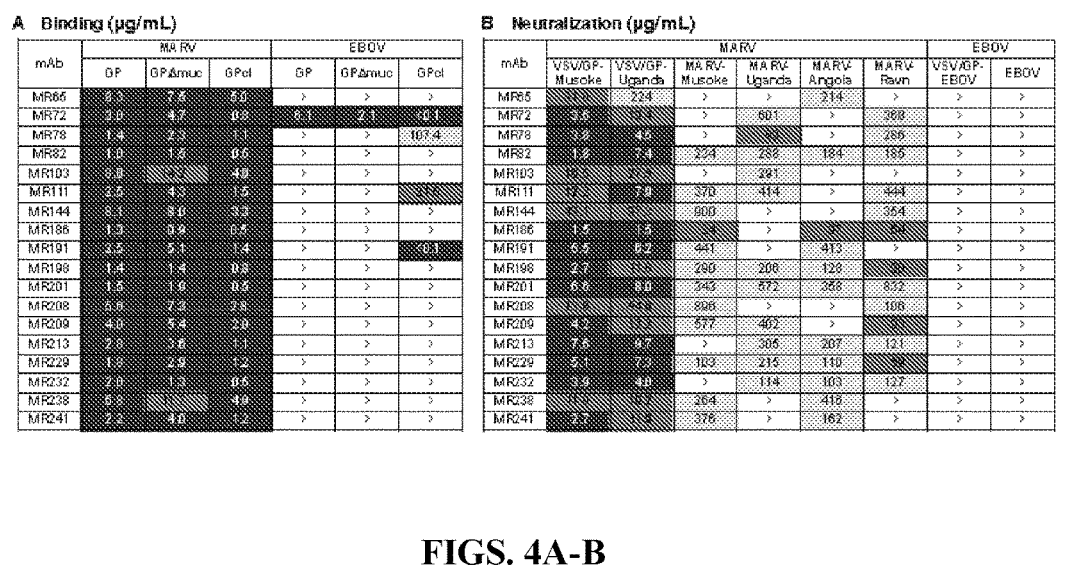

A Binding (µg/mL)

| mAb | MARV | | | EBOV | | |
|---|---|---|---|---|---|---|
| | GP | GPΔmuc | GPcl | GP | GPΔmuc | GPcl |
| MR65 | 3.3 | 7.6 | 5.0 | > | > | > |
| MR72 | 3.0 | 4.7 | 0.9 | 0.1 | 2.1 | <0.1 |
| MR78 | 1.4 | 2.3 | 1.1 | > | > | 107.4 |
| MR82 | 1.0 | 1.6 | 0.6 | > | > | > |
| MR103 | 8.8 | [illegible] | 4.0 | > | > | > |
| MR111 | 3.5 | 4.3 | 1.5 | > | > | [illegible] |
| MR144 | 8.1 | 8.0 | 3.3 | > | > | > |
| MR186 | 1.3 | 0.9 | 0.5 | > | > | > |
| MR191 | 3.5 | 5.1 | 1.4 | > | > | <0.1 |
| MR198 | 1.4 | 1.4 | 0.8 | > | > | > |
| MR201 | 1.5 | 1.9 | 0.5 | > | > | > |
| MR208 | 5.8 | 7.3 | 2.8 | > | > | > |
| MR209 | 4.0 | 5.4 | 2.0 | > | > | > |
| MR213 | 2.8 | 3.8 | 1.1 | > | > | > |
| MR229 | 1.8 | 2.9 | 1.2 | > | > | > |
| MR232 | 2.0 | 1.3 | 0.6 | > | > | > |
| MR238 | 6.3 | [illegible] | 4.0 | > | > | > |
| MR241 | 2.2 | 4.0 | 1.2 | > | > | > |

B Neutralization (µg/mL)

| mAb | MARV | | | | | | EBOV | |
|---|---|---|---|---|---|---|---|---|
| | VSV/GP-Musoke | VSV/GP-Uganda | MARV-Musoke | MARV-Uganda | MARV-Angola | MARV-Ravn | VSV/GP-EBOV | EBOV |
| MR65 | [illegible] | 224 | > | > | 214 | > | > | > |
| MR72 | 3.6 | [illegible] | > | 601 | > | 368 | > | > |
| MR78 | 3.8 | 4.2 | > | [illegible] | > | 286 | > | > |
| MR82 | 1.9 | 7.4 | 234 | 258 | 184 | 185 | > | > |
| MR103 | [illegible] | [illegible] | > | 291 | > | > | > | > |
| MR111 | [illegible] | 7.9 | 370 | 414 | > | 444 | > | > |
| MR144 | [illegible] | [illegible] | 900 | > | > | 354 | > | > |
| MR186 | 1.7 | 1.5 | [illegible] | > | [illegible] | [illegible] | > | > |
| MR191 | 6.5 | 6.2 | 441 | > | 413 | > | > | > |
| MR198 | 2.7 | [illegible] | 290 | 208 | 128 | [illegible] | > | > |
| MR201 | 6.8 | 8.0 | 343 | 572 | 358 | 832 | > | > |
| MR208 | [illegible] | [illegible] | 898 | > | > | 108 | > | > |
| MR209 | 4.2 | [illegible] | 577 | 402 | > | [illegible] | > | > |
| MR213 | 7.6 | 4.7 | > | 305 | 207 | 121 | > | > |
| MR229 | 2.1 | 7.3 | 103 | 215 | 110 | [illegible] | > | > |
| MR232 | 3.9 | 4.0 | > | 114 | 103 | 127 | > | > |
| MR238 | [illegible] | [illegible] | 264 | > | 418 | > | > | > |
| MR241 | 2.7 | [illegible] | 376 | > | 162 | > | > | > |

FIGS. 4A-B

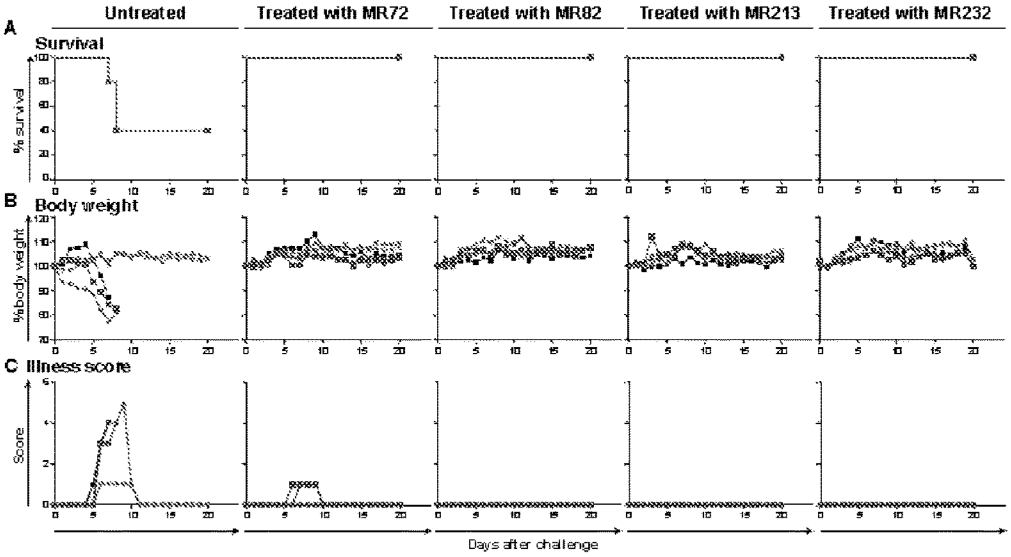
FIGS. 5A-C

A Neutralization of VSV/GP-Uganda

| Group | mAb | Neutralization values | | | Curve fit values ($R^2$) |
|---|---|---|---|---|---|
| | | $EC_{50}$ | $EC_{50}$ lower | $EC_{50}$ upper | |
| 1 | MR48 | > | > | > | 0.0 |
| | MR49 | > | > | > | 0.0 |
| | MR59 | > | > | > | 0.0 |
| | MR73 | > | > | > | 0.0 |
| | MR75 | > | > | > | 0.0 |
| | MR77 | > | > | > | 0.0 |
| | MR84 | > | 619 | > | 0.1 |
| | MR85 | > | > | > | 0.0 |
| | MR114 | > | 340 | > | 0.3 |
| | MR117 | > | 317 | > | 0.4 |
| | MR168 | > | > | > | 0.6 |
| | MR187 | > | > | > | 0.0 |
| | MR237 | > | > | > | 0.0 |
| 2 | MR228 | > | 442 | > | 0.5 |
| | MR235 | > | > | > | 0.0 |
| 3A | MR162 | > | > | > | 0.6 |
| | MR221 | > | > | > | 0.0 |
| | MR224 | > | 855 | > | 0.1 |
| | MR246 | > | > | > | 0.0 |
| 3B | MR55 | 224 | 150 | 343 | [illegible] |
| | MR72 | [illegible] | 5 | 26 | 0.8 |
| | MR78 | 7 | 6 | 12 | 0.9 |
| | MR79 | > | > | > | 0.1 |
| | MR82 | 0 | 0 | 2 | [illegible] |
| | MR103 | [illegible] | [illegible] | 24 | 1.0 |
| | MR111 | 8 | 3 | 16 | 0.9 |
| | MR137 | > | > | > | 0.0 |
| | MR144 | [illegible] | 21 | 45 | 1.0 |
| | MR186 | 2 | 1 | 2 | 1.0 |
| | MR191 | 5 | 4 | 10 | [illegible] |
| | MR198 | 11 | 5 | 14 | 1.0 |
| | MR201 | 8 | 5 | 11 | 0.9 |
| | MR208 | [illegible] | [illegible] | [illegible] | 1.0 |
| | MR209 | [illegible] | 5 | 11 | 0.9 |
| | MR213 | 10 | 6 | 14 | [illegible] |
| | MR229 | 7 | 3 | 12 | [illegible] |
| | MR232 | 4 | 3 | 6 | 0.9 |
| | MR238 | [illegible] | 5 | 17 | 1.0 |
| | MR241 | 12 | 5 | 31 | 0.9 |

B Neutralization of MARV-Uganda

| Group | mAb | Neutralization values | | | Curve fit values ($R^2$) |
|---|---|---|---|---|---|
| | | $EC_{50}$ | $EC_{50}$ lower | $EC_{50}$ upper | |
| 1 | MR48 | > | > | > | 0.0 |
| | MR49 | > | > | > | 0.0 |
| | MR59 | > | 886 | > | 0.6 |
| | MR73 | > | > | > | 0.0 |
| | MR75 | > | > | > | 0.0 |
| | MR77 | > | > | > | 0.0 |
| | MR84 | > | > | > | 0.2 |
| | MR85 | > | 309 | > | 0.0 |
| | MR114 | > | > | > | 0.0 |
| | MR117 | > | 317 | > | 0.4 |
| | MR168 | > | > | > | 0.0 |
| | MR187 | > | > | > | 0.0 |
| | MR237 | > | > | > | 0.0 |
| 2 | MR228 | > | > | > | 0.0 |
| | MR235 | > | > | > | 0.0 |
| 3A | MR162 | > | > | > | 0.0 |
| | MR221 | > | 843 | > | 0.1 |
| | MR224 | > | > | > | 0.0 |
| | MR246 | > | > | > | 0.0 |
| 3B | MR55 | > | > | > | 0.0 |
| | MR72 | 601 | 225 | > | 0.4 |
| | MR78 | [illegible] | [illegible] | 589 | 0.5 |
| | MR79 | > | > | > | 0.0 |
| | MR82 | 288 | 123 | > | 0.6 |
| | MR103 | 291 | 204 | > | 0.7 |
| | MR111 | 414 | 234 | > | 0.7 |
| | MR137 | > | > | > | 0.0 |
| | MR144 | > | > | > | 0.2 |
| | MR186 | > | > | > | 0.0 |
| | MR191 | > | > | > | 0.0 |
| | MR198 | 206 | [illegible] | > | 0.5 |
| | MR201 | 572 | 244 | > | 0.5 |
| | MR208 | > | > | > | 0.0 |
| | MR209 | 402 | 156 | > | 0.6 |
| | MR213 | 305 | 134 | 835 | 0.7 |
| | MR229 | 215 | [illegible] | > | 0.6 |
| | MR232 | 114 | 41 | 489 | 0.5 |
| | MR238 | > | > | > | 0.0 |
| | MR241 | > | 204 | > | 0.2 |

FIGS. 9A-B

ANTIBODY-MEDIATED NEUTRALIZATION OF MARBURG VIRUS

This application is a national phase application under 35 U.S.C. § 371 of International Application No. PCT/US2016/019644, filed Feb. 25, 2016, which claims benefit of priority to U.S. Provisional Application Ser. No. 62/120,657, filed Feb. 25, 2015, the entire contents of which are hereby incorporated by reference.

This invention was made with government support under grant number HDTRA1-13-1-0034 awarded by the Department of Defense and under grant number AI109711 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to antibodies that bind to *Marburg* virus glycoprotein (GP).

2. Background

*Marburg* virus (MARV) and Ebola virus (EBOV) are members of the family Filoviridae, which infect humans and non-human primates causing a hemorrhagic fever with mortality rates up to 90% (Brauburger et al., 2012). There have been a dozen outbreaks of *Marburg* virus infection in humans reported to date, including the most recent report from Uganda of a 30-year old male health worker who died in September, 2014 (WHO, 2014a). As of Jan. 7, 2015, there have been in excess of 20,000 confirmed, probable, and suspected cases of Ebola virus disease (EVD) in the current EBOV outbreak in nine affected countries (Guinea, Liberia, Mali, Nigeria, Senegal, Sierra Leone, Spain, the United Kingdom and the United States of America) with more than 8,000 deaths (WHO, 2014b).

There is no licensed treatment or vaccine for filovirus infection. Recently, several studies showed that filovirus glycoprotein (GP)-specific neutralizing antibodies (nAbs) can reduce mortality following experimental inoculation of animals with a lethal dose of EBOV (Dye et al., 2012; Marzi et al., 2012; Olinger et al., 2012; Qiu et al., 2012; Pettitt et al., 2013; Qiu et al., 2014) or MARV (Dye et al., 2012). The primary target of these nAbs, the filovirus surface GP, is a trimer composed of three heavily glycosylated GP1-GP2 heterodimers (FIG. 6). The GP1 subunit can be divided further into base, head, glycan cap and mucin-like domains (Lee et al., 2008). During viral entry, the mucin-like domain and glycan cap mediate binding to multiple host attachment factors present on the cell membrane. After the virus enters the host cell by macropinocytosis (Nanbo et al., 2010; Saeed et al., 2010), the GP is cleaved by host proteases that remove approximately 80% of the mass of the GP1 subunit, including the mucin-like domain and glycan cap (Chandran et al., 2005; Dube et al., 2009). After cleavage of GP in the endosome, the receptor-binding sites on GP become exposed, and the GP1 head then is able to bind to its receptor, Niemann-Pick C1 (NPC1) protein (Carette et al., 2011; Chandran et al., 2005; Cote et al., 2011). Subsequent conformational changes in GP facilitate fusion between viral and endosomal membranes.

The dense clustering of glycans on the glycan cap and mucin-like domain likely shield much of the surface of EBOV GP from humoral immune surveillance, leaving only a few sites on the EBOV GP protein where nAbs could bind without interference by glycans (Cook and Lee, 2013). Most of the inventors' knowledge about humoral response against Filovirus infections has come from studies of murine Abs that recognize EBOV GP. From those studies, the inventors learned that mouse nAbs preferentially target peptides exposed in upper, heavily glycosylated domains or lower areas (the GP1 base) where rearrangements occur that drive fusion of viral and host membranes (Saphire, 2013). Abs have not been identified that target protein features of the GP1 head subdomain, where the receptor-binding site to NPC1 protein is located. Ab KZ52, the only reported human EBOV GP-specific mAb, was obtained from a phage display library that was constructed from bone marrow RNA obtained from a survivor (Maruyama et al., 1999). KZ52 binds a site at the base of the GP and neutralizes EBOV, most likely by inhibiting the conformational changes required for fusion of viral and endosomal membranes (Lee et al., 2008). Some murine Abs also have been reported to bind to the base region of Ebola virus GPs (Dias et al., 2011, Murin et al., 2014). In contrast, very little is known about the mechanisms by which Abs neutralize MARV. Two murine Abs that bound the mucin-like domain of MARV GP reduced MARV budding from infected cells in culture, but failed to neutralize virus directly (Kajihara et al., 2012). Polyclonal MARV-specific Abs were shown to protect non-human primates when administrated passively after challenge (Dye et al., 2012). The epitopes recognized by such polyclonal nAbs, and their mechanism of neutralization, are unknown.

SUMMARY

Thus, in accordance with the present disclosure, there is provided a method of detecting a *Marburg* virus infection in a subject comprising (a) contacting sample from said subject with an antibody or antibody fragment having clone-paired heavy and light chain CDR sequences from Tables 3 and 4, respectively; and (b) detecting *Marburg* virus glycoprotein (GP) in said sample by binding of said antibody or antibody fragment to GP in said sample. The sample may be a body fluid, such as blood, sputum, tears, saliva, mucous or serum, urine or feces. Detection may comprise ELISA, RIA or Western blot. The method may further comprise performing steps (a) and (b) a second time and determining a change in the GP levels as compared to the first assay.

The antibody or antibody fragment may be further characterized by clone-paired variable sequences as set forth in Tables 1 or 2. The antibody or antibody fragment may be encoded by light and heavy chain variable sequences having 70%, 80%, or 90% identity to clone-paired sequences from Table 1. The antibody or antibody fragment may be encoded by light and heavy chain variable sequences having 95% identity to clone-paired sequences from Table 2. The antibody fragment may be a recombinant ScFv (single chain fragment variable) antibody, Fab fragment, F(ab')2 fragment, or Fv fragment. The antibody may not bind to Ebola virus.

In another embodiment, there is provided a method of treating a subject infected with *Marburg* Virus, or reducing the likelihood of infection of a subject at risk of contracting *Marburg* virus, comprising delivery to said subject an antibody or antibody fragment having clone-paired heavy and light chain CDR sequences from Tables 3 and 4, respectively. Delivering may comprise antibody or antibody fragment administration, or genetic delivery with an RNA or DNA sequence or vector encoding the antibody or antibody fragment. The antibody or antibody fragment may be characterized by clone-paired variable sequences as set forth in Table 1. The antibody or antibody fragment may be characterized by clone-paired variable sequences as set forth in Table 2. The antibody or antibody fragment may be encoded by light and heavy chain variable sequences having 70%, 80%, or 90% identity to clone-paired sequences from Table 1. The antibody or antibody fragment may be encoded by light and heavy chain variable sequences having 95% identity to clone-paired sequences from Table 2. The antibody fragment may be is a recombinant ScFv (single chain fragment variable) antibody, Fab fragment, F(ab')2 fragment, or Fv fragment. The antibody may be an IgG, may be a chimeric antibody, and/or may also binds to Ebola virus.

Also provided is a monoclonal antibody or fragment thereof, wherein the antibody is characterized by clone-paired heavy and light chain CDR sequences from Tables 3 and 4, respectively. The antibody or antibody fragment may be encoded by light and heavy chain variable sequences according to clone-paired sequences from Table 1. The antibody or antibody fragment may be encoded by light and heavy chain variable sequences having 70%, 80%, or 90% identity to clone-paired sequences from Table 1. The antibody or antibody fragment may be encoded by light chain and heavy variable sequences according to clone-paired sequences from Table 2. The antibody or antibody fragment may be encoded by light and heavy chain variable sequences having 95% identity to clone-paired sequences from Table 2. The antibody fragment may be a recombinant ScFv (single chain fragment variable) antibody, Fab fragment, F(ab')2 fragment, or Fv fragment.

The antibody may be a chimeric antibody, or is bispecific antibody that targets a *Marburg* virus or Ebola virus antigen other than glycoprotein. The bispecific antibody fragment thereof may be bispecific antibody that (a) targets a structural feature of a *Marburg* virus or Ebola virus particle, and (b) targets receptor binding domain of *Marburg* or Ebola virus. The structural feature may be a *Marburg* or Ebola virus glycoprotein domain other than the receptor binding domain. The structural feature may be a *Marburg* or Ebola virus virion structure other than the glycoprotein, such as a lipid, carbohydrate or protein. The antibody or fragment may be is a bispecific antibody that (a) targets a structural feature of a *Marburg* virus or Ebola virus particle and (b) targets a host cell surface structure cells that is trafficked to endosomes. The host cell surface structure may be a virus receptor (the cholesterol transporter Niemann-Pick C1) or glycan. The antibody may be an IgG. The antibody may also bind to Ebola virus. The antibody or antibody fragment may further comprise a cell penetrating peptide or is an intrabody.

In addition, there is provided an engineered cell encoding an antibody or fragment thereof characterized by clone-paired heavy and light chain CDR sequences from Tables 3 and 4, respectively. The antibody may be antibody fragment is encoded by light and heavy chain variable sequences according to clone-paired sequences from Table 1. The antibody or antibody fragment may be encoded by light and heavy chain variable sequences having 70%, 80%, or 90% identity to clone-paired sequences from Table 1. The antibody or antibody fragment may be encoded by light chain and heavy variable sequences according to clone-paired sequences from Table 2. The antibody or antibody fragment may be encoded by light and heavy chain variable sequences having 95% identity to clone-paired sequences from Table 2. The antibody fragment may be a recombinant ScFv (single chain fragment variable) antibody, Fab fragment, $F(ab')_2$ fragment, or Fv fragment. The antibody may be a chimeric antibody. The antibody may be an IgG. The antibody may also bind to Ebola virus. The antibody or antibody fragment may further comprise a cell penetrating peptide or is an intrabody.

In yet another embodiment, there is provided a method of treating a subject infected with *Marburg* virus or Ebola virus, or reducing the likelihood of infection of a subject at risk of contracting *Marburg* virus or Ebola virus, comprising delivery to said subject an antibody or antibody fragment having clone-paired heavy and light chain CDR sequences from Tables 3 and 4, respectively. The antibody or antibody fragment may be a chimeric antibody, or is bispecific antibody that targets a *Marburg* virus or Ebola virus antigen other than glycoprotein. The antibody or antibody fragment may be a bispecific antibody that (a) targets a structural feature of a *Marburg* virus or Ebola virus particle that effects attachment of the antibody to the virus, and thus endocytosis, and (b) targets receptor binding domain of *Marburg* or Ebola virus in the endosome to block virus attachment to the receptor. The structural feature may be a *Marburg* or Ebola virus glycoprotein domain other than the receptor binding domain, or the structural feature may be a *Marburg* or Ebola virus virion structure other than the glycoprotein. The virion structure is a lipid, carbohydrate or protein. The antibody or antibody fragment may be a bispecific antibody that (a) targets a structural feature of a *Marburg* virus or Ebola virus particle that effects attachment of the antibody to the virus, and thus endocytosis, and (b) targets a host cell surface structure cells that is trafficked to endosomes. The antibody or antibody fragment may be characterized by clone-paired variable sequences as set forth in Table 1. The antibody or antibody fragment may be characterized by clone-paired variable sequences as set forth in Table 2. The antibody or antibody fragment may be encoded by light and heavy chain variable sequences having 70%, 80%, or 90% identity to clone-paired sequences from Table 1. The antibody or antibody fragment may be encoded by light and heavy chain variable sequences having 95% identity to clone-paired sequences from Table 2. The antibody fragment may be is a recombinant ScFv (single chain fragment variable) antibody, Fab fragment, $F(ab')_2$ fragment, or Fv fragment.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D. MARV neutralizing mAbs display a unique binding pattern and target a distinct antigenic region on the GP surface. (FIG. 1A) Neutralization activity of MR77 (non-neutralizing antibody) or MR213 (neutralizing antibody) against VSV/GP-Uganda (red circles) or MARV-Uganda (black circles). Error bars represent the standard errors of the experiment performed in triplicate. (FIG. 1B) Binding of representative mAbs from four distinct Binding Groups to the MARV GP (blue squares) or MARV GPΔmuc (green squares). Dotted line indicates 0.5 μg/mL threshold for categorizing Group 3 antibodies as possessing low (3A) or high (3B) $EC_{50}$ values. (FIG. 1C) Heatmap showing the neutralization potency of MARV GP-specific mAbs against VSV/GP-Uganda or MARV-Uganda. $IC_{50}$ value for each virus-mAb combination is shown, with dark red, orange, yellow or white shading indicating high, intermediate, low or no potency. $IC_{50}$ values greater than 1,000 μg/mL are indicated by >. Neutralization assays were performed in triplicate. (FIG. 1D) Data from competition binding assays using mAbs from Binding Groups 2, 3A or 3B. Numbers indicate the percent binding of the competing mAb in the presence of the first mAb, compared to binding of competing mAb alone. MAbs were judged to compete for the same site if maximum binding of the competing mAb was reduced to <30% of its un-competed binding (black boxes with white numbers). MAbs were considered non-competing if maximum binding of the competing mAb was >70% of its un-competed binding (white boxes with red numbers). Grey boxes with black numbers indicate an intermediate phenotype (between 30 and 70% of un-competed binding).

FIGS. 2A-D. Neutralizing antibodies from a human survivor of MARV bind to the receptor-binding site of GP at two distinct angles of approach. (FIG. 2A) Representative reference-free 2D class averages of the MARV GPAMuc: MR Fab complexes. (FIG. B) EM reconstructions of seven Fab fragments of neutralizing antibodies bound to MARV GPΔmuc (side views). All seven antibodies target a similar epitope on the top of GP. (FIG. 2C) These antibodies can be subdivided based on their angles of approach: i) those that bind toward the top and side of GP1 at a shallow angle relative to the central three-fold axis (MR72 in red, MR78 in orange, MR201 in yellow or MR82 in green) and ii) those that bind at a steeper angle toward the top of GP1 (MR191 in cyan, MR111 in blue or MR198 in purple). (FIG. 2D) The crystal structure of EBOV GPΔmuc (GP1 in white and GP2 in dark grey) is modeled into the MARV GP density (mesh) and the angles of approach of the neutralizing antibodies are indicated with arrows, colored as in FIG. 2B. The footprint of the antibodies is indicated by a black circle targeting residues in the putative receptor-binding site (RBS) through a variety of approach angles.

FIGS. 3A-B. Generation of escape mutants for MARV neutralizeng antibodies. (FIG>3A) VSV-MARV-72.5 (dotted lines) or VSV-MARV-78.1 (dashed line) escape mutations mapped onto the domain schematic of MARV GP. RBS=Receptor binding site; GLC=glycan cap; MUC=mucin-like domain. (FIG. 3B) Neutralization activity of antibodies from Binding Group 3B against wild-type VSV/GP-Uganda (circles, straight curves), VSV/GP-72.5 (squares, dotted curves) or VSV/GP-78.1 (triangles, dashed curves) escape mutant viruses.

FIGS. 4A-B. Breadth of binding or neutralization of human MARV-specific mAbs for diverse filoviruses. (FIG. 4A) A heat map showing the binding in ELISA of neutralizing mAbs from Binding Group 3B to the MARV and EBOV GPs. $EC_{50}$ value for each antigen-mAb combination is shown, with dark red shading indicating lower $EC_{50}$ values and orange or yellow shading indicating intermediate or higher $EC_{50}$ values. $EC_{50}$ values greater than 1,000 μg/mL are indicated by >. (FIG. 4B) A heatmap showing the neutralization breadth of mAbs from Binding Group 3B. The $IC_{50}$ value for each virus-mAb combination is shown, with dark red shading indicating increased potency and orange or yellow shading indicating intermediate or low potency. $IC_{50}$ values greater than 1,000 μg/mL are indicated by >. Neutralization assays were performed in triplicate.

FIGS. 5A-C. Survival and clinical overview of mice treated with MARV mAbs. Groups of mice at 5 animals per group were injected with individual mAbs by the intraperitoneal route twice: 1 h prior and 24 h after MARV challenge at 100 μg per treatment. Untreated animals served as controls. (FIG. 5A) Kaplan-Meier survival curves. (FIG. 5B) Body weight (FIG. 5C) Illness score.

FIGS. 9A-B. Heatmaps Showing the Neutralization Potency of MARV GP-Specific mAbs against VSV/GP-Uganda in FIG. 9A or MARV-Uganda in FIG. 9B, Related to FIGS. 1A-D. (FIGS. 9A-B) Half maximal inhibitory concentration ($IC_{50}$) and confidence interval values (in mg/ml) for each virus-mAb combination are shown, with dark red, orange, yellow or white shading indicating high, intermediate, low or no potency. $IC_{50}$ values greater than 1,000 mg/ml are indicated by >. R2 values indicating curve fit are shown for each virus-mAb combination, with dark pink color indicating high R2 values. Neutralization assays were performed in triplicate.

Binding Group 1: Emax GP<2,

Binding Group 2: Emax GP>2, $EC_{50}$ GP<$EC_{50}$ GPDmuc,

Binding Group 3: Emax GP>2, $EC_{50}$ GP z$EC_{50}$ GPDmuc,

Binding Group 3A: Emax GP>2, $EC_{50}$ GP z$EC_{50}$ GPDmuc, $EC_{50}$ GP<0.5 mg/ml (dashed line), and Binding Group 3B: Emax GP>2, $EC_{50}$ GP z$EC_{50}$ GPDmuc, $EC_{50}$ GP>0.5 mg/ml.

Figure 11A:
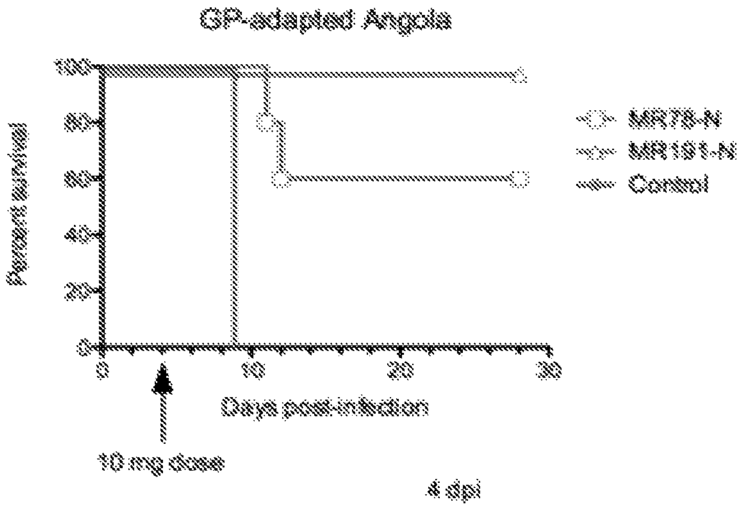
Figure 11B:
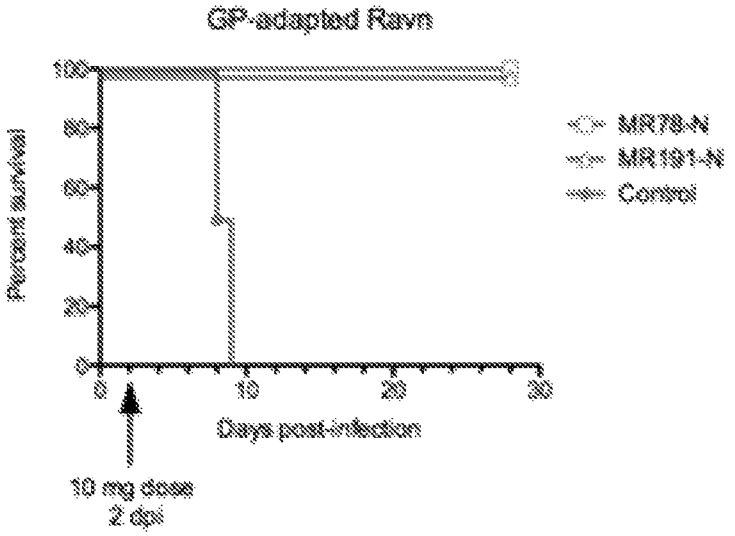

FIGS. 11A-B. Testing of two *Marburg* GP monoclonal antibodies for therapeutic effect in a fatal guinea pig challenge model. (FIG. 11A) Guinea pigs challenged with guinea pig adapted Angola strain of *Marburg* virus (treatment with 10 mg per animal on day 4 post-infection). (FIG. 11B) Guinea pigs challenged with guinea pig adapted Ravn strain of *Marburg* virus (treatment with 10 mg per animal on day 2 post-infection)

Figure 12A:
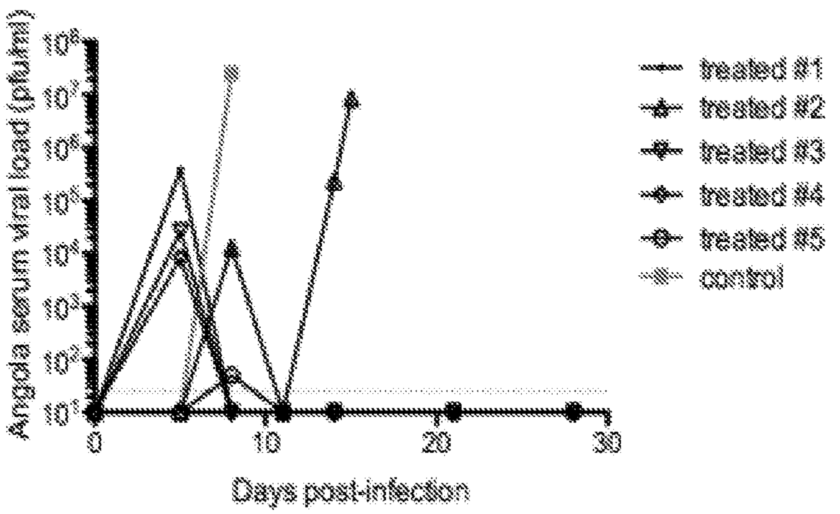
Figure 12B:
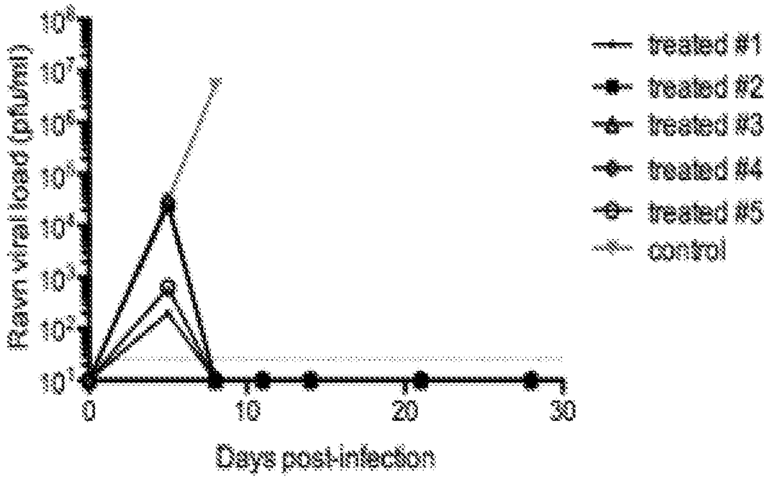
Figure 13A:
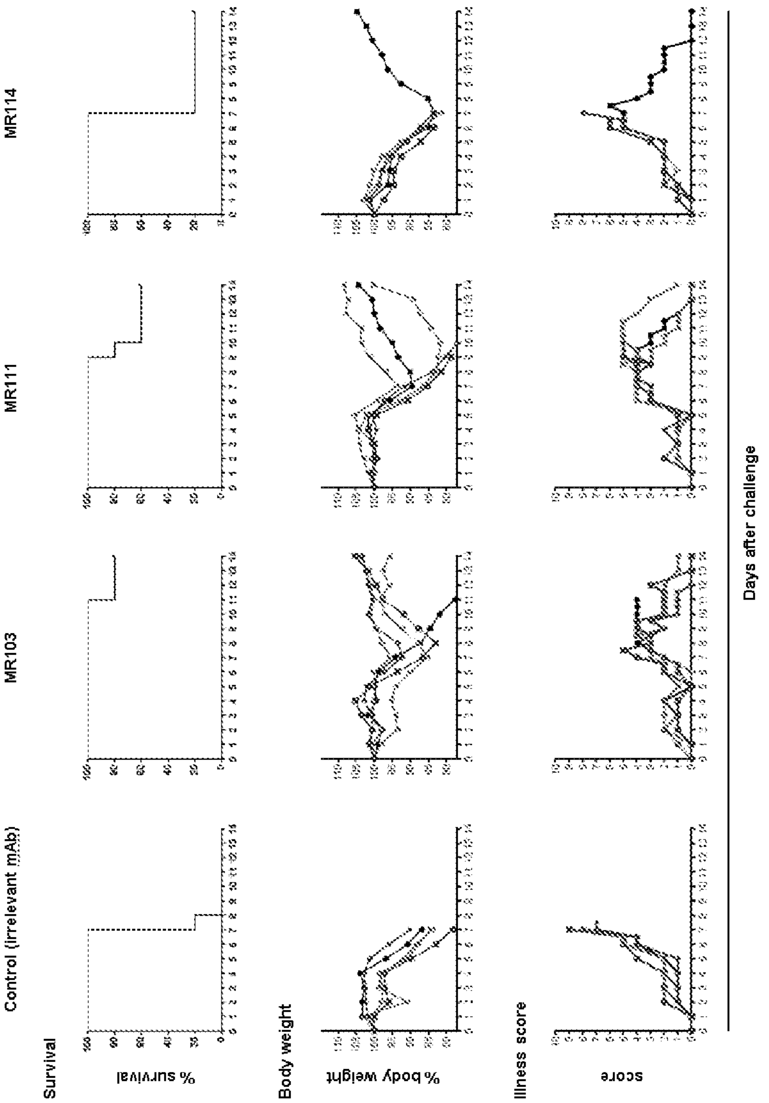
Figure 13B:
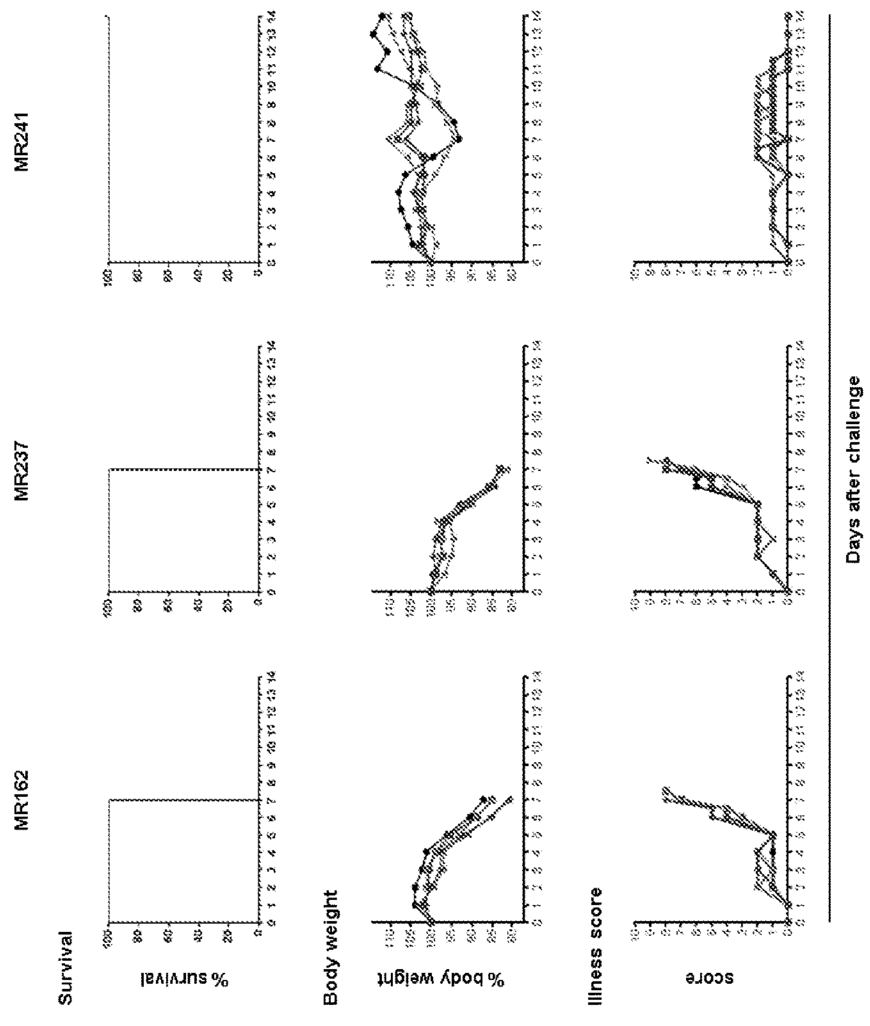
Figure 13C:
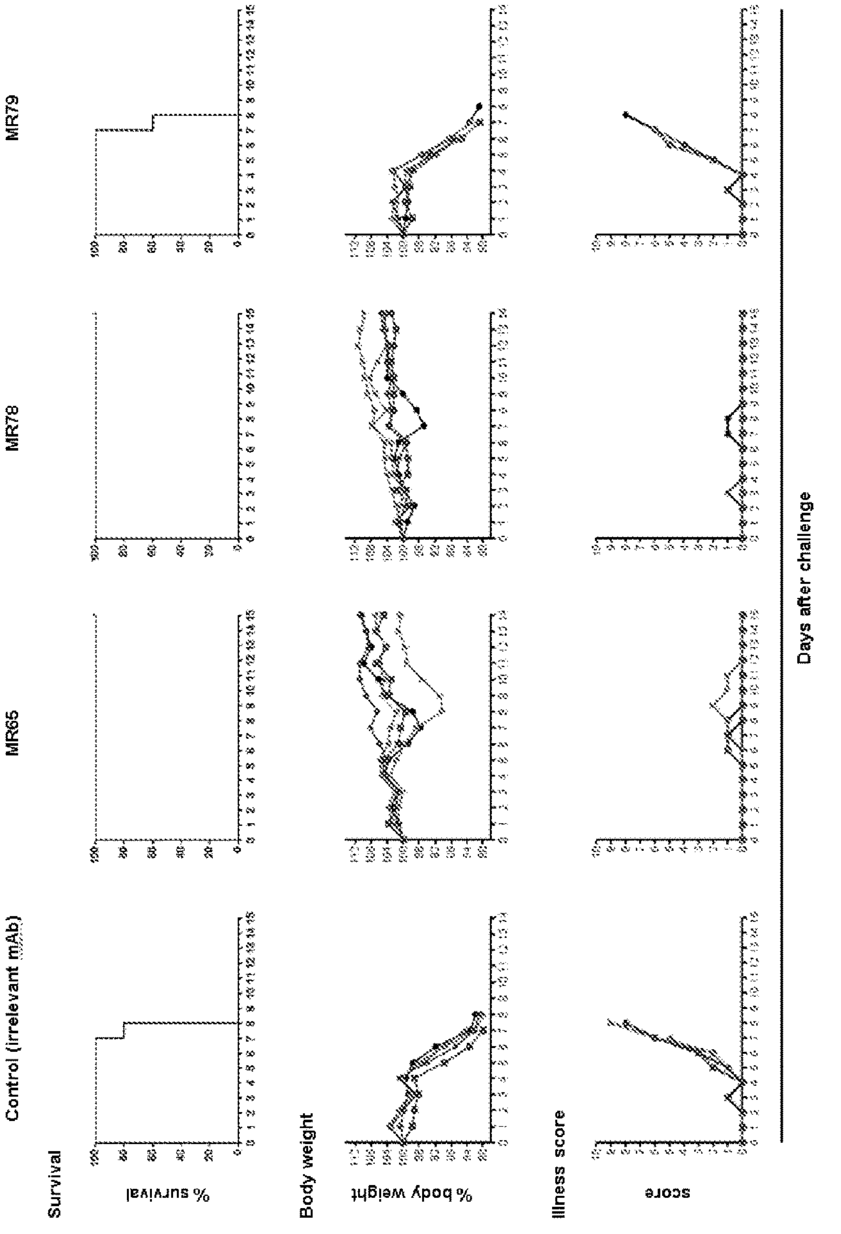
Figure 13D:
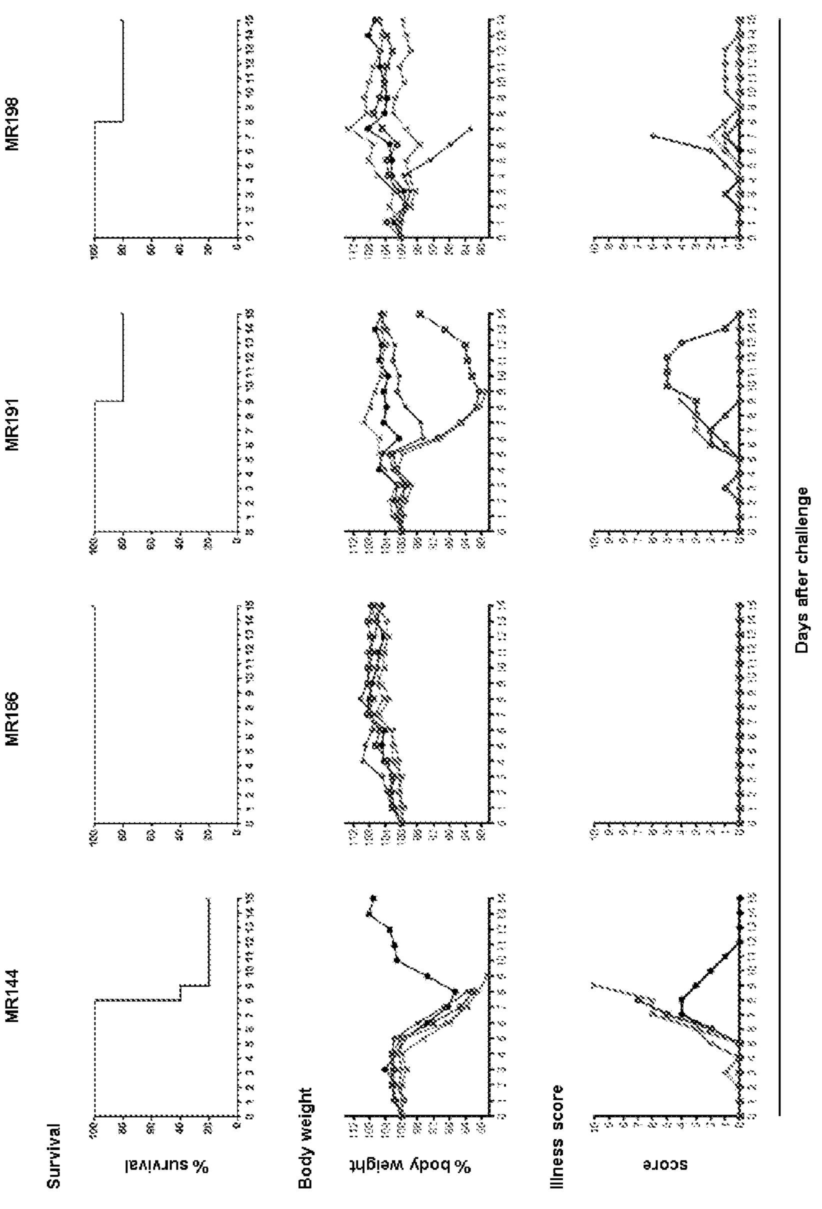
Figure 13E:
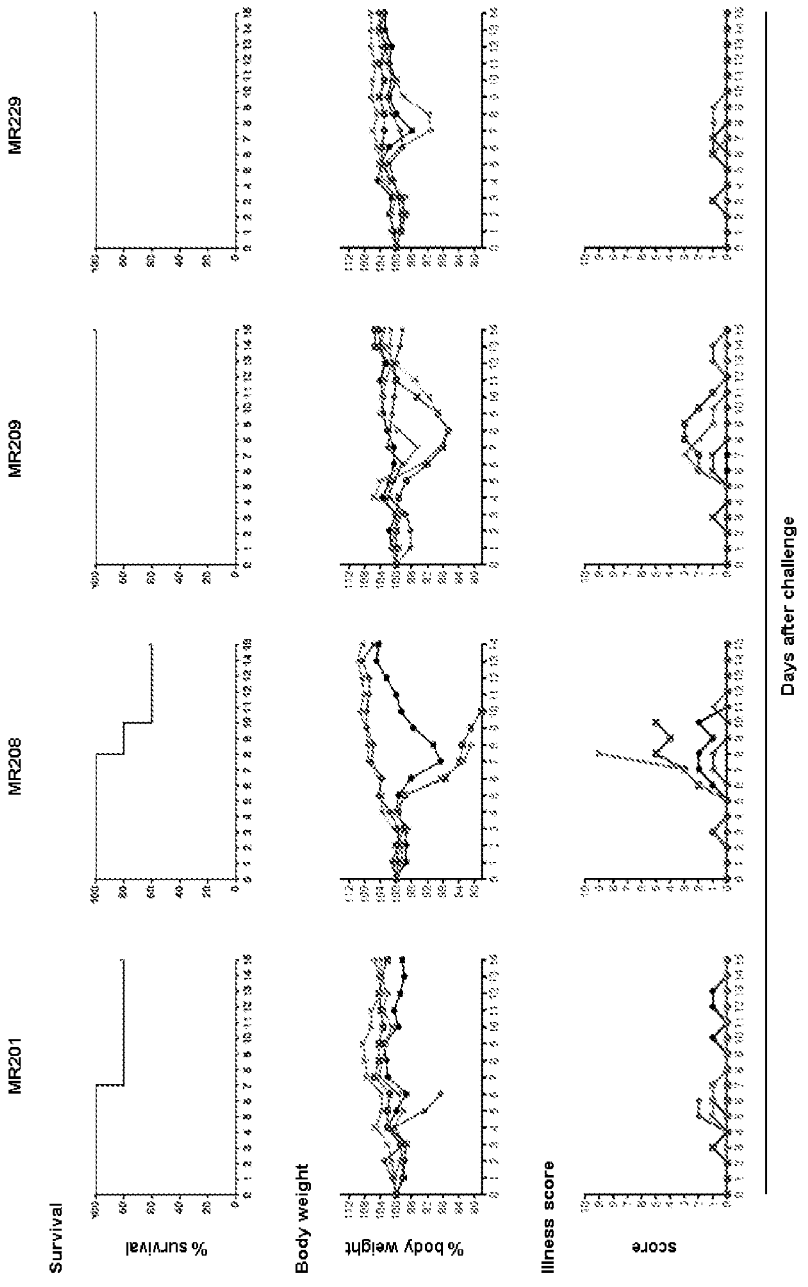
Figure 13F:
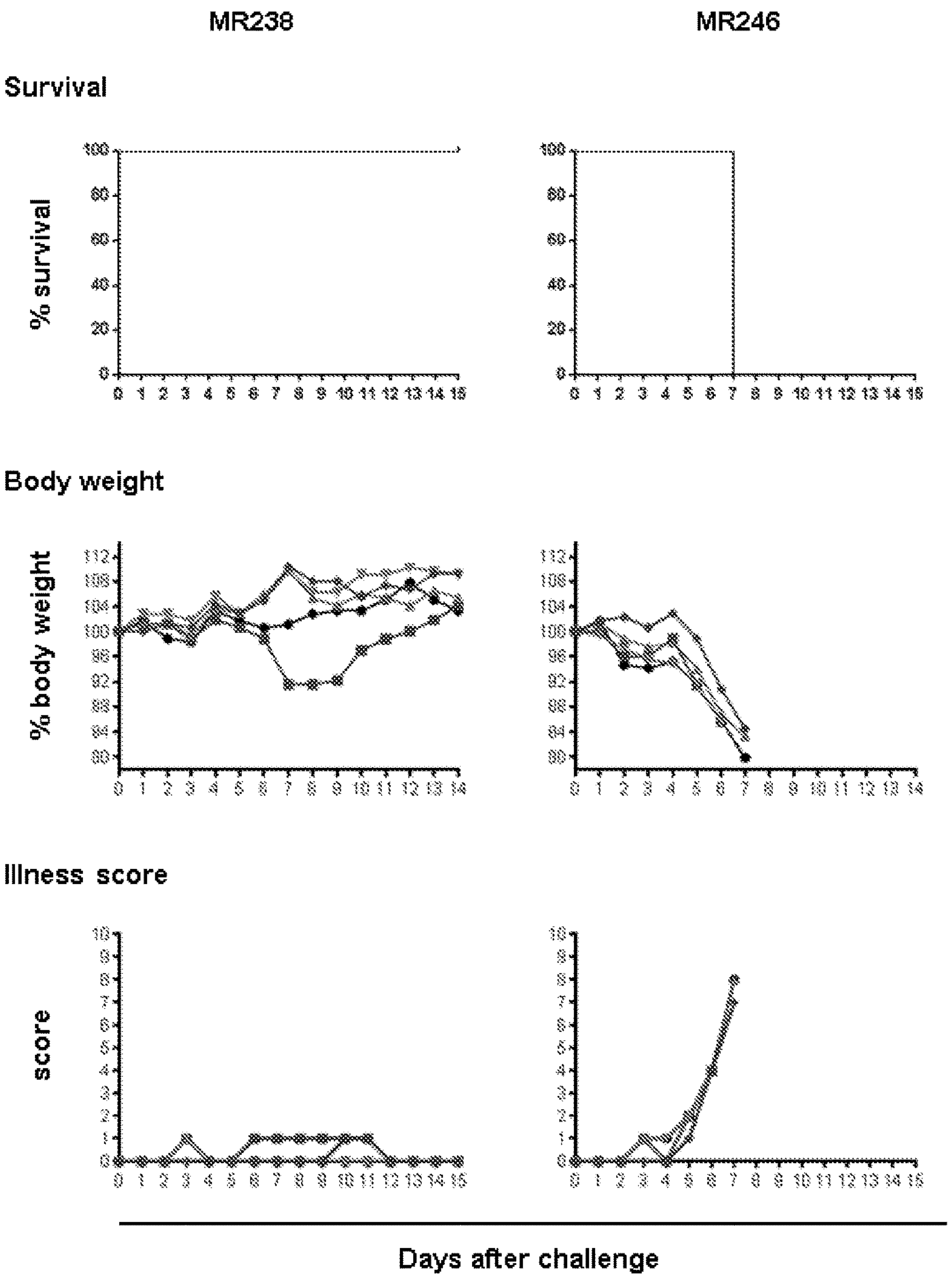
Figure 13G:
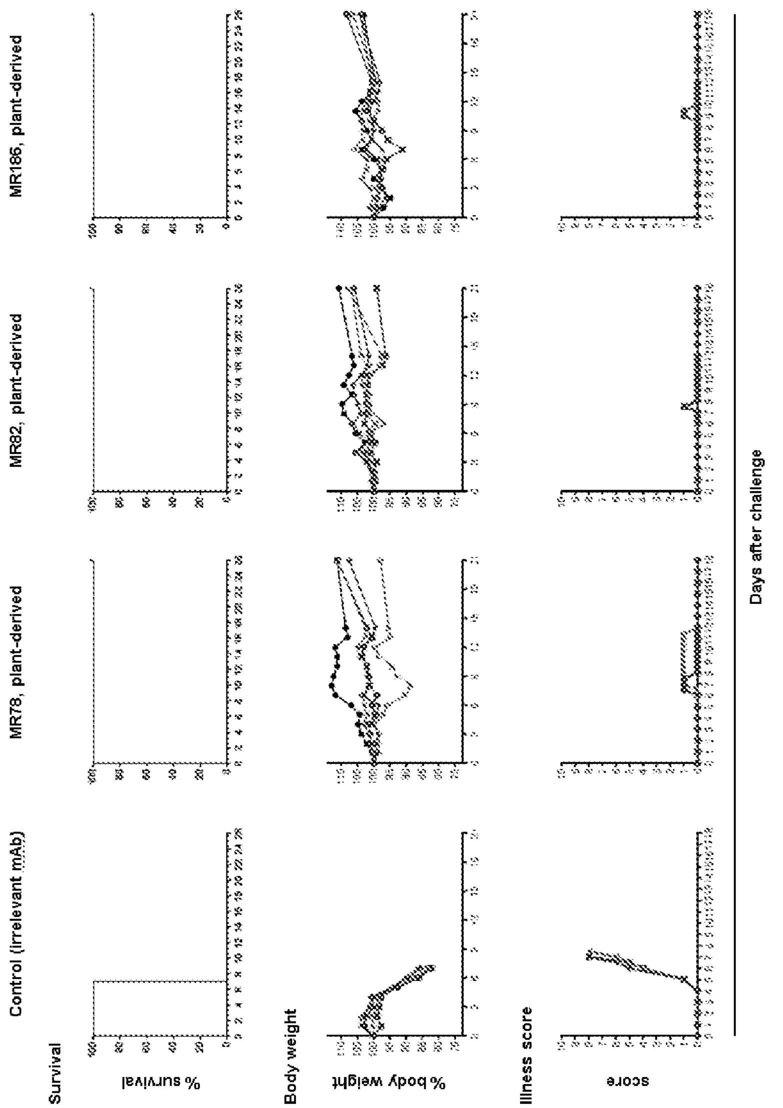
Figure 13H:
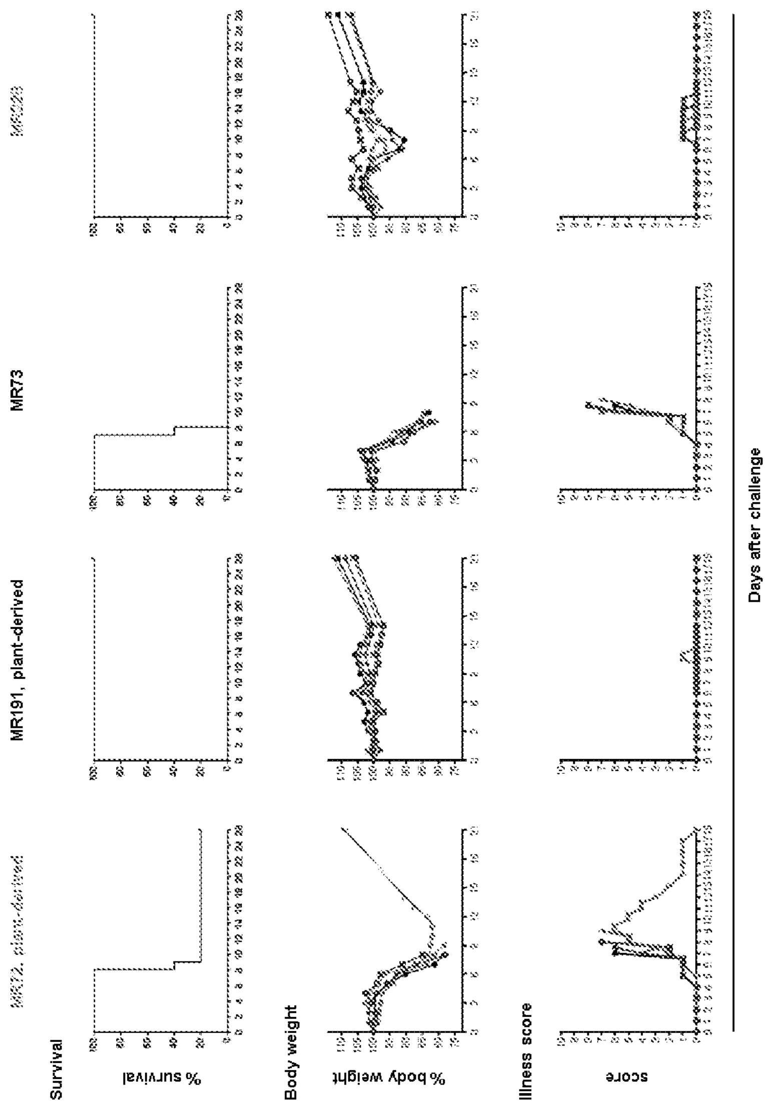
Figure 13I:
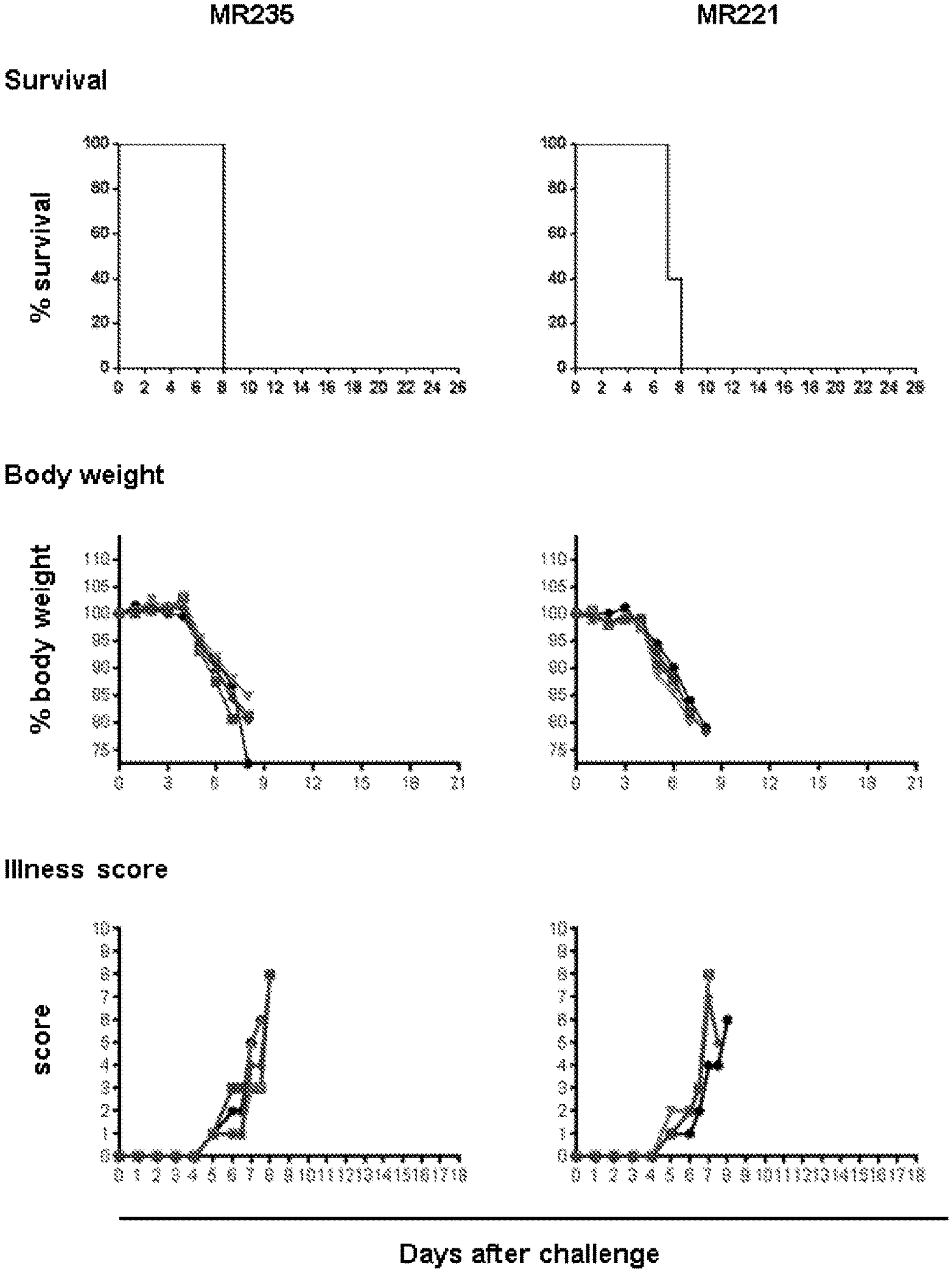
Figure 13J:
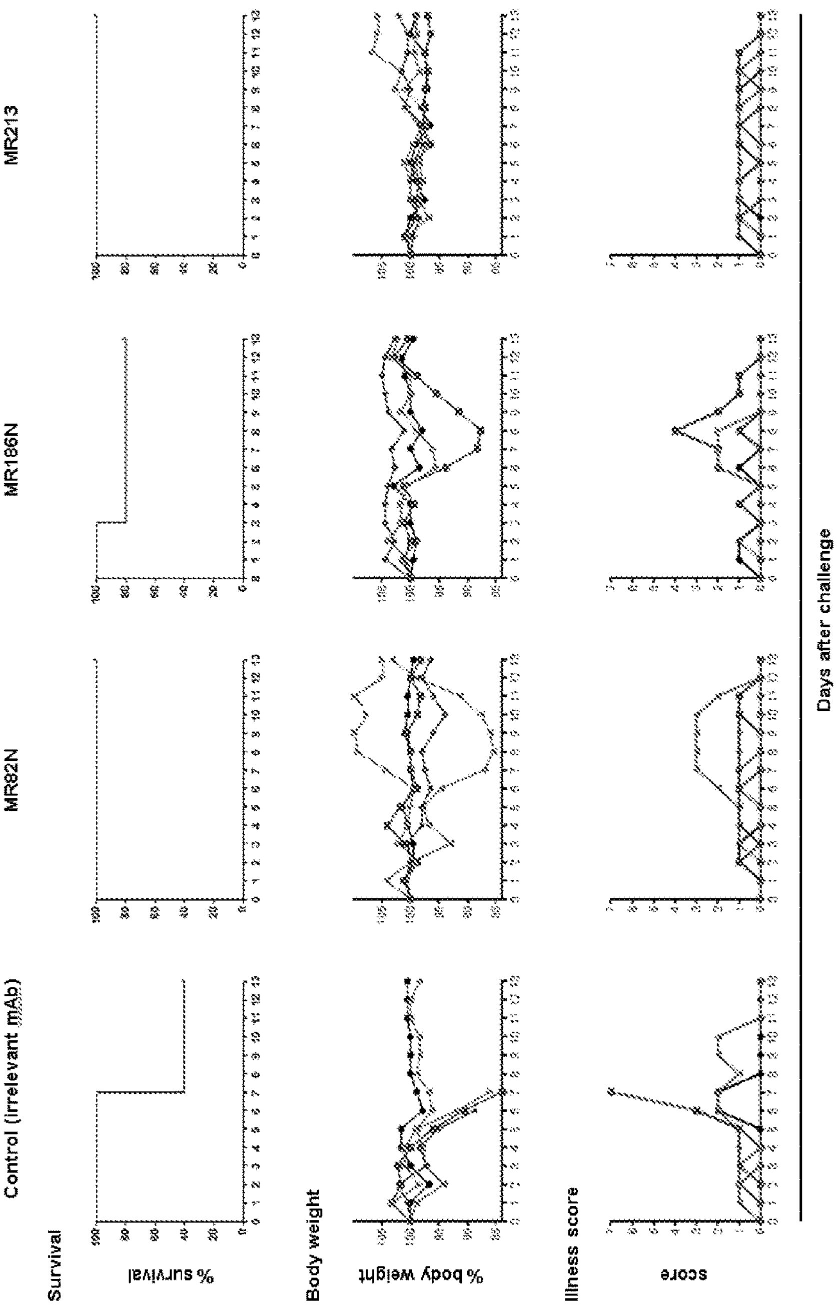

FIGS. 12A-B. Monkey challenge with two *Marburg* virus strains. (FIG. 12A) Monkeys challenged with Angola strain of *Marburg* virus (treatment on day 5 post-infection). (FIG. 12B) Monkeys challenged with Ravn strain of *Marburg* virus (treatment on day 5 post-infection)

FIGS. 13A-J. Testing of additional antibodies in mice challenged with a lethal dose of mouse-adapted *Marburg* virus. Mice challenged with virus and 24 hours later injected with 100 micrograms of many of the antibodies described here, including: MR78 plant derived, MR82 plant derived, MR186 plant derived, MR191 plant derived and mammalian cell expressed MR73, MR228, MR235, MR221, MR65, MR78, MR79, MR103, MR111, MR114, MR144, MR186, MR191, MR198, MR201, MR208, MR209, MR229, MR238, MR246. Most of the antibodies mediated a therapeutic effect. Especially of note is that the mAb MR228 that did not neutralize in vitro mediated a therapeutic effect in vivo, identifying a new antigenic site and mode of protection, by delivery of a non-receptor binding site antibody that protects by a non-neutralizing mechanism, such as ADCC.

DESCRIPTION OF ILLUSTRATIVE EMBODIMENTS

The inventor isolated a panel of neutralizing antibodies (nAbs) from a human MARV survivor that bound to MARV glycoprotein (GP) and competed for binding to a single major antigenic site. Remarkably, several of the Abs also bound to Ebola virus (EBOV) GP. Single-particle EM structures of Ab-GP complexes revealed that all the nAbs bound to MARV GP at or near the predicted region of the receptor-binding site. The presence of the glycan cap or mucin-like domain blocked binding of nAbs to EBOV GP but not to MARV GP. The data suggest that MARV nAbs inhibit virus by binding to infectious virions at the exposed MARV receptor-binding site, revealing a new mechanism of Filovirus inhibition. These and other aspects of the disclosure are described in detail below.

I. MARBURG VIRUS

*Marburg* virus is a hemorrhagic fever virus of the Filoviridae family of viruses and a member of the species *Marburg marburgvirus*, genus *Marburgvirus. Marburg* virus (MARV) causes *Marburg* virus disease in humans and nonhuman primates, a form of viral hemorrhagic fever. *Marburg* virus was first noticed and described during small epidemics in the German cities *Marburg* and Frankfurt and the Yugoslav capital Belgrade in the 1960s. Workers were accidentally exposed to tissues of infected grivets (*Chlorocebus aethiops*) at the city's former main industrial plant, the Behringwerke, then part of Hoechst, and today of CSL Behring. During these outbreaks, 31 people became infected and seven of them died. MARV is a Select Agent, WHO Risk Group 4 Pathogen (requiring biosafety level 4-equivalent containment), NIH/National Institute of Allergy and Infectious Diseases Category A Priority Pathogen, Centers for Disease Control and Prevention Category A Bioterrorism Agent, and is listed as a biological agent for export control by the Australia Group.

*Marburg* virus was first described in 1967. Today, the virus is one of two members of the species *Marburg marburgvirus*, which is included in the genus *Marburgvirus*, family Filoviridae, order Mononegavirales. The name *Marburg* virus is derived from *Marburg* (the city in Hesse, Germany, where the virus was first discovered) and the taxonomic suffix virus. *Marburg* virus was first introduced under this name in 1967. In 2005, the virus name was changed to *Lake Victoria marburgvirus*, which unfortunately was the same spelling as its specie *Lake Victoria marburgvirus*. However, most scientific articles continued to refer to *Marburg* virus. Consequently, in 2010, the name *Marburg* virus was reinstated and the species name changed. A previous abbreviation for the virus was MBGV.

A virus that fulfills the criteria for being a member of the species *Marburg marburgvirus* is a *Marburg* virus if its genome diverges from that of the prototype *Marburg* marburgvirus, *Marburg* virus variant Musoke (MARV/Mus), by <10% at the nucleotide level. MARV is one of two marburgviruses that causes *Marburg* virus disease (MVD) in humans (in the literature also often referred to as *Marburg* hemorrhagic fever, MHF).

Like all mononegaviruses, marburgvirions contain non-infectious, linear nonsegmented, single-stranded RNA genomes of negative polarity that possesses inverse-complementary 3' and 5' termini, do not possess a 5' cap, are not polyadenylated, and are not covalently linked to a protein. *Marburgvirus* genomes are approximately 19 kb long and contain seven genes in the order 3'-UTR—NP-VP35-VP40-GP-VP30-VP24-L-5'-UTR. The genomes of the two different marburgviruses (MARV and RAVV) differ in sequence.

Like all filoviruses, marburgvirions are filamentous particles that may appear in the shape of a shepherd's crook or in the shape of a "U" or a "6", and they may be coiled, toroid, or branched. Marburgvirions are generally 80 nm in width, but vary somewhat in length. In general, the median particle length of marburgviruses ranges from 795 to 828 nm (in contrast to ebola virions, whose median particle length was measured to be 974-1,086 nm), but particles as long as 14,000 nm have been detected in tissue culture. Marburgvirions consist of seven structural proteins. At the center is the helical ribonucleocapsid, which consists of the genomic RNA wrapped around a polymer of nucleoproteins (NP). Associated with the ribonucleoprotein is the RNA-dependent RNA polymerase (L) with the polymerase cofactor (VP35) and a transcription activator (VP30). The ribonucleoprotein is embedded in a matrix, formed by the major (VP40) and minor (VP24) matrix proteins. These particles are surrounded by a lipid membrane derived from the host cell membrane. The membrane anchors a glycoprotein ($GP_{1,2}$) that projects 7 to 10 nm spikes away from its surface. While nearly identical to ebolavirions in structure, marburgvirions are antigenically distinct.

Niemann-Pick C1 (NPC1) appears to be essential for Ebola and *Marburg* virus infection. Two independent studies reported in the same issue of Nature showed that Ebola virus cell entry and replication requires the cholesterol transporter protein NPC1. When cells from patients lacking NPC1 were exposed to Ebola virus in the laboratory, the cells survived and appeared immune to the virus, further indicating that Ebola relies on NPC1 to enter cells. This might imply that genetic mutations in the NPC1 gene in humans could make some people resistant to one of the deadliest known viruses affecting humans. The same studies described similar results with Ebola's cousin in the filovirus group, *Marburg* virus, showing that it too needs NPC1 to enter cells. Furthermore, NPC1 was shown to be critical to filovirus entry because it mediates infection by binding directly to the viral envelope glycoprotein and that the second lysosomal domain of NPC1 mediates this binding.

In one of the original studies, a small molecule was shown to inhibit Ebola virus infection by preventing the virus glycoprotein from binding to NPC1. In the other study, mice that were heterozygous for NPC1 were shown to be protected from lethal challenge with mouse adapted Ebola virus. Together, these studies suggest NPC1 may be potential therapeutic target for an Ebola anti-viral drug.

The *Marburg* virus life cycle begins with virion attachment to specific cell-surface receptors, followed by fusion of the virion envelope with cellular membranes and the concomitant release of the virus nucleocapsid into the cytosol. The virus RdRp partially uncoats the nucleocapsid and transcribes the genes into positive-stranded mRNAs, which are then translated into structural and nonstructural proteins. *Marburgvirus* L binds to a single promoter located at the 3' end of the genome. Transcription either terminates after a gene or continues to the next gene downstream. This means that genes close to the 3' end of the genome are transcribed in the greatest abundance, whereas those toward the 5' end are least likely to be transcribed. The gene order is therefore a simple but effective form of transcriptional regulation. The most abundant protein produced is the nucleoprotein, whose concentration in the cell determines when L switches from gene transcription to genome replication. Replication results in full-length, positive-stranded antigenomes that are in turn transcribed into negative-stranded virus progeny genome copies. Newly synthesized structural proteins and genomes self-assemble and accumulate near the inside of the cell membrane. Virions bud off from the cell, gaining their envelopes from the cellular membrane they bud from. The mature progeny particles then infect other cells to repeat the cycle.

Diagnosis is usually not made from clinical findings. There are polymerase chain reaction (PCR) and enzyme linked immunosorbent assays (ELISA) that can detect the *Marburg* virus later in the course of the disease.

Like Ebola and many other viral diseases, there is no specific treatment for *Marburg* hemorrhagic fever. Patients are given supportive hospital care by maintaining their fluid and electrolyte balance and other considerations, such as replacing lost blood and maintaining a good oxygen supply.

II. MONOCLONAL ANTIBODIES AND PRODUCTION THEREOF

A. General Methods

It will be understood that monoclonal antibodies binding to *Marburg* virus will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood.

The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis.

Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, which in this case is for *Marburg* virus glycoprotein (GP). Those of skill in the art, by assessing the binding specificity/affinity of a given antibody using techniques well known to those of skill in the art, can determine whether such antibodies fall within the scope of the instant claims. In one aspect, there are provided a monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing apply to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas are cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form “chimeric” binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage diplay and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT OF MARBURG INFECTION

A. Formulation and Administration

The present disclosure provides pharmaceutical compositions comprising anti-*Marburg* virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines of the present disclosure, as described herein, can be formulated for parenteral administration, e.g., formulated for injection via the intradermal, intravenous, intramuscular, subcutaneous, or even intraperitoneal routes. Administration by the intradermal and intramuscular routes are specifically contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one to might mention astatine$^{211}$, $^{14}$carbon, $^{51}$chromium, $^{36}$chlorine, $^{57}$cobalt, $^{57}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99}$m and/or yttrium$^{90}$. $^{125}$I is often being preferred for use in certain embodiments, and technicium$^{99}$m and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting *Marburg* virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of *Marburg* virus antibodies directed to specific parasite epitopes in samples also is provided. The steps of various useful immunodetection methods have been described in the scientific literature, such as, e.g., Doolittle and Ben-Zeev (1999), Gulbis and Galand 11993), De Jager et al. (1993), and Nakamura et al. (1987). In general, the immunobinding methods include obtaining a sample suspected of containing *Marburg* virus, and contacting the sample with a first antibody in accordance with the present disclosure, as the case may be, under conditions effective to allow the formation of immunocomplexes.

These methods include methods for purifying *Marburg* virus or related antigens from a sample. The antibody will preferably be linked to a solid support, such as in the form of a column matrix, and the sample suspected of containing the *Marburg* virus or antigenic component will be applied to the immobilized antibody. The unwanted components will be washed from the column, leaving the *Marburg* virus antigen immunocomplexed to the immobilized antibody, which is then collected by removing the organism or antigen from the column.

The immunobinding methods also include methods for detecting and quantifying the amount of *Marburg* virus or related components in a sample and the detection and quantification of any immune complexes formed during the binding process. Here, one would obtain a sample suspected of containing *Marburg* virus or its antigens, and contact the sample with an antibody that binds *Marburg* virus or components thereof, followed by detecting and quantifying the amount of immune complexes formed under the specific conditions. In terms of antigen detection, the biological sample analyzed may be any sample that is suspected of containing *Marburg* virus or *Marburg* virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *Marburg* virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the *Marburg* virus or *Marburg* virus antigen is added to the wells. After binding and washing to remove non-specifically bound immune complexes, the bound antigen may be detected. Detection may be achieved by the addition of another anti-*Marburg* virus antibody that is linked to a detectable label. This type of ELISA is a simple "sandwich ELISA." Detection may also be achieved by the addition of a second anti-*Marburg* virus antibody, followed by the addition of a third antibody that has binding affinity for the second antibody, with the third antibody being linked to a detectable label.

In another exemplary ELISA, the samples suspected of containing the *Marburg* virus or *Marburg* virus antigen are immobilized onto the well surface and then contacted with the anti-*Marburg* virus antibodies of the disclosure. After binding and washing to remove non-specifically bound immune complexes, the bound anti-*Marburg* virus antibodies are detected. Where the initial anti-*Marburg* virus antibodies are linked to a detectable label, the immune complexes may be detected directly. Again, the immune complexes may be detected using a second antibody that has binding affinity for the first anti-*Marburg* virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of *Marburg* virus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors proposes the use of labeled *Marburg* virus monoclonal antibodies to determine the amount of *Marburg* virus antibodies in a sample. The basic format would include contacting a known amount of *Marburg* virus monoclonal antibody (linked to a detectable label) with *Marburg* virus antigen or particle. The *Marburg* virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules;

pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further embodiments, the present disclosure concerns immunodetection kits for use with the immunodetection methods described above. As the antibodies may be used to detect *Marburg* virus or *Marburg* virus antigens, the antibodies may be included in the kit. The immunodetection kits will thus comprise, in suitable container means, a first antibody that binds to *Marburg* virus or *Marburg* virus antigen, and optionally an immunodetection reagent.

In certain embodiments, the *Marburg* virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the *Marburg* virus or *Marburg* virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Donor.

The donor was an otherwise healthy adult woman who contracted *Marburg* virus (MARV) infection in 2008 following exposure to fruit bats in the Python Cave in Queen Elizabeth National Park, Uganda. The donor's clinical course was documented previously (CDC, 2009). Peripheral blood from the donor was obtained in 2012, four years after the illness, following informed consent. The study was approved by the Vanderbilt University Institutional Review Board.

Viruses.

MARV strain 200702854 Uganda (MARV-Uganda) was isolated originally from a subject designated "Patient A" during the outbreak in Uganda in 2007 (CDC, 2009; Towner et al., 2009) and underwent 4 passages in Vero E6 cells. MARV strain Musoke (MARV-Musoke) was isolated during the outbreak in Kenya in 1980 (Smith et al., 1982) and passaged 5 times in Vero E6 cells. MARV strain 200501379 Angola (MARV-Angola) was isolated during the outbreak in Angola in 2005 (Towner et al., 2006) and passaged 3 times in Vero E6 cells. MARV Ravn virus (Ravn) was isolated from a patient in 1987 in Kenya (Johnson et al., 1996) and passaged 4 times in Vero E6 cells. All strains of MARV were obtained originally from the Special Pathogens Branch, U.S. Centers for Disease Control (CDC) and deposited at the World Reference Center of Emerging Viruses and Arboviruses (WRCEVA) housed at UTMB. The recombinant Ebola Zaire strain Mayinga (EBOV) to expressing eGFP was generated in the inventors' laboratory by reverse genetics (Lubaki et al., 2013; Towner et al., 2005) from plasmids provided by the Special Pathogens Branch at CDC and passaged 3 times in Vero E6 cells. For analysis of antibody binding by ELISA, viruses were gamma-irradiated with the dose of $5\times10^6$ rad. The recombinant VSV in which the VSV GP protein was replaced with that of MARV strain Musoke (VSV/GP-Musoke) or EBOV strain Mayinga (Garbutt et al., 2004) were provided by Dr. Thomas Geisbert (UTMB) and Dr. Heinz Feldmann (NIH), respectively; a similar virus with GP from MARV (strain 200702854 Uganda) was constructed as described below. All work with EBOV and MARV was performed within the Galveston National Laboratory BSL-4 laboratories.

The inventors used a mouse-adapted strain of MARV for testing the effect of mAbs in vivo. The mouse-adapted Ci67 strain of *Marburg* virus (Warfield et al., 2007) was provided by Dr. Sina Bavari (U.S. Army Medical Research Institute of Infectious Diseases, Fort Detrick, Md.) and amplified by a single passage in Vero-E6 cells.

Generation of a Chimeric Strain of VSV in which VSV G Protein was Replaced with the GP Protein of MARV Strain Uganda (VSV/GP-Uganda).

The plasmid pVSV-XN2 carrying cDNA of the full-length VSV anti-genome sequence and the support plasmids pBS-N, pBS-L and pBS-P encoding the internal VSV proteins under control of the T7 promoter were kindly provided by Dr. John Rose (Yale University). The plasmid pC-T7, encoding the T7 polymerase, was kindly provided by Dr. Yoshihiro Kawaoka (University of Wisconsin). For generation of the VSV/GP-Uganda construct, Vero E6 cell monolayers were inoculated with MARV strain 200702854 and total cellular RNA was isolated and reverse-transcribed. MARV GP ORF was PCR-amplified from cDNA using forward primer 5'-CATGTACGACGCGTCAACATGAGGACTA-3' (SEQ ID NO: 1) and reverse primer 5'-TCTAGCAG CTCGAGCTATCCAATATATTTAGTAAAGATACGACAA-3' (SEQ ID NO: 2; underlined are MluI and XhoI endonuclease sites, respectively; italicized are the start and the end of MARV GP ORF—direct and complementary sequences, respectively). To replace VSV G with MARV GP, the resulting PCR-product was cloned into pVSV-XN2 using the unique MluI and XhoI endonuclease sites located between the VSV G gene-start and gene-end signals and flanking its ORF, resulting in the plasmid pVSV/GP-Uganda. To recover the recombinant virus, $1\times10^6$ BSR-T7 cells, kindly provided by Dr. Ursula Buchholz (U.S. National Institute of Allergy and Infectious Diseases), were transfected with the following plasmids: pVSV/GP-Uganda, 5 μg; pBS-N, 1.5 μg; pBS-P, 2.5 μg; pBS-L, 1 μg; pC-T7, 5 μg. After 48 hours, transfected BSR-T7 cells were collected with a cell scraper and transferred, along with the supernates, to Vero E6 cell monolayers for amplification of the recovered VSV/GP-Uganda.

Generation of Human Hybridomas Secreting Monoclonal Antibodies (mAbs).

Peripheral blood mononuclear cells (PBMCs) from the donor were isolated with Ficoll-Histopaque by density gradient centrifugation. The cells were cryopreserved immediately and stored in the vapor phase of liquid nitrogen until use. Previously cryopreserved samples were thawed, and 10 million PBMCs were plated into 384-well plates (Nunc #164688) using: 17 mL of cell culture medium (ClonaCell-HY Medium A, Stemcell Technologies #03801), 8 μg/mL of the TLR agonist CpG (phosphorothioate-modified oligodeoxynucleotide ZOEZOEZZZZZOEEZOEZZZT (SEQ ID NO: 3), Invitrogen), 3 μg/mL Chk2 inhibitor (Sigma #C3742), 1 μg/mL cyclosporine A (Sigma #C1832) and 4.5 mL of clarified supernate from cultures of B95.8 cells (ATCC VR-1492) containing Epstein-Barr virus (EBV). After 7 days, cells from each 384-well culture plate were expanded into four 96-well culture plates (Falcon #353072) using cell culture medium containing 8 μg/mL CpG, 3 μg/mL Chk2i and 10 million irradiated heterologous human PBMCs (Nashville Red Cross) and incubated for an additional four days. Plates were screened for MARV antigen-specific antibody-secreting cell lines using enzyme-linked immunosorbent assays (ELISAs). Cells from wells with supernates reacting in a MARV antigen ELISA were fused with HMMA2.5 myeloma cells using an established electrofusion technique (Yu et al., 2008). After fusion, hybridomas were resuspended in medium containing 100 μM hypoxanthine, 0.4 μM aminopterin, 16 μM thymidine (HAT Media Supplement, Sigma #HO262) and 7 μg/mL ouabain (Sigma #03125) and incubated for 18 days before screening hybridomas for antibody production by ELISA.

Human mAb and Fab Production and Purification.

After fusion with HMMA2.5 myeloma cells, hybridomas producing MARV-specific antibodies were cloned biologically by two rounds of limiting dilution and by single-cell fluorescence-activated cell sorting. After cloning, hybridomas were expanded in post-fusion medium (ClonaCell-HY Medium E, STEMCELL Technologies #03805) until 50% confluent in 75-$cm^2$ flasks (Corning #430641). For antibody production, cells from one 75-$cm^2$ flask were collected with a cell scraper and expanded to four 225-$cm^2$ flasks (Corning #431082) in serum-free medium (Hybridoma-SFM, Gibco #12045-076). After 21 days, supernates were clarified by centrifugation and sterile filtered using 0.2-μm pore size filter devices. HiTrap Protein G or HiTrap MabSelectSure columns (GE Healthcare Life Sciences #17040501 and #11003494 respectively) were used to purify antibodies from filtered supernates. Fab fragments were generated by papain digestion (Pierce Fab Preparation Kit, Thermo Scientific #44985) and purified by chromatography using a two-column system where the first column contained protein G resin (GE Healthcare to Life Sciences #29048581) and the second column contained either anti-kappa or anti-lambda antibody light chain resins (GE Healthcare Life Sciences #17545811 and #17548211 respectively).

Expression and Purification of MARV and EBOV GPs.

Angola strain MARV GP ectodomains, containing the mucin-like domain (MARV GP) or lacking residues 257-425 of the mucin-like domain (MARV GPΔmuc), were used to screen supernates of transformed B cells and human hybridomas separately. Recombinant proteins for Ravn strain cleaved GP, EBOV Mayinga strain GP, EBOV Mayinga strain GPΔmuc and EBOV Mayinga strain cleaved GP were designed and expressed similarly. Large-scale production of recombinant GP or GPΔmuc was performed by transfection of *Drosophila* Schneider 2 (S2) cells with modified pMTpuro vectors, followed by stable selection of transfected cells with 6 μg/mL puromycin. Secreted GP ectodomain expression was induced with 0.5 mM $CuSO_4$ for 4 days. Proteins were engineered with a modified double strep tag at the C terminus (enterokinase cleavage site followed by a strep tag/linker/strep tag) to facilitate purification using Strep-Tactin resin (Qiagen #2-1201). Proteins were purified further by Superdex 200 size exclusion chromatography in 10 mM Tris, 150 mM NaCl, pH 7.5 (1×TBS).

Lysates of MARV-Infected Cells.

Lysates were prepared as previously described (Ksiazek et al., 1999). Briefly, Vero E6 cell monolayers in 850 $cm^2$ roller bottles were inoculated with approximately $10^6$ PFU MARV or EBOV and incubated at 37° C. until partial destruction of monolayer occurred (approximately 9-10 days). Cell monolayers were detached using 3 mm glass beads, and cell suspensions were centrifuged at 16,000×g for 10 min at 4° C. Supernates were discarded, cell pellets were resuspended in 10× excess of borate buffer saline (10 mM $Na_2B_4O_7$, 150 mM NaCl, pH 9.0), and centrifuged at 16,000×g for 10 min at 4° C. Supernates were discarded, cell pellets were resuspended in cold 1% Triton X-100 (Fisher Scientific) in borate buffer saline, vortexed and gamma-irradiated on dry ice at $5\times10^6$ rad. The lysates were sonicated with a 600 W Tekmar Sonic Disruptor TM600 (Tekmar) using a cuphorn sonicator at maximum power setting and 50% duty cycle for 10 min, centrifuged at 16,000×g and the supernates aliquoted.

Screening ELISA.

ELISA plates were coated with lysates of MARV infected cells (diluted 1:1,000 in Dulbecco phosphate buffered saline, DPBS) or recombinant MARV GP or MARV GPΔmuc proteins (20 μg in 10 mL DPBS per plate) and incubated at 4° C. overnight. Plates were blocked with 100 μL of blocking solution/well for 1 h. Blocking solution consisted of 10 g powdered milk, 10 mL of goat serum, 100 mL of 10×DPBS, and 0.5 mL of Tween-20 mixed to a 1 L final volume with distilled water. The presence of antibodies bound to the GP was determined using goat anti-human IgG horseradish peroxidase conjugated secondary antibodies (Southern Biotech #2040-05, 1:4,000 dilution) and 1-Step Ultra TMB-ELISA substrate (Thermo Scientific #34029), with optical density read at 450 nM after stopping the reaction with 1M HCl.

Half Maximal Effective Concentration (EGO Binding Analysis.

MARV or EBOV GPs, MARV or EBOV GPΔmuc, or Ravn or EBOV cathepsin-cleaved GPs were coated onto 384-well plates (Thermo Scientific Nunc #265203) in DPBS at 2 μg/mL overnight, then antigen was removed and plates were blocked with blocking solution made as above. Antibodies were applied to the plates at a concentration range of 1.5 μg/mL to 270 ng/mL (Binding Groups #1, #2 and 3A) and 0.1 μg/mL to 10 ng/mL (Binding Group #3B) using three-fold serial dilutions. The presence of antibodies bound to the GP was determined using goat anti-human IgG alkaline phosphatase conjugate (Meridian Life Science #W99008A, 1:4,000 dilution) and p-nitrophenol phosphate substrate tablets (Sigma #S0942), with optical density read at 405 nM after 120 minutes. A non-linear regression analysis was performed on the resulting curves using Prism version 5 (GraphPad) to calculate $EC_{50}$ values.

MARV and EBOV Neutralization Experiments.

Dilutions of mAbs in triplicate were mixed with 150 PFU of MARV or EBOV expressing eGFP in MEM containing 10% FBS (HyClone), 50 μg/mL gentamicin (Cellgro #30-005-CR) with or without 5% guinea pig complement (MP Biomedicals #642836) in a total volume of 0.1 mL, and incubated for 1 hour at 37° C. for virus neutralization. Following neutralization, virus-antibody mixtures were placed on monolayers of Vero E6 cells in 24-well plates, incubated for 1 hour at 37° C. for virus adsorption, and overlayed with MEM containing 2% FBS and 0.8% methylcellulose (Sigma-Aldrich #M0512-1KG). After incubation for 5 days, medium was removed, cells were fixed with 10% formalin (Fisher Scientific #245-684), plates were sealed in plastic bags and incubated for 24 hours at room temperature. Sealed plates were taken out of the BSL-4 laboratory according to approved SOPs, and monolayers were washed three times with phosphate buffered saline. Viral plaques were immunostained with the serum of rabbits that had been hyperimmunized with MARV, or with a mAb against EBOV, clone 15H10 (BEI Resources #NR-12184). Alternatively, following virus adsorption, monolayers were covered with MEM containing 10% FBS and 1.6% tragacanth (Sigma-Aldrich #G1128). After incubation for 14 days, medium was removed, cells were fixed with 10% formalin, plates were sealed in plastic bags, incubated for 24 hours at room temperature, and taken out of the BSL-4 laboratory as above. Fixed monolayers were stained with 10% formalin containing 0.25% crystal violet (Fisher Scientific #C581-100), and plaques were counted.

VSV-MARV and VSV-EBOV Neutralization Tests.

Neutralization assays were performed in triplicate, as described above for MARV and EBOV. Following neutralization, virus-antibody mixtures were placed on monolayers of Vero E6 cells in duplicate, incubated for 1 hour at 37° C. for virus adsorption, and overlayed with MEM containing 2% FBS containing 0.9% methylcellulose. After incubation for 3 days, medium was removed, monolayers were fixed and stained with 10% formalin containing 0.25% crystal violet, and plaques were counted.

Generation and Sequencing of VSV/GP-Uganda Escape Mutants.

Vero E6 cell monolayers with two-fold dilutions of mAbs (12.5-200 μg/mL) added to the medium were inoculated with 200 PFU of recombinant VSV/GP-Uganda and incubated at 37° C. for 2-4 days. To determine which samples contained live virus, supernates were collected, virus was titrated in Vero E6 cell monolayers under methylcellulose overlay, monolayers were incubated at 37° C. for 3-4 days, and plaques were counted. Supernates with the highest concentrations of mAbs, which were found to contain live virus by plaque titration, were incubated in presence of serially diluted mAbs followed by titration of virus as above. The procedure was performed a total of three times. Escape mutant viruses harvested after the third passage were cloned biologically by plaque purification. For biological cloning, Vero E6 cell monolayers in 24-well plates were inoculated with dilutions of the escape mutant viruses in the presence of the corresponding mAbs (200 μg/mL of MR72 or 100 μg/mL of MR78) and covered with 0.7% low melting temperature SeaPlaque agarose (Lonza #50100). Monolayers were incubated at 37° C. for 6 days, plaques were visualized with 0.01% neutral red aqueous solution (Electron Microscopy Sciences), picked, resuspended in medium and transferred to Vero E6 cell monolayers in 24-well plates in presence of the corresponding mAbs (200 μg/mL of MR72 or 100 μg/mL of MR78) for virus propagation. In 2-5 days, based on the extent of CPE observed, virus was harvested, and cells were dissolved in Trizol reagent (Life Technologies 315596018). Total cellular RNA was extracted and reverse-transcribed and amplified by PCR with the primers described above for generation of a chimeric strain of VSV. Two overlapping fragments covering MARV GP ORF were PCR-amplified from cDNA using forward primer 5'-CATGTACGACGCGTCAACATGAGGACTA-3' (SEQ ID NO: 4) and reverse primer 5'-ACTAAGCCCTGCTGCCAGGT-3' (SEQ ID NO: 5) or forward primer 5'-ACAACAATGTACCGAGGCAA-3' (SEQ ID NO: 6) and reverse primer 5'-TCTAGCAGCTCGAGCTATCCAATATATTTAGTAAAGATACGACAA-3' (SEQ ID NO: 7), and the nucleotide sequences of the GP ORFs were determined using standard procedures.

Analysis of Growth Kinetics of VSV/GP-Uganda Escape Mutant Viruses.

Vero E6 cell monolayers in 24-well plates were inoculated in triplicate with VSV/GP-Uganda escape mutants or non-mutated virus at an MOI of 0.00025 PFU/cell in the presence of varying concentrations of the corresponding mAbs. Aliquots of medium were collected every 12 hours and frozen for titration at a later time. Titration of virus in aliquots was performed as above, without adding antibodies to the culture medium.

Biolayer Interferometry Competition Binding Assay.

Biotinylated GP or GPΔmuc (EZ-Link® Micro NHS-PEG4-Biotinylation Kit, Thermo Scientific #21955) (1 μg/mL) was immobilized onto streptavidin-coated biosensor tips (ForteBio #18-5019) for 2 minutes. After measuring the baseline signal in kinetics buffer (KB: 1×PBS, 0.01% BSA and 0.002% Tween 20) for two minutes, biosensor tips were immersed into the wells containing primary antibody at a concentration of 100 μg/mL for 10 minutes. Biosensors then were immersed into wells containing competing mAbs at a concentration of 100 μg/mL for 5 minutes. The percent binding of the competing mAb in the presence of the first mAb was determined by comparing the maximal signal of competing mAb applied after the first mAb complex to the maximal signal of competing mAb alone. MAbs were judged to compete for binding to the same site if maximum binding of the competing mAb was reduced to <30% of its un-competed binding. MAbs were considered non-competing if maximum binding of the competing mAb was >70% of its un-competed binding. A level of 30-70% of its un-competed binding was considered intermediate competition.

Sequence Analysis of Antibody Variable Region Genes.

Total cellular RNA was extracted from clonal hybridomas that produced MARV antibodies, and RT-PCR reaction was performed using mixtures of primers designed to amplify all heavy chain or light chain antibody variable regions. The generated PCR products were purified and cloned into the pJet 1.2 plasmid vector (Thermo Scientific, #K1231) for sequence analysis. The nucleotide sequences of plasmid DNAs were determined using an ABI3700 automated DNA sequencer. Heavy chain or light chain antibody variable region sequences were analyzed using the IMGT/V-Quest program (Brochet et al., 2008; Giudicelli et al., 2011). The analysis involved the identification of germline genes that were used for antibody production, location of complementary determining regions (CDRs) and framework regions (FRs) as well as the number and location of somatic mutations that occurred during affinity maturation.

Statistical Analysis.

$EC_{50}$ values for neutralization were determined by finding the concentration of mAb at which a 50% reduction in plaque counts occurred after incubation of virus with neutralizing antibody. A logistic curve was fit to the data using the count as the outcome and the log-concentration as the predictor variable. The results of the model then were transformed back to the concentration scale. Results are presented as the concentration at the dilution that achieve a 50% reduction from challenge control with accompanying 95% confidence intervals. Each antibody was treated as a distinct analysis in a Bayesian non-linear regression model.

Sample Preparation for EM Studies.

A Ravn strain MARV GP mucin-deleted construct (GPΔmuc) was produced by stable cell line expression in *Drosophila* S2 cells, as described above. Human Fab proteins for MARV-specific antibodies were generated as described above. Fabs were added in molar excess to GPΔmuc and allowed to incubate overnight at 4° C. Complexes then were purified by Superdex 200 size exclusion chromatography in TBS.

Electron Microscopy and Sample Preparation.

A 4 μL aliquot of each complex that had been diluted to a concentration of −0.03 μg/mL with TBS buffer was placed for 15 seconds onto carbon-coated 400 Cu mesh grids that had been plasma cleaned for 20 s (Gatan), blotted off on the edge of the grid, then immediately stained for 30 s with 4 μL of 2% uranyl formate. The stain was blotted off on the edge of the grid and the grid was allowed to dry. Data were automatically collected with Leginon (Carragher et al., 2000; Potter et al., 1999; Suloway et al., 2005) using a FEI Tecnai F20 electron microscope operating at 120 keV with an electron dose of 30 $e^-/Å^2$ and a magnification of 52,000× that resulted in a pixel size of 2.65 Å at the specimen plane when collected with Tietz CMOS 4 k×4 k CCD camera. Particle orientations appeared to be generally isotropic and images were acquired at a constant defocus value of −1.0 μm at 0° stage tilt.

Image Processing of Protein Complexes.

Particles were picked automatically using DoG Picker (34) and placed into a particle stack using the Appion software (Lander et al., 2009). Reference-free 2D class averages were generated with the Xmipp clustering 2D alignment software (van Heel et al., 1996) and sorted into an initial 300 classes. Non-GP particles were removed and the stack was further sub-classified into classes with ~100 particles per class in order to generate the final particle stack used for the reconstruction. Various numbers of class averages were chosen to create initial models using EMAN2 common lines software (Tang et al., 2007). A model that best matched its projected classes was then used for refinement against the raw particle stack, imposing C3 symmetry, and the reconstruction was generated with 10 rounds of refinement and increasingly smaller angular sampling rates with EMAN2 (Tang et al., 2007). All model fitting and manipulation was completed using UCSF Chimera (Pettersen et al., 2004).

In Vivo Testing.

The animal protocol for testing of mAbs in mice was approved by the Institutional Animal Care and Use Committee of the University of Texas Medical Branch at Galveston. Seven-week-old BALB/c mice (Harlan) were placed in the ABSL-4 facility of the Galveston National Laboratory. Groups of mice at 5 animals per group were injected with individual mAbs by the intraperitoneal route twice: one h prior and 24 h after MARV challenge, using 100 μg per treatment. Untreated animals served as controls. For the challenge, mice were injected with 1,000 PFU of the mouse-adapted MARV strain Ci67 by the intraperitoneal route. Animals were weighed and monitored daily over the three-week period after challenge. Once animals were symptomatic, they were examined twice per day. The disease was scored using the following parameters: dyspnea (possible scores 0-5), recumbency (0-9), unresponsiveness (0-5), and bleeding/hemorrhage (0-5); the individual scores for each animal were summarized.

In Vivo Mouse Studies.

The in vivo protective activity of the mAbs was tested in a murine model using mouse-adapted MARV strain Ci67 (Warfield et al., 2007; 2009). Inoculation of mice with MARV Ci67 causes clinical symptoms and lethal disease, although typically with less than 100% lethality (Warren et al., 2014). Seven-week-old BALB/c mice were challenged with 1,000 plaque-forming unit (PFU) of Ci67 by the IP route. Twenty-four hours later, mice were injected with 100 μg of an antibody by the IP route. The typical symptoms of the disease included progressive loss of weight, dyspnea, recumbency and unresponsiveness, followed by death of euthanasia of moribund animals.

Independent Variable Scores were as follows:

Body Weight:

0—Normal

1—<10% weight loss

2—10-15% weight loss, eating

3—>20% weight loss, not eating

Appearance:

0—Normal

1—Lack of grooming

2—Coat rough, possible nasal and or ocular discharge

3—Coat very rough, abnormal posture, pupils enlarged

Clinical Signs:

0—Normal

1—Small change of potential significance

2—Temperature rise 1-2, 30% rise in respiratory/heart rates

3—Temperature change >2, 25% rise in respiratory/heart rates (or markedly reduced/shallow)

Unprovoked Behavior:

0—Normal

1—Minor changes

2—Abnormal behavior, less mobile, less alert, inactive when activity expected

3—Unsolicited vocalization, extreme self-mutilation

Behavior Response to External Stimuli:

0—Normal

1—Minor exaggerated response

2—Moderate abnormal response

3—Violent response

Total score is the sum of the above. The overall score will be tabulated and used to help interpret our assessment of each animal. A total score of 3 or less will be considered normal; 4-7 will indicate some evidence of pain or discomfort. Any animal reaching a score of 7 or greater will be strongly considered for early euthanasia.

Example 2—Results

Isolation of Monoclonal Antibodies (mAbs).

The inventors tested plasma of a MARV survivor previously infected in Uganda for the 50% neutralization activity against the Uganda strain of MARV and found a serum neutralizing titer of 1:1,010. To generate human hybridoma cell lines secreting mAbs to MARV, the inventors screened supernatants from EBV-transformed B cell lines derived from the survivor for binding to several recombinant forms of MARV GP or to irradiated cell lysates prepared from MARV-infected cell cultures. They fused transformed cells from B cell lines producing MARV-reactive Abs to the MARV antigens with myeloma cells and generated 51 cloned hybridomas secreting MARV-specific human mAbs. Thirty-nine of these mAbs were specific to the MARV GP, while 12 bound to infected-cell lysate but not to GP; these latter mAbs were shown in secondary screens to bind to MARV internal proteins (NP, VP35 or VP40; data not shown). Analysis of the Ab heavy- and light-chain variable domain sequences revealed that all MARV-specific mAbs were encoded by unique Ab genes.

Neutralization Activity.

Figure 6:
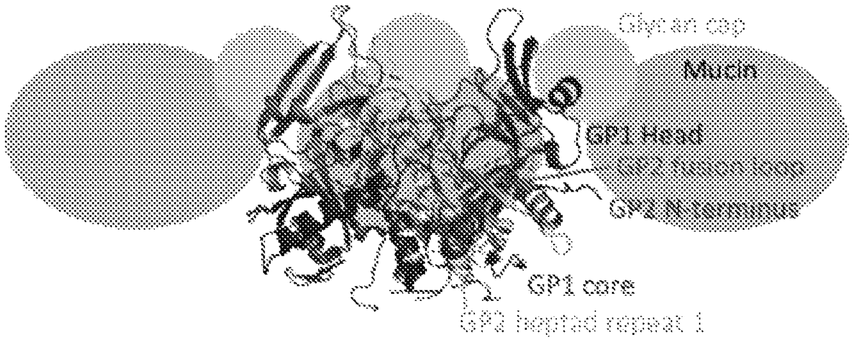
FIG. 6. General Schematic of the *Marburg* Virus Glycoprotein Trimer with Its Major Structural Domains and Features. Related to the FIGS. 2A-D.
Figure 7:
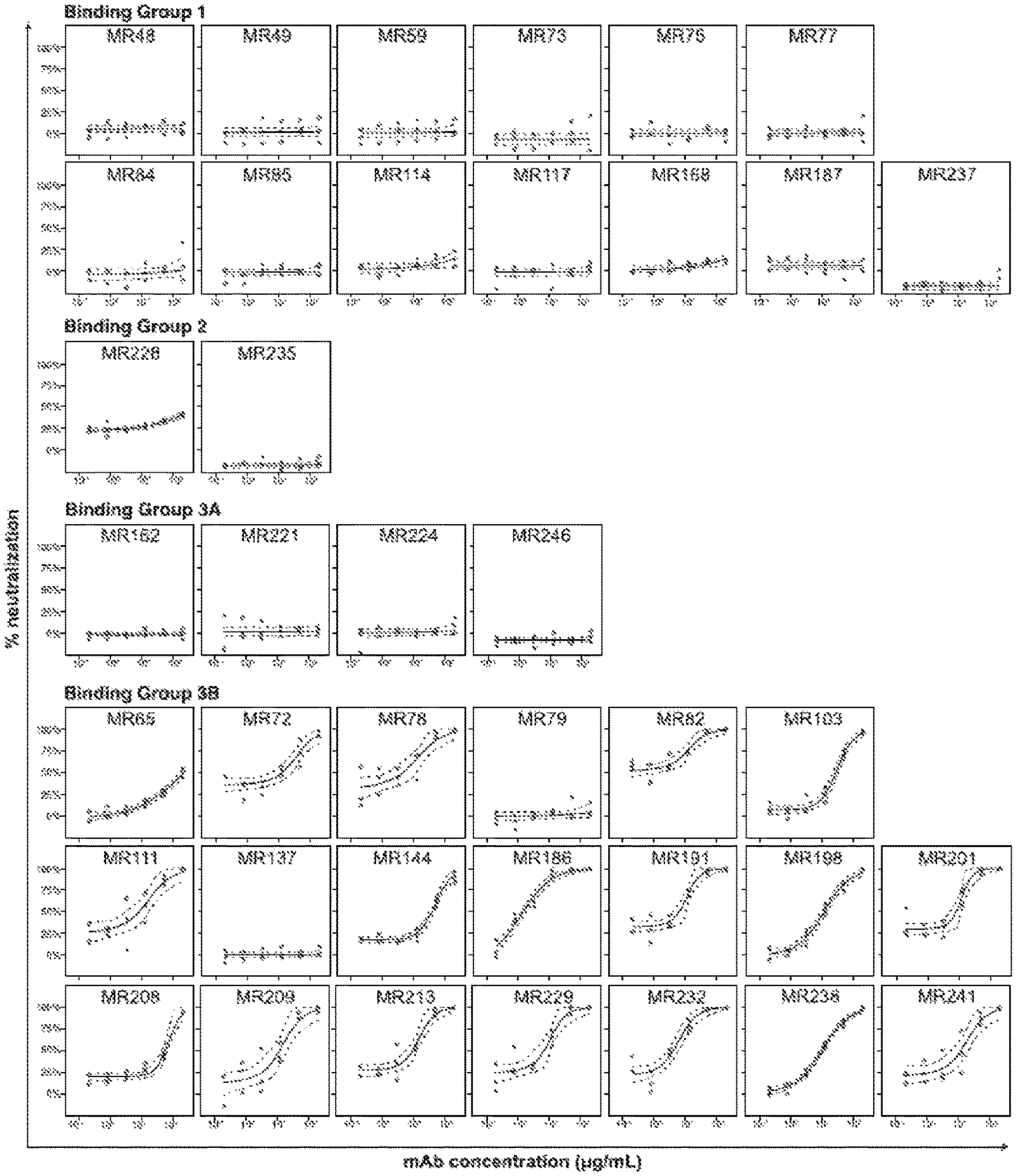
FIG. 7. Neutralization Activity of MARV GP-Specific mAbs against VSV/GP-Uganda. Related to FIGS. 1A-D. Red circles represent percent neutralization relative to control at different antibody concentrations. Logistic curves are indicated by solid lines, and 95% confidence intervals are indicated by dashed lines.
Figure 8:
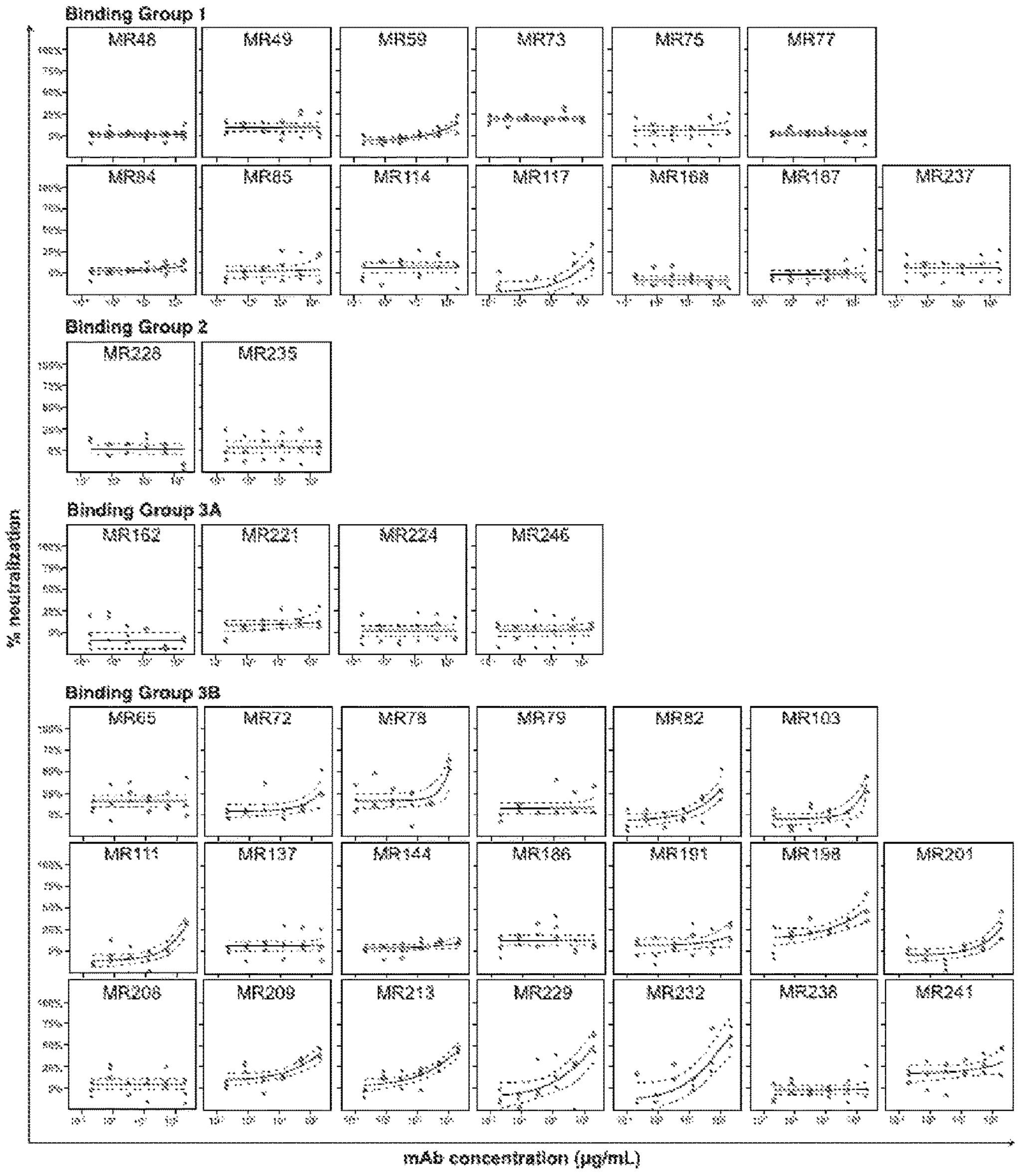
FIG. 8. Neutralization Activity of MARV GP-Specific mAbs against MARV-Uganda. Related to FIGS. 1A-D. Red circles represent percent neutralization relative to control at different antibody concentrations. Logistic curves are indicated by solid lines, and 95% confidence intervals are indicated by dashed lines.

To evaluate the inhibitory activity of the mAbs, the inventors first performed in vitro neutralization studies using a chimeric vesicular stomatitis virus with MARV GP from Uganda strain on its surface (VSV/GP-Uganda). Eighteen of the 39 MARV GP-specific mAbs exhibited neutralization activity against VSV/GP-Uganda (FIGS. 1A and 1C; FIGS. 7 and 9A-B). Of those 18 nAbs, 9 displayed strong ($IC_{50}$<10 μg/mL), 8 nAbs displayed moderate ($IC_{50}$: 10-99 μg/mL) and one displayed weak ($IC_{50}$: 100-1,000 μg/mL) neutralizing activity against VSV/GP-Uganda. The inventors also tested the neutralization potency of all nAbs that bound to MARV GP in a plaque reduction assay using live MARV-Uganda virus. Of 18 Abs that neutralized VSV/GP-Uganda, 10 Abs exhibited neutralizing activity against MARV-Uganda (FIGS. 1A and 1C; FIGS. 8 and 9A-B). These data suggest that VSV/GP, often used to study neutralizing potency of Abs because of its BSL-2 containment level, is more susceptible to Ab-mediated neutralization than live MARV. This difference is likely explained by the significantly lower copy number of MARV GP molecules that incorporate into VSV particles compared with the large number of GP molecules on the surface of Filovirus filaments (Beniac et al., 2012; Thomas et al., 1985). Comparison of MARV neutralizing and non-neutralizing antibodies at concentration up to 1.6 mg/mL revealed dose-dependent activity of those mAbs that neutralized. The neutralization activity of nAbs was not enhanced by the presence of complement (data not shown). As expected, the inventors did not detect neutralizing activity for any of the 12 Abs specific to MARV NP, VP35 or VP40 proteins.

Recognition of Varying Forms of GP.

Figure 10:
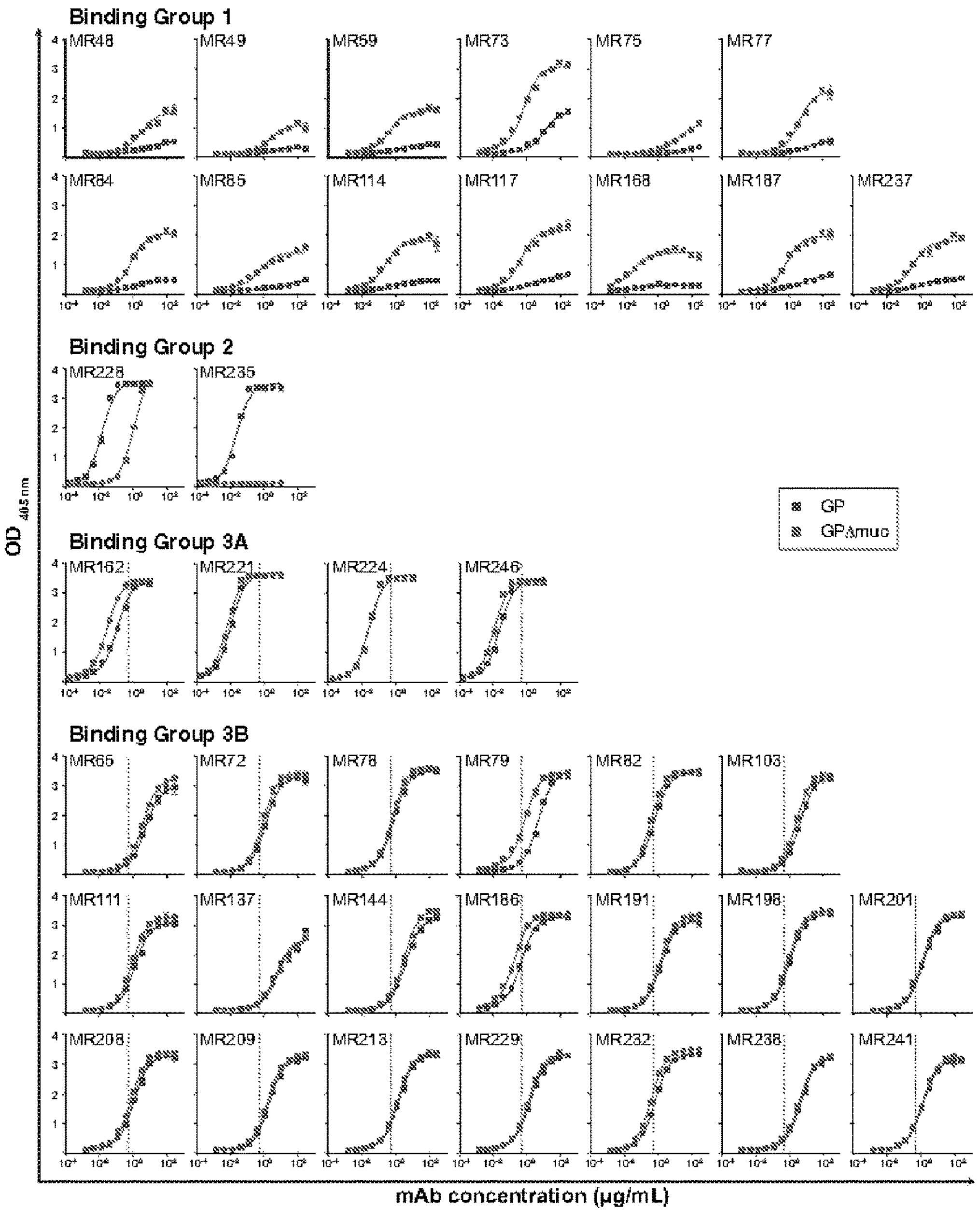
FIG. 10. Binding Patterns of MARV GP-Specific Antibodies. Related to FIGS. 1A-D. Antibodies were segregated into four Binding Groups based on the binding to MARV GP (blue squares) or MARV GPDmuc (green squares). Binding was categorized based on the values at the highest antibody concentration tested and half maximal effective concentration ($EC_{50}$) as shown below.

To characterize the binding of isolated Abs to recombinant MARV GPs, the inventors performed binding assays using either a recombinant MARV GP ectodomain containing the mucin-like domain (MARV GP) or a recombinant GP lacking residues 257-425 of the mucin-like domain (MARV GPΔmuc). Based on $OD_{405}$ values at the highest Ab concentration tested (Emax) and 50% effective concentration ($EC_{50}$), the inventors divided the MARV-GP-specific Abs into four major groups, based on binding phenotype (designated Binding Groups 1, 2, 3A and 3B; FIG. 1B and FIG. 10). Binding Group 1 mAbs had an Emax to GP<2 (i.e., these mAbs never exhibited a maximal binding level to MARV GP); Binding Group 2 mAbs had an Emax to GP>2, with $EC_{50}$ for GP<$EC_{50}$ for GPΔmuc (i.e., these mAbs bound to the mucin-like domain or glycan cap); Binding Group 3 had an Emax to GP>2, with $EC_{50}$ for GP $EC_{50}$ for GPΔmuc (i.e., these mAbs bound equally well to full-length and mucin-deleted forms of GP), with the Group 3A mAbs having an $EC_{50}$ for GP<0.5 μg/mL and the Group 3B mAbs having an $EC_{50}$ for GP>0.5 μg/mL (suggesting that, as a class, the Group 3B mAbs possess a lower steady state $K_D$ of binding to GP than Group 3A mAbs).

Abs that lacked neutralization activity against VSV/GP-Uganda or MARV-Uganda fell principally into Binding Groups 1, 2, 3A. Interestingly, all VSV/GP-Uganda nAbs displayed a unique binding pattern and segregated into Binding Group 3B (FIG. 1C). It was interesting that while both mAbs from Groups 3A and 3B bound equally well to the full-length MARV GP and to the GPΔmuc, $EC_{50}$ values for nAbs from Binding Group 3B were higher than those for non-neutralizing Abs from Group 3A.

Competition-Binding Studies.

To determine whether mAbs from distinct binding groups targeted different antigenic regions on the MARV GP surface, the inventors performed a competition-binding assay using a real-time biosensor. They tested 18 MARV nAbs from Binding Group 3B, four Abs from Binding Group 3A and one Ab from Binding Group 2 in a tandem blocking assay in which biotinylated GPΔmuc was attached to a streptavidin biosensor. Abs from Group 1 and the two non-neutralizing Abs from Binding Group 3B did not bind to biotinylated GPΔmuc in the competition assay and were excluded from the analysis. While non-neutralizing Abs from Binding Groups 2 and 3A did not prevent binding of the Binding Group 3B nAbs to GPΔmuc, all nAbs blocked binding of each of the other nAbs to the antigen and segregated into a single competition-binding group (FIG. 1D). These data suggested that all of the nAbs target a single major antigenic region on the MARV GP surface.

Electron Microscopy Studies of Antigen-Antibody Complexes.

To determine the location of the antigenic region targeted by MARV nAbs, the inventors performed negative stain single-particle electron microscopy (EM) studies using complexes of GPΔmuc with Fab fragments of seven nAbs from Binding Group 3B. The EM reconstructions clearly showed that Fab fragments for all seven nAbs bind at the top of the GP in or near the NPC1 protein receptor-binding site (FIGS. 2A-B). The binding pattern of these Abs could be divided further into two major groups based on their relative angle of approach to the GP head domain. MAbs MR72, MR78, MR201 and MR82 bound toward the top and side of GP1 at a shallow angle relative to the central three-fold axis, while mAbs MR191, MR111 and MR198 bound at a steeper angle toward the top of GP1 (FIGS. 2C-D). When the inventors compared $IC_{50}$ values for nAbs that bound in the two binding poses, they did not detect a significant difference in neutralization potency based on the angle of approach (FIG. 1C).

Antibody Neutralization Escape Mutant Viruses.

As an additional strategy to determine residues on MARV GP involved in binding to nAbs, the inventors generated VSV/GP-Uganda variant viruses that escaped neutralization, and then they determined the sequence of the GP of those mAb escape viruses. Vero E6 cells were inoculated with VSV/GP-Uganda in the presence of MR72 or MR78 nAbs. Two escape mutant viruses were isolated: virus variant VSV/GP-72.5 contained three missense mutations in the MARV GP gene (N129S in the putative NPC1 receptor-binding site, S220P in the glycan cap and P455L in the mucin-like domain) and virus variant VSV/GP-78.1 possessed missense mutation C226Y in the glycan cap (FIG. 3A). Consistent with the EM data, six out of seven nAbs tested displayed a higher level of neutralization activity against the wild-type VSV/GP-Uganda than to the VSV/GP-72.5 or VSV/GP-78.1 escape mutant viruses, suggesting these nAbs recognize MARV GP in a similar fashion (FIG. 3B). MAb MR198 exhibited equal neutralization potency against wild-type VSV/GP-Uganda or the two escape mutant viruses (FIG. 3B). As all nAbs segregated into one competition group (FIG. 1D), bound the MARV GP at the NPC1 receptor-binding site (FIGS. 2A-D) and displayed a similar profile of neutralization of escape mutant viruses (FIG. 3B), the inventors propose that blocking of MARV GP binding to NPC1 is the principal mechanism of MARV neutralization by these naturally-occurring human Abs. This model is supported by the data in the accompanying paper (Hashiguchi et al., 2015) showing that MR78 inhibits binding of NPC1 domain C to MARV GP.

Cross-Reactive Binding of MARV Antibodies with EBOV GP.

It is surprising that human MARV nAbs recognize the putative NPC1 protein receptor-binding site on GP, since previous studies suggested that the NPC1 protein receptor-binding site on EBOV GP may be obscured from Ab binding by the presence of the highly glycosylated glycan cap and mucin-like domain (Lee et al., 2008). To determine whether the MARV nAbs the inventors isolated also could bind in a cross-reactive manner to the EBOV GP receptor-binding site, and they performed ELISA binding assays using three recombinant forms of MARV and EBOV GPs: full-length GP ectodomain containing the glycan cap and mucin-like domain (designated MARV or EBOV GP), ectodomains lacking residues 257-425 (MARV) or 314-462 (EBOV) of the mucin-like domain (designated MARV or EBOV GPΔmuc) and cleaved GP ectodomains enzymatically treated to remove the mucin-like domain and glycan cap (designated MARV or EBOV GPcl). Three of the MARV nAbs, designated MR78, MR111 and MR191, recognized the EBOV GPcl that lacked the glycan cap and mucin-like domain (FIG. 4A). Remarkably, the MARV nAb MR72 bound all three forms of both EBOV and MARV GPs with similar $EC_{50}$ and Emax values, indicating that its epitope, and the EBOV receptor-binding site which it likely overlaps, might be partially accessible for Ab binding even in the full-length form (FIG. 4A). The inventors tested the breadth of neutralization of MARV nAbs for filoviruses using a panel of different MARV and EBOV isolates. While multiple MARV Abs displayed neutralizing activity towards different MARV strains, MARV nAbs did not exhibit detectable neutralization activity against EBOV or VSV/EBOV (FIG. 4B). Structural analysis of MARV and EBOV GP in the accompanying paper (Hashiguchi et al., 2015) reveals that the glycan cap and mucin-like domain likely obscure the receptor-binding domain in EBOV but not MARV.

In Vivo Testing.

The inventors tested the in vivo protective activity of the mAbs in a murine model using mouse-adapted MARV strain Ci67 (Warfield et al., 2007; Warfield et al., 2009). Inoculation of mice with MARV Ci67 causes clinical disease, and in a proportion of animals causes lethal disease, although typically less than 100% lethality in mice (Warren et al., 2014). The inventors selected four of the mAbs among those with the lowest in vitro neutralization $IC_{50}$ values: MR72, MR82, MR213, and MR232. The $IC_{50}$ values in neutralization assays with MARV Uganda or mouse-adapted MARV strain Ci67 were comparable (within two-fold). Seven week-old BALB/c mice were injected with 100 μg of antibody by the IM route and challenged with 1,000 PFU of Ci67. Twenty four hours later, antibody treatment was repeated. By day 6, all five control (untreated) mice developed progressive loss of weight and symptoms of the disease, including dyspnea, recumbency and unresponsiveness, and on days 8 and 9, two animals were found dead and one animal was found moribund and euthanized. The remaining two animals demonstrated recovery by day 11. In contrast, all animals treated with any antibody survived and did not display the elevation of the disease score, with the exception of two animals treated with MR72, which showed a transient marginal loss of weight and increase of the disease score on days 6-9, which did not exceed 1 (FIG. 5). The observed level of protection was remarkable given the relatively modest in vitro neutralizing potency of the antibodies.

The inventors further tested the utility of two of the *Marburg* GP monoclonal antibodies for therapeutic effect in a fatal guinea pig challenge model (FIGS. 11A-B). MR78 or MR191 antibodies were expressed as recombinant full length IgG molecules in transgenic tobacco plants (*Nicotiana tabacum*) and purified (designated MR78-N or MR191-N) and used to treat guinea pigs challenged with guinea pig adapted Angola strain of *Marburg* virus (treatment with 10 mg per animal on day 4 post-infection) or challenged with guinea pig adapted Ravn strain of *Marburg* virus (treatment with 10 mg per animal on day 2 post-infection). In both cases, both antibodies mediated a therapeutic effect.

The inventors further tested the utility of one of the *Marburg* GP monoclonal antibodies for therapeutic effect in a fatal monkey challenge model (FIGS. 12A-B). MR191 antibody was expressed as recombinant full length IgG molecules in transgenic tobacco plants (*Nicotiana tabacum*) and purified (designated MR191-N) and used to treat macaques challenged with Angola or Ravn strain of *Marburg* virus (treatment on day 5 post-infection). For both challenge strains, the antibody mediated a therapeutic effect, as evidenced by decrease viral load and increased survival.

Example 3—Discussion

There is an obvious urgent need for prophylactic and therapeutic interventions for filovirus infections given the recurrence of MARV outbreaks including in October 2014 in Uganda and a massive outbreak of EBOV infections in West Africa in 2014. There is very little information about the structural determinants of neutralization on which to base the rational selection of antibodies, and for MARV there have been no reported human nAbs.

This study reveals that naturally occurring human MARV nAbs isolated from the B cells of a recovered donor principally target the MARV NPC1 protein receptor-binding site, suggesting that a major mechanism of MARV neutralization could be inhibition of binding to receptor. Remarkably, some of the isolated antibodies also bound to the EBOV GP. This mechanism of MARV neutralization was unexpected, because previous studies with EBOV showed that the putative receptor-binding domain on GP is obscured on the surface of virions by the presence of the glycan cap and mucin-like domain, only becoming exposed following cleavage by cathepsin in the endosome. These studies suggest that the configuration of the MARV GP differs significantly from that of EBOV GP because the receptor-binding domain must be accessible for immune recognition on MARV GP. Indeed, determination of the structure of the MARV GP and structural analysis of the interaction of mAb MR78 with MARV and EBOV GP molecules shows this to be the case (see accompanying paper, Hashiguchi et al., 2015).

The information obtained from these studies can be used to inform development of new therapeutics and structure-based vaccine designs against filoviruses. Furthermore, as these nAbs are fully human and exhibit inhibitory activity, they might be useful as a component of a prophylactic or therapeutic approach for filovirus infection and disease. The challenge studies using a murine model here show clear evidence of in vivo activity and suggest additional preclinical studies in other species such as guinea pigs and macaques are warranted. Their ability to bind a broad range of MARV isolates indicates they may offer detection of or efficacy against new viral strains yet to emerge. Although some of these mAbs bind to certain forms of EBOV GP, these antibodies are not likely to be effective against natural Ebola infection because the EBOV receptor-binding site is obscured on the viral surface. However, such mAbs might neutralize EBOV if they could be delivered to the endosome where the EBOV receptor-binding site is exposed following GP cleavage.

TABLE 1

NUCLEOTIDE SEQUENCES FOR ANTIBODY VARIABLE REGIONS

| Clone | Variable Region Sequence | SEQ ID NO: |
|---|---|---|
| >MR65_VH | gaggtgcagctgttggagtctggggggaggc<br>ttggtacagcctggggggtccctgagactc<br>tcctgtgcagcctctggattcacctttagc<br>agctatgccatgagctgggtccgccaggct<br>ccagggcaggggctggagtgggtctcaggt<br>attagtgctactggtggtaacacatactac<br>ccagactccgtgaagggccgattcaccatc<br>tccagagacaattccaagaacacgctgtac<br>ctgcaaatgaacagcctgagagccgaggac<br>acggccgtatattactgtgcgagaccatta<br>caatttttgacctggacgacccctggggcc<br>agggaaccctggtcaccgtctcctca | 8 |
| >MR65_VL | gaaattgtgagacacagtctccggccaccc<br>tgtctttgtctccaggggaaagagccaccc<br>tctcctgcagggccagtcagagtgttaaca<br>acttcttagcctggtaccaacagaaacctg<br>gccagcctcccaggctcctcatctatgatg<br>caaccaacagggccactggcatcccagcca<br>ggacagtggcagtgggtctgggacagactt<br>cactctcaccatcagcagcctagagcctga<br>agattttgcagtttatcactgtcagcaccg<br>tagcaactggccctcgatcaccttcggcca<br>agggacacgactggagattaaa | 9 |
| >MR72_VH | cagctgcagctgcaggagtcgggcccagga<br>ctggtgaagccttcggagaccctgaacctc<br>tcctgcactgtctctggtgactccatcaac<br>aatactaattactactgggcctggatccgc<br>cagcccccagggaaggggctggagtacatt | 10 |

TABLE 1-continued

NUCLEOTIDE SEQUENCES FOR ANTIBODY VARIABLE REGIONS

| Clone | Variable Region Sequence | SEQ ID NO: |
|---|---|---|
| | gggagtatctattatagtgggagcacctac<br>tacaacccgtccctcaagagccgagtcacc<br>atgtccgtagacgcgtccaagaaccagttc<br>tccctgaggctgagctctgtgaccgccgca<br>gacacggctgtgtattactgtgcgacacac<br>cccacactggggggcttagtattactgtggt<br>tcggggcaaactttgaccactggggccagg<br>gaaccctggtcaccgtctcctca | |
| >MR72_VL | caggctgtggtgacgcagccgccctcagtg<br>tctggggccccaggccagagggtcaccatc<br>tcctgcactgggagcagctccaacatcggg<br>gcaaattatgatgtacactggtaccagcag<br>cttccagggacagcccccaaactcctcatg<br>tatagtaacactaatcggccctcaggggtc<br>cctgaccgattctctggctccaagtctggc<br>acttcagcctccctggccatcactgggctc<br>caggctgaggatgaggctgattattactgc<br>cagtcctatgacaacagcctgaacagttgg<br>gtgttcggcggagggacccagctgaccgtc<br>cta | 11 |
| >MR78_VH | cagctgcagctgcaggagtcgggcccagga<br>ctggtgaagccttcggagaccctgtccctc<br>acctgcactgtgtctggtggctccatcagc<br>agtagtagttactactggggctggatccgc<br>cagcccccagggaaggggctggagtggatt<br>gggagtgtctattatagtgggggcgcctcc<br>tacaacccgtccctgaagagtcgagccacc<br>atatccgtagacacgtccaagaaccagttc<br>tccctgaacctggactctgtgagcgccgca<br>gacacggctatatattactgtgcgagtatt<br>tatggttcagggaccttttactactacttc<br>tacatggacgtctggggcaaagggtccacg<br>gtcaccgtctcctca | 12 |
| >MR78_VL | gacatccagatgacccagtctccatcctcc<br>ctgtctgcatctgtaggagacagagtcacc<br>atcacttgccaggcgagtcaggtcattagc<br>aactatttaaattggtatcaacagaaacca<br>gggaaagcccctaagctcctgatctacgac<br>acatccaatttgaaaacaggggtcccatca<br>aggttcagtggaagtggatctgggacagat<br>tttactttcaccatcagcagcctgcagcct<br>gaagatattgcaacatattattgtcaacaa<br>tatgaaaatctccagttcactttcggccct<br>gggaccaaggtggatatcaaa | 13 |
| >MR82_VH | caggtccagcttgtgcagtctggggctgag<br>gtgaagaagcctggggcctcagtgaaggtc<br>tcctgcaaggcttctggacacaccttcact<br>acctatgctatccattgggtgcgccaggcc<br>cccggacaagggcttgagtggatgggatgg<br>atcaaccctgacaatgataacacagaatat<br>tcacagaagttccagggcagagtcaccatt<br>accagggacacatccgcgagcacagcctac<br>atggagctgagcagcctgatatctgaggac<br>acggctgtgttttactgtgcgagcgcttct<br>tacactttttggagtggttattatagtggt<br>ctggactactggggccagggaaccctggtc<br>accgtctcctca | 14 |
| >MR82_VL | gaaattgtgttgacgcagtctccaggcacc<br>ctgtctagtctccaggggaaagagccaccc<br>tctcctgcagggccagtcagagtgttagca<br>tcaactacttagcctggtaccagcagaaac<br>ctggccaggctcccaggctcctcatctatg<br>gtgcatccagcagggccactggcatcccag<br>acaggacagtggcagtgggtctgggacaga<br>cttcactctcaccatcagcagactggagcc<br>tgaagattttgcagtgtattactgtcagca<br>gtatggtagctcacctccgtggactttcgg<br>ccctgggaccaaggtggatatcaaa | 15 |

TABLE 1-continued

NUCLEOTIDE SEQUENCES FOR ANTIBODY VARIABLE REGIONS

| Clone | Variable Region Sequence | SEQ ID NO: |
|---|---|---|
| >MR103_VH | caggttcagctggtgcagtctggagctgag<br>gtgaagaagcctggggcctcagtgaaggtc<br>tcctgcaaggcttctggttatacctttagc<br>aactatggtatcagctgggtgcgacaggcc<br>cctggacaagggcttgagtggatgggatgg<br>gtcaacacttataatggtaacacatactat<br>gctcagagccttcagggcagagtcaccatg<br>accacagacacatccacgagcacagcctac<br>atggagctgaggagcctgakatctgacgac<br>acggccgtgtacttttgtgcgagagatcac<br>cccattacgattatggagtgattattcttg<br>gggagccaacaacctggggccagggaaccc<br>tggtcaccgtctcctca | 16 |
| >MR103_VL | gaaatagtgatgacgcagtctccagccacc<br>ctgtctgtgtctccaggggaaagagccacc<br>ctctcctgcagggccagtcagagtgttaac<br>agcaacttagcctggtaccagcagaaacct<br>ggccaggctcccaggctcctcatctatggt<br>gcatccaccagggccactggtatcccagcc<br>aggttcagtggcagtgggtctgggacagag<br>ttcactctcaccatcagcagcctgcagtct<br>gaagattagaagtttattactgtcagcagt<br>ataataactggccccggacgttcggccaag<br>ggaccaaggtggatatcaaa | 17 |
| >MR111_VH | caggtgcagctgcaggagtcgggcccagga<br>ctggtgaagccttcggagaccctgtccctc<br>acctgcactgtctctggtgactccatcaat<br>aattattactggagctggatccggcagccc<br>ccagggaagggactggagtggattgggtat<br>atctattacagtaataccaactacaacccc<br>tccctcaaaagtcgagtcaccatatcagta<br>gacacgtccaagaaccagactccctgaggc<br>tgagctctgtgaccgctgcggacacggccg<br>tgtattactgtgcgagatctccattatttt<br>ggacggggagttcttacctcgcctgatcac<br>tagacttttggggccagggaaccctg | 18 |
| >MR111_VL | cagtctgccctgactcagcctgcctccgtg<br>tctgggtctcctggacagtcgatcaccatc<br>tcctgcactggaaccagcagtgatgaggga<br>gttatgaccttgtctcctggtaccaacagc<br>acccaggcaaagcccccaaactcatgcttt<br>atgagggcactaagcggccctcaggggttt<br>ctaatcgcttctctggctccaagtctggca<br>acacggcctccctgacaatctctgggctcc<br>aggctgaggacgaggctgattattactgct<br>gctcatatgcaggtggtagcactaggtatt<br>cggcggagggacccaggtgaccgtccta | 19 |
| >MR144_VH | caggtgcagctgcaggagtcgggcccagga<br>ctggtgaagccttcggagaccctgtccctc<br>acctgcactgtctctggtgactccataagt<br>agatactactggagttggatccggcagccc<br>ccagggaagggactggagtggattgggtat<br>ctctattacagtgggagtaccgactacaac<br>ccctccctcaagagtcgagtcaccatttca<br>gtagacacgtccaagaaccagttctccctg<br>aatctgacctctgtgaccgctgcggacacg<br>gccgtgtattactgtgcgagaggatcctcc<br>cggggtataggagtggtgtcgcactggttc<br>gacccctggggccagggaacc | 20 |
| >MR144_VL | tcctatgtgctgactcagccaccctcggtg<br>tcagtggccccaggacagacggccagaatc<br>acctgtgggggatccaacatgggatataaa<br>agtgtgcagtggtaccagcagaggccaggc<br>caggcccctgtgctggtcgtctatgatgat<br>accgaccggccctcagggatccctgagcga<br>ttctctggctccaactctggggccacggcc<br>accctgaccatcagcagtgtcgaagccggg<br>gatgaggccgactattactgtcaggtgtgg<br>gatagtagtagcgatcatcatgtggtattc<br>ggcggagggacccaggtgaccgtccta | 21 |

TABLE 1-continued

NUCLEOTIDE SEQUENCES FOR ANTIBODY VARIABLE REGIONS

| Clone | Variable Region Sequence | SEQ ID NO: |
|---|---|---|
| >MR186_VH | caggtgcagctgcaggagtcgggcccagga<br>ctggtgaagccttcggagaccctgtccctc<br>tcctgcactgtctctggtggctccatcagt<br>ggttactactggagctggatccggcagccc<br>ccagggaagggactggagtggattgggtat<br>atctatcacagtgggagtcccaactacaac<br>ccctccctcaagagtcgagtcaccatttca<br>gtagacacgtccaagaaccagttctccctg<br>aggctgagctctgtgaccgccgcagacacg<br>gccatgtattactgtgcgagaactgcttat<br>acggtgggttttacgcctactactacttgg<br>atgtctggggcagagggaccaccctgtccc<br>tctcctgc | 22 |
| >MR186_VL | gacatccagatgacccagtctccatcctcc<br>ctgtctgcatctgtaggggacagagtcacc<br>atcacttgccaggcgagtcacgacattagc<br>aactatttaaattggtatcagcaaaaacca<br>ggcaaagcccctaagctcctgatctacgat<br>gcatccaatttggaaacgggggtcccatca<br>aggttcagtggagctggatctgggacagat<br>tttactttcaccatcagcagcctgcagcct<br>gaagatgagcaacatattactgtcaagtat<br>atgataatctcctcttcacttcgg | 23 |
| >MR191_VH | cagctgcagctgcaggagtcgggcccagga<br>ctggtgaagccttcggagaccctgtccctc<br>acctgcactgtctctggtgtctccatcagc<br>gataatagttattactggggctggatccgc<br>cagcccccagggaagggcctggagtggatt<br>gggactatctcttatagtgggaacacctac<br>tacaacccgtccctcaagagtcgagtcagc<br>atatccggagacacgtccaagcaccagctc<br>tccctgaaggtgagctctgtgaccgccgca<br>gacacggctgtctattactgtgcgagacag<br>cggatagtatcaggatagtggagtggctat<br>caaaatttgactactggggccaggggaccc<br>tggtcaccgtctcctca | 24 |
| >MR191_VL | cagtctgtgctgacgcagccgccctcagtg<br>tctggggccccagggcagagggtcaccatc<br>tcctgcactgggagcagctccaacatcggg<br>gcaggttttgatgtacactggtaccagcaa<br>cttccaggaacagcccccaaactcctcatc<br>tatgataacaacaatcggccctcaggggtc<br>cctgaccgattctctggctccaagtctggc<br>acctcagcctccctggccatcactgggctc<br>caggctgaggatgaggctgattattactgc<br>cagtcctatgacaccagcctgagtggtccc<br>gtggtgttcggcggagggaccaagctgacc<br>gtccta | 25 |
| >MR198_VH | caggtgcagctgcaggagtcgggcccagga<br>ctggtgaagccttcacagaccctgtccctc<br>tcctgcactgtctctggtggctccatcagc<br>agtgatagttactactggaactggatccgc<br>cagcacccagggaagggcctggagtggatt<br>gggtacgtctattatagtgggagcaccaac<br>tacaacccgtccctcaagagtcgagttatc<br>atatcactagacacgtctaagaaccagttc<br>tccctgaagctgaactctgtgactgccgcg<br>gacacggccgtgtattactgtgcgagagcc<br>gattattatggttcagggagtttcttctac<br>tactaccacatggacgtctggggcaaaggg | 26 |
| >MR198_VL | gacatccagatgacccagtctccttccacc<br>ctgtctgcatctgtaggagacagagtcacc<br>atcacttgccgggccagtcagagtatttat<br>acctggttggcctggtatcagcagaaacca<br>gggaaagcccctaagctcctgatccataag<br>tcgtctagtttagaaagtggggtcccttca<br>aggtIcagcggcagtggatctgggacagaa<br>ttcactctcaccatcagcagcctgcagcct<br>gatgattttgcgacttattactgccaccag<br>tattatgtttatccttgcacgtcggcc | 27 |

TABLE 1-continued

NUCLEOTIDE SEQUENCES FOR ANTIBODY VARIABLE REGIONS

| Clone | Variable Region Sequence | SEQ ID NO: |
|---|---|---|
| >MR201_VH | cagctgcagctgcaggagtcgggcccagga<br>ctggtgaagccttcggagactctgtactca<br>gttgcgctgtctctggtggctccatcgccg<br>gtagcactcactactggggctggatccgcc<br>agccccccagggaaggggctggagtggattg<br>ggagtatctctgaaagtgggagcacctacc<br>acaatccgtccctcaagagtcgagtcacca<br>tatccgtggacacgtccaaaaattacttct<br>ccctgaacttgagctctgtgaccgccgcag<br>acacggctgtgtattactgtgcgagaatag<br>tgggtcaatctggtacctttatctactact<br>attacgccatggacgtctggggcacaggga<br>ccctggtcaccgtctcctca | 28 |
| >MR201_VL | gacatccagttgacccagtctccatccttc<br>ctgtctgcatctgtaggagacagagtcacc<br>atcacttgccgggccagtcagggcattagt<br>agttatttagcctggtatcagcaaaaacca<br>gggaaagcccctaagctcctgatctatgct<br>gcctccactttgcaacgtggggtcccatca<br>aggttcagcggcagtggatctgggacagag<br>ttcactctcacaatcagcagcctgcagcct<br>gaagactctgcaacttattactgtcaacag<br>cttaatagttatctcgcgctcattttcggc<br>ggagggacc | 29 |
| >MR208_VH | caggtgcagctgcaggagtcgggcccagga<br>ctggtgaagccttcggagaccctgtccctc<br>acctgcagtgtctctggtgactccgtcagc<br>agtggtgattactattggagctggctccgg<br>cagcccccccgggaagggactggagtggatt<br>ggctatatctattacagtggggccaccaac<br>tacaacccctccctcaagagtcgagtcacc<br>atttcactagacacgtccaagaaccagttc<br>tccctgaaactgacctctgtgaccgctgcg<br>gacacggccgtctattactgtgcgagagaa<br>cgggcgggattttggagtggttattttt<br>gaagattggggccagggaacc | 30 |
| >MR208_VL | gacatccagatgacccagtctccatcctcc<br>ctgtctgcatctgtaggagacagagtcacc<br>atttttttgccgggcaagtcagagcattggc<br>acctatttaagaggtatcaacagaaaccag<br>ggaaagcccctaaggtcttgatctatgcta<br>catccaatttgcaaagtggggtcccatcaa<br>ggttcagtggcagtggatctgggacagaat<br>tcactctcaccatcagcagtctgcaacctg<br>aagattttgcaacatactactgtcaacaaa<br>gtaggacattcggccaagggaccaaggtgg<br>atatgaaa | 31 |
| >MR209_VH | cagctgcagctgcaggagtcgggcccagga<br>ctggtgaagccttcggagaccctgtccctc<br>acctgcactgtcgctggtggccccatcacc<br>agtaataattactactggggctggatccgt<br>cagtccccagggaaggggctggagtggatt<br>gggagtgtttattatagtgggaacacctac<br>tataatccgtccatcaagactcgagtcacc<br>atgtccgtggacacgtcgaagagccagttc<br>tccctaaaactgaactccgtgaccgccgca<br>gacacggctgtctattactgtgcgagacag<br>tttaggcttttacaatttgtggagtggcta<br>caccactttgactcctggggcccagggaac | 32 |
| >MR209_VL | tcctatgtgctgactcagccaccctcggtg<br>tcagtggccccaggacagacggccaggatt<br>ccctgtgggggcaatgatattgcgaataaa<br>cgtgtgcactggtaccagcagaagccaggc<br>caggcccctatgctggtcgtctatgatgat<br>ggcgaccggccctcagggatccctgagcga<br>ttctctggctccaactctgggaacacggcc<br>accctgaccatcagccgggtcgaagccggg<br>gatgaggccgactattactgtcaggtgtgg<br>gaaaatagtagtgatctttgtgtggtattc<br>ggcggagggaccaagctgaccgtccta | 33 |
| >MR229_VH | gaggtgcagctggtggagtctgggggaggc<br>ttggtaaagccagggggtccctgagaatc<br>tcctgtgtaacttctggattcacctttggt<br>gattatgctatgagttggttccgccaggct<br>ccagggaaggggctggagtgggtaggtttc<br>attagaaacaaaggttatggtgggacaata<br>gattacgccgcgtctgtgaaaggcagattc<br>accatctcaagagatgattccaagagtatc<br>gcctatctgcaaatgaacagcctgaaaacc<br>gaggacacagccgtttattactgtaccgga<br>gtccgattgcattacgatttctggagtggt<br>tatgatgatgattcttttcatatatggggc<br>caagggacaatg | 34 |
| >MR229_VL | gatggtgtgatgactcagtctccactctcc<br>ctgcccgtcacccctggacagccggcctcc<br>atctcctgcaggtctactcaaagcctcgta<br>cacggagatggagacacctacttatattgg<br>tttcagcagaggccaggccaatctccaagg<br>cgcctaatttataaggtttctaatcgggac<br>tctggggtcccagacagattcagcggcagt<br>gggtcaggcactgatttcacactgaaaatc<br>agcagggtggaggctgaggatgttggggtt<br>tattactgcatgcaaagtacacactggcct<br>ccgacttttggccag | 35 |
| >MR232_VH | cagctgcagctgcaggagtcgggcccagga<br>ctggtgaagccttcggagaccctgtccctc<br>acctgcgctgtgtcaggtggctccatcagc<br>agtagtggttactgctggggctggatccgc<br>cagcccccagggaaggggctggagtggatc<br>gcgagtatctgctctagtgggaccacctac<br>ttcaattcgtccctcaagagtcgagtctcc<br>atatccatagacacgtccaggccccagttc<br>ttactgaacctgcgctctctgaccgccgca<br>gacacggctgtctactattgtgcgagacaa<br>agaatggagttacatttttttggagtggttg<br>taccttagactcctggggccagggaaccct<br>ggtcaccgtctcctca | 36 |
| >MR232_VL | gacatagtgatgacgcagtctccagccacc<br>ctgtctgtgtctccaggagagagagccacc<br>ctctcctgcagggccagtcagagtgttagc<br>agcaacttagcctggtaccagcagaaacct<br>ggccaggctcccaggctcctcatctctggt<br>gcatccactagggccactggtatcccagcc<br>agattcagtggcagtgggtctgggacagag<br>ttcactctcaccatcagcagcctgcagtct<br>gaagattttgcagtttattactgtcagcag<br>tatattaactggccgtgcagttttggccag<br>gggaccaaggtggatatcaaa | 37 |
| >MR238_VH | gaggtgcagctggtggagtctgggggaggc<br>ttggtccagcctgggggtccctgagactc<br>tcctgtgcagcctctggattcacctttagt<br>agttattggatgaactgggtccgccaggct<br>ccagggaaggggctggagtgggtggccaac<br>gtaaaggaagatggaagtaagaagtactat<br>gtggactctgtgaaggggcgattcaccatc<br>tccagagacaacgccaagaactctctgtat<br>ctgcaaatgaacagcctgagagtcgaggac<br>acggctctctattactgtgtgagaggagag<br>gattgtagtggtggaaggtgctcctcccta<br>tttttccgcagcactactttgactactgg<br>ggcccagggaac | 38 |
| >MR238_VL | gacatccagatgacccagtctccatcttcc<br>gtgtctgcatctgtaggagacagagtcacc<br>atcacttgtcgggcgagtcagggtattctc<br>aactggttagcctggtatcagcagaaacca<br>gggaaagcccctaaactcctgatctatgct<br>gcatccagtgtacaaagtggggtcccatca<br>aggttcagcggcagtggatctggcacagat<br>ttcaccctcaccattagcagcctgcagcct | 39 |

TABLE 1-continued

NUCLEOTIDE SEQUENCES FOR ANTIBODY VARIABLE REGIONS

| Clone | Variable Region Sequence | SEQ ID NO: |
|---|---|---|
| | gacgattttgcaacttactattgtcagcaa<br>actaacagtttccctctcactttcgccgga<br>gggaccaaggtggagatcaaa | |
| >MR241_VH | caggtgcagctgcaggagtcgggccccgga<br>ctggtgaagccttcggagaccctgtccctc<br>acctgcactgtctctggtgcctccatcagt<br>ggtaacttctggagctggatccggcagccc<br>ccagggaagggactggaatatattggttat<br>atgtctgacattgggaccaccaactacagc<br>ccctccctcaagagtcgagtcaccatttca<br>gtagacacgtccaagaaccagttctccctg<br>aatctgacctctgtgaccgctgcggacgcg<br>gccgtgtattactgtgcgagacttgtagca<br>gtgcctggtttcttctatcactactacatg<br>gacgtctggggwgaggggaccctggtcacc<br>gtctcctca | 40 |
| >MR241_VL | gacatygtgatgacccagtctccatcttcc<br>gtgtctgcatctgtaggagacagagtcacc<br>atcacttgtcgggcgagtcagggtattagt<br>ggctggttggcctggtatcagcagaaacca<br>gggaaagcccctaagctcctgatctatgct<br>acatccactttgcaaagtggggtcccgtca<br>aggttcagcggcagtgaatctgggacagct<br>ttcactctcaccatcagcagcctgcagcct<br>gaagattttgcaacttactattgtcaacag<br>gctaacagtttccctctcactttcggcgga<br>gggaccaaggtggagatcaaa | 41 |
| >MR228_VH | caggtgcagctggtggagtctgggggaggc<br>gtggtccagcctgggggtccctgaggatc<br>tcctgtgcagccgctggattcacctttagt<br>agaagtggcatgcactgggtccgccaggct<br>ccaggcaaggggctggagtgggtggcagtc<br>atttcatatgacggaaatactgaacactat<br>gcagactccatggagggccgagtcaccgtc<br>tccagagacaactccaacaacacgctgtac<br>ctgcaaatgaacagcctgagagcgggggac<br>acggctgtgtattattgtgcgaaagatcga<br>catactacagggagtaattataatggcgga<br>ctcttggaccactggggccagggaaccctg<br>gtcaccgtctcctca | 42 |
| >MR228_VL | gaaaccgtgatgacccagtctccagactcc<br>ctggctgtgtctctgggcgagagggccacc<br>atcaactgcaagtccagccagagtgtttta<br>cacagctccaagaatagaaactacttggct<br>tggtaccagcagaagccaggacagcctcct<br>aagttgctcatttactgggcatctacccgg<br>gaatccggggtccctgaccgcttcagtggc<br>agcgggtctgggacagatttcactctcacc<br>atcagcagcctgcaggctgaagatgtggca<br>ctttattactgtcagcaatattatactagt<br>ccgctgactttcggccaagggacacgactg<br>gagattaaa | 43 |

MR# indicates the particular monoclonal antibody
VH indicates the antibody heavy chain variable region
VL indicated the antibody light chain variable region

TABLE 2

PROTEIN SEQUENCES FOR ANTIBODY VARIABLE REGIONS

| Clone | Variable Sequence |
|---|---|
| >MR65_VH | EVQLLESGGGLVQPGGSLRLSCAASGFTFSSYAMS<br>WVRQAPGQGLEWVSGISATGGNTYYPDSVKGRFTI<br>SRDNSKNTLYLQMNSLRAEDTAVYYCARPLQFLTW<br>FDPWGQGTLVTVSS (SEQ ID NO: 44) |

TABLE 2-continued

PROTEIN SEQUENCES FOR ANTIBODY VARIABLE REGIONS

| Clone | Variable Sequence |
|---|---|
| >MR65_VL | EIVLTQSPATLSLSPGERATLSCRASQSVNNFLAW<br>YQQKPGQPPRLLIYDATNRATGIPARFSGSGSGTD<br>FTLTISSLEPEDFAVYHCQHRSNWPSITFGQGTRL<br>EIK (SEQ ID NO: 45) |
| >MR72_VH | QLQLQESGPGLVKPSETLSLTCTVSGDSINNTNYY<br>WAWIRQPPGKGLEYIGSIYYSGSTYYNPSLKSRVT<br>MSVDASKNQFSLRLSSVTAADTAVYYCATHPTLGA<br>FVLLWFGANFDHWGQGTLVTVSS<br>(SEQ ID NO: 46) |
| >MR72_VL | QAVVTQPPSVSGAPGQRVTISCTGSSSNIGANYDV<br>HWYQQLPGTAPKLLMYSNTNRPSGVPDRFSGSKSG<br>TSASLAITGLQAEDEADYYCQSYDNSLNSWVFGGG<br>TQLTVL (SEQ ID NO: 47) |
| >MR78_VH | QLQLQESGPGLVKPSETLSLTCTVSGGSISSSSYY<br>WGWIRQPPGKGLEWIGSVYYSGGASYNPSLKSRAT<br>ISVDTSKNQFSLNLDSVSAADTAIYYCASIYGSGT<br>FYYYFYMDVWGKGSTVTVSS<br>(SEQ ID NO: 48) |
| >MR78_VL | DIQMTQSPSSLSASVGDRVTITCQASQVISNYLNW<br>YQQKPGKAPKLLIYDTSNLKTGVPSRFSGSGSGTD<br>FTFTISSLQPEDIATYYCQQYENLQFTFGPGTKVD<br>IK (SEQ ID NO: 49) |
| >MR82_VH | QVQLVQSGAEVKKPGASVKVSCKASGHTFTTYAIH<br>WVRQAPGQGLEWMGWINPDNDNTEYSQKFQGRVTI<br>TRDTSASTAYMELSSLISEDTAVFYCASASYTFWS<br>GYYSGLDYWGQGTLVTVSS (SEQ ID NO: 50) |
| >MR82_VL | EIVLTQSPGTLSLSPGERATLSCRASQSVSINYLA<br>WYQQKPGQAPRLLIYGASSRATGIPDRFSGSGSGT<br>DFTLTISRLEPEDFAVYYCQQYGSSPPWTFGPGTK<br>VDIK (SEQ ID NO: 51) |
| >MR103_VH | QVQLVQSGAEVKKPGASVKVSCKASGYTFSNYGIS<br>WVRQAPGQGLEWMGWVNTYNGNTYYAQSLQGRVTM<br>TTDTSTSTAYMELRSLXSDDTAVYFCARDHPITIF<br>GVIILGEPTTWGQGTLVTVSS<br>(SEQ ID NO: 52) |
| >MR103_VL | EIVMTQSPATLSVSPGERATLSCRASQSVNSNLAW<br>YQQKPGQAPRLLIYGASTRATGIPARFSGSGSGTE<br>FTLTISSLQSEDFEVYYCQQYNNWPRTFGQGTKVD<br>IK (SEQ ID NO: 53) |
| >MR111_VH | QVQLQESGPGLVKPSETLSLTCTVSGDSINNYYWS<br>WIRQPPGKGLEWIGYIYYSNTNYNPSLKSRVTISV<br>DTSKNQFSLRLSSVTAADTAVYYCARSPLFWFGEF<br>FSSPDHFDFWGQGTL (SEQ ID NO: 54) |
| >MR111_VL | QSALTQPASVSGSPGQSITISCTGTSSDVGSYDLV<br>SWYQQHPGKAPKLMLYEGTKRPSGVSNRFSGSKSG<br>NTASLTISGLQAEDEADYYCCSYAGGSTLVFGGGT<br>QVTVL (SEQ ID NO: 55) |
| >MR144_VH | QVQLQESGPGLVKPSETLSLTCTVSGDSISRYYWS<br>WIRQPPGKGLEWIGYLYYSGSTDYNPSLKSRVTIS<br>VDTSKNQFSLNLTSVTAADTAVYYCARGSSRGIGV<br>VSHWFDPWGQGT (SEQ ID NO: 56) |
| >MR144_VL | SYVLTQPPSVSVAPGQTARITCGGSNMGYKSVQWY<br>QQRPGQAPVLVVYDDTDRPSGIPERFSGSNSGATA<br>TLTISSVEAGDEADYYCQVWDSSSDHHVVFGGGTQ<br>VTVL (SEQ ID NO: 57) |
| >MR186_VH | QVQLQESGPGLVKPSETLSLSCTVSGGSISGYYWS<br>WIRQPPGKGLEWIGYIYHSGSPNYNPSLKSRVTIS<br>VDTSKNQFSLRLSSVTAADTAMYYCARTAYTVGFF<br>AYYYLDVWGRGTTLSLSC (SEQ ID NO: 58) |

TABLE 2-continued

PROTEIN SEQUENCES FOR ANTIBODY VARIABLE REGIONS

| Clone | Variable Sequence |
|---|---|
| >MR186_VL | DIQMTQSPSSLSASVGDRVTITCQASHDISNYLNWYQQKPGKAPKLLIYDASNLETGVPSRFSGAGSGTDFTFTISSLQPEDVATYYCQVYDNLLFTS (SEQ ID NO: 59) |
| >MR191_VH | QLQLQESGPGLVKPSETLSLSCTVSGVSISDNSYYWGWIRQPPGKGLEWIGTISYSGNTYYNPSLKSRVSISGDTSKHQLSLKVSSVTAADTAVYYCARQRIVSGFVEWLSKFDYWGQGTLVTVSS (SEQ ID NO: 60) |
| >MR191_VL | QSVLTQPPSVSGAPGQRVTISCTGSSSNIGAGFDVHWYQQLPGTAPKLLIYDNNNRPSGVPDRFSGSKSGTSASLAITGLQAEDEADYYCQSYDTSLSGPVVFGGGTKLTVL (SEQ ID NO: 61) |
| >MR198_VH | QVQLQESGPGLVKPSQTLSLSCTVSGGSISSDSYYWNWIRQHPGKGLEWIGYVYYSGSTNYNPSLKSRVIISLDTSKNQFSLKLNSVTAADTAVYYCARADYYGSGSFFYYYHMDVWGKG (SEQ ID NO: 62) |
| >MR198_VL | DIQMTQSPSTLSASVGDRVTITCRASQSIYTWLAWYQQKPGKAPKLLIHKSSSLESGVPSRFSGSGSGTEFTLTISSLQPDDFATYYCHQYYVYPCTSA (SEQ ID NO: 63) |
| >MR201_VH | QLQLQESGPGLVKPSETLFLSCAVSGGSIAGSTHYWGWIRQPPGKGLEWIGSISESGSTYHNPSLKSRVTISVDTSKNYFSLNLSSVTAADTAVYYCARIVGQSGTFIYYYYAMDVWGTGTLVTVSS (SEQ ID NO: 64) |
| >MR201_VL | DIQLTQSPSFLSASVGDRVTITCRASQGISSYLAWYQQKPGKAPKLLIYAASTLQRGVPSRFSGSGSGTEFTLTISSLQPEDSATYYCQQLNSYLALIFGGGT (SEQ ID NO: 65) |
| >MR208_VH | QVQLQESGPGLVKPSETLSLTCSVSGDSVSSGDYYWSWLRQPPGKGLEWIGYIYYSGATNYNPSLKSRVTISLDTSKNQFSLKLTSVTAADTAVYYCARERAGFLEWLFFEDWGQGT (SEQ ID NO: 66) |
| >MR208_VL | DIQMTQSPSSLSASVGDRVTIFCRASQSIGTYLSWYQQKPGKAPKVLIYATSNLQSGVPSRFSGSGSGTEFTLTISSLQPEDFATYYCQQSRTFGQGTKVDMK (SEQ ID NO: 67) |
| >MR209_VH | QLQLQESGPGLVKPSETLSLTCTVAGGPITSNNYYWGWIRQSPGKGLEWIGSVYYSGNTYYNPSIKTRVTMSVDTSKSQFSLKLNSVTAADTAVYYCARQFRLLQFVEWLHHFDSWGPGN (SEQ ID NO: 68) |
| >MR209_VL | SYVLTQPPSVSVAPGQTARIPCGGNDIANKRVHWYQQKPGQAPMLVVYDDGDRPSGIPERFSGSNSGNTATLTISRVEAGDEADYYCQVWENSSDLCVVFGGGTKLTVL (SEQ ID NO: 69) |
| >MR229_VH | EVQLVESGGGLVKPGGSLRISCVTSGFTFGDYAMSWFRQAPGKGLEWVGFIRNKGYGGTIDYAASVKGRFTISRDDSKSIAYLQMNSLKTEDTAVYYCTGVRLHYDFWSGYDDDSFHIWGQGTM (SEQ ID NO: 70) |
| >MR229_VL | DGVMTQSPLSLPVTPGQPASISCRSTQSLVHGDGDTYLYWFQQRPGQSPRRLIYKVSNRDSGVPDRFSGSGSGTDFTLKISRVEAEDVGVYYCMQSTHWPPTFGQ (SEQ ID NO: 71) |
| >MR232_VH | QLQLQESGPGLVKPSETLSLTCAVSGGSISSSGYCWGWIRQPPGKGLEWIASICSSGTTYFNSSLKSRVSISIDTSRPQFLLNLRSLTAADTAVYYCARQRMELHFLEWLFPFDSWGQGTLVTVSS (SEQ ID NO: 72) |
| >MR232_VL | DIVMTQSPATLSVSPGERATLSCRASQSVSSNLAWYQQKPGQAPRLLISGASTRATGIPARFSGSGSGTEFTLTISSLQSEDFAVYYCQQYINWPCSFGQGTKVDIK (SEQ ID NO: 73) |
| >MR238_VH | EVQLVESGGGLVQPGGSLRLSCAASGFTFSSYWMNWVRQAPGKGLEWVANVKEDGSKKYYVDSVKGRFTISRDNAKNSLYLQMNSLRVEDTALYYCVRGEDCSGGRCSSLFFPQHYFDYWGPGN (SEQ ID NO: 74) |
| >MR238_VL | DIQMTQSPSSVSASVGDRVTITCRASQGILNWLAWYQQKPGKAPKLLIYAASSVQSGVPSRFSGSGSGTDFTLTISSLQPDDFATYYCQQTNSFPLTFAGGTKVEIK (SEQ ID NO: 75) |
| >MR241_VH | QVQLQESGPGLVKPSETLSLTCTVSGASISGNFWSWIRQPPGKGLEYIGYMSDIGTTNYSPSLKSRVTISVDTSKNQFSLNLTSVTAADAAVYYCARLVAVPGFFYHYYMDVWGEGTLVTVSS (SEQ ID NO: 76) |
| >MR241_VL | DIVMTQSPSSVSASVGDRVTITCRASQGISGWLAWYQQKPGKAPKLLIYATSTLQSGVPSRFSGSESGTAFTLTISSLQPEDFATYYCQQANSFPLTFGGGTKVEIK (SEQ ID NO: 77) |
| >MR228_VH | QVQLVESGGGVVQPGGSLRISCAAAGFTFSRSGMHWVRQAPGKGLEWVAVISYDGNTEHYADSMEGRVTVSRDNSNNTLYLQMNSLRAGDTAVYYCAKDRHTTGSNYNGGLLDHWGQGTLVTVSS (SEQ ID NO: 78) |
| >MR228_VL | ETVMTQSPDSLAVSLGERATINCKSSQSVLHSSKNRNYLAWYQQKPGQPPKLLIYWASTRESGVPDRFSGSGSGTDFTLTISSLQAEDVALYYCQQYYTSPLTFGQGTRLEIK (SEQ ID NO: 79) |

MR# indicates the particular monoclonal antibody
VH indicates the antibody heavy chain variable region
VL indicated the antibody light chain variable region

TABLE 3

CDR HEAVY CHAIN SEQUENCES

| Antibody | CDRH1 | CDRH2 | CDRH3 |
|---|---|---|---|
| MR65 | GFTFSSYA (SEQ ID NO: 80) | ISATGGNT (SEQ ID NO: 81) | ARPLQFLTWFDP (SEQ ID NO: 82) |
| MR72 | GDSINNTNYY (SEQ ID NO: 83) | IYYSGST (SEQ ID NO: 84) | ATHPTLGAFVLLWFGANFDH (SEQ ID NO: 85) |
| MR78 | GGSISSSSYY (SEQ ID NO: 86) | VYYSGGA (SEQ ID NO: 87) | ASIYGSGTFYYYFYMDV (SEQ ID NO: 88) |
| MR82 | GHTFTTYA (SEQ ID NO: 89) | INPDNDNT (SEQ ID NO: 90) | ASASYTFWSGYYSGLDY (SEQ ID NO: 91) |

TABLE 3-continued

CDR HEAVY CHAIN SEQUENCES

| Antibody | CDRH1 | CDRH2 | CDRH3 |
|---|---|---|---|
| MR103 | GYTFSNYG (SEQ ID NO: 92) | VNTYNGNT (SEQ ID NO: 93) | ARDHPITIFGVIILGEPTT (SEQ ID NO: 94) |
| MR111 | GDSINNYY (SEQ ID NO: 95) | IYYSNT (SEQ ID NO: 96) | ARSPLFWFGEFFSSPDHFDF (SEQ ID NO: 97) |
| MR144 | GDSISRYY (SEQ ID NO: 98) | LYYSGST (SEQ ID NO: 99) | ARGSSRGIGVVSHWFDP (SEQ ID NO: 100) |
| MR186 | GGSISGYY (SEQ ID NO: 101) | IYHSGSP (SEQ ID NO: 102) | ARTAYTVGFFAYYYLDV (SEQ ID NO: 103) |
| MR191 | GVSISDNSYY (SEQ ID NO: 104) | ISYSGNT (SEQ ID NO: 105) | ARQRIVSGFVEWLSKFDY (SEQ ID NO: 106) |
| MR198 | GGSISSDSYY (SEQ ID NO: 107) | VYYSGST (SEQ ID NO: 108) | ARADYYGSGSFFYYYHMDV (SEQ ID NO: 109) |
| MR201 | GGSIAGSTHY (SEQ ID NO: 110) | ISESGST (SEQ ID NO: 111) | ARIVGQSGTFIYYYYAMDV (SEQ ID NO: 112) |
| MR208 | GDSVSSGDYY (SEQ ID NO: 113) | IYYSGAT (SEQ ID NO: 114) | ARERAGFLEWLFFED (SEQ ID NO: 115) |
| MR209 | GGPITSNNYY (SEQ ID NO: 116) | VYYSGNT (SEQ ID NO: 117) | ARQFRLLQFVEWLHHFDS (SEQ ID NO: 118) |
| MR229 | GFTFGDYA (SEQ ID NO: 119) | IRNKGYGGTI (SEQ ID NO: 120) | TGVRLHYDFWSGYDDDSFHI (SEQ ID NO: 121) |
| MR232 | GGSISSSGYC (SEQ ID NO: 122) | ICSSGTT (SEQ ID NO: 123) | ARQRMELHFLEWLFPFDS (SEQ ID NO: 124) |
| MR238 | GFTFSSYW (SEQ ID NO: 125) | VKEDGSKK (SEQ ID NO: 126) | VRGEDCSGGRCSSLFFPQHYFDY (SEQ ID NO: 127) |
| MR241 | GASISGNF (SEQ ID NO: 128) | MSDIGTT (SEQ ID NO: 129) | ARLVAVPGFFYHYYMDV (SEQ ID NO: 130) |
| MR228 | GFTFSRSG (SEQ ID NO: 131) | ISYDGNTE (SEQ ID NO: 132) | AKDRHTTGSNYNGGLLDH (SEQ ID NO: 133) |

TABLE 4

CDR LIGHT CHAIN SEQUENCES

| Antibody | CDRL1 | CDRL2 | CDRL3 |
|---|---|---|---|
| MR65 | QSVNNF (SEQ ID NO: 134) | DAT | QHRSNWPSIT (SEQ ID NO: 135) |
| MR72 | SSNIGANYD (SEQ ID NO: 136) | SNT | QSYDNSLNSWV (SEQ ID NO: 137) |
| MR78 | QVISNY (SEQ ID NO: 138) | DTS | QQYENLQFT (SEQ ID NO: 139) |
| MR82 | QSVSINY (SEQ ID NO: 140) | GAS | QQYGSSPPWT (SEQ ID NO: 141) |
| MR103 | QSVNSN (SEQ ID NO: 142) | GAS | QQYNNWPRT (SEQ ID NO: 143) |
| MR111 | SSDVGSYDL (SEQ ID NO: 144) | EGT | CSYAGGSTLV (SEQ ID NO: 145) |
| MR144 | NMGYKS (SEQ ID NO: 146) | DDT | QVWDSSSDHHVV (SEQ ID NO: 147) |
| MR186 | HDISNY (SEQ ID NO: 148) | DAS | QVYDNLLFT (SEQ ID NO: 149) |

TABLE 4-continued

CDR LIGHT CHAIN SEQUENCES

| Antibody | CDRL1 | CDRL2 | CDRL3 |
|---|---|---|---|
| MR191 | SSNIGAGFD (SEQ ID NO: 150) | DNN | QSYDTSLSGPVV (SEQ ID NO: 151) |
| MR198 | QSIYTW (SEQ ID NO: 152) | KSS | HQYYVYPCT (SEQ ID NO: 153) |
| MR201 | QGISSY (SEQ ID NO: 154) | AAS | QQLNSYLALI (SEQ ID NO: 155) |
| MR208 | QSIGTY (SEQ ID NO: 156) | ATS | QQSRT (SEQ ID NO: 157) |
| MR209 | DIANKR (SEQ ID NO: 158) | DDG | QVWENSSDLCVV (SEQ ID NO: 159) |
| MR229 | QSLVHGDGDTY (SEQ ID NO: 160) | KVS | MQSTHWPPT (SEQ ID NO: 161) |
| MR232 | QSVSSN (SEQ ID NO: 162) | GAS | QQYINWPCS (SEQ ID NO: 163) |

TABLE 4-continued

| CDR LIGHT CHAIN SEQUENCES | | | |
|---|---|---|---|
| Anti-body | CDRL1 | CDRL2 | CDRL3 |
| MR238 | QGILNW (SEQ ID NO: 164) | AAS | QQTNSFPLT (SEQ ID NO: 165) |
| MR241 | QGISGW (SEQ ID NO: 166) | ATS | QQANSFPLT (SEQ ID NO: 167) |
| MR228 | QSVLHSSKNRNY (SEQ ID NO: 168) | WAS | QQYYTSPLT (SEQ ID NO: 169) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Abe and Kufe, *Cancer Res.*, 49(11):2834-2839, 1989.
Ahmad et al., *Nat. Cell Biol.*, 9:1419-1427, 2007.
Allred et al., *Arch. Surg.*, 125(1), 107-113, 1990.
Atherton et al., *Biol. of Reproduction,* 32, 155-171, 1985. 95670519.1 70
Baldus et al., *Clin. Cancer Res.*, 10(8):2790-2796, 2004.
Beidler et al., *J. Immunol.*, 141(11):4053-4060, 1988.
Brown et al., *J. Immunol. Meth.*, 12; 130(1), :111-121, 1990.
Campbell, *In: Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109, 215-237, 1999.
Duraisamy et al., *Gene,* 373:28-34, 2006.
EP Application 125,023
EP Application 171,496
EP Application 173,494
EP Application 184,187
Gefter et al., *Somatic Cell Genet.*, 3:231-236, 1977.
Gefter et al., *Somatic Cell Genet.*, 3:231-236, 1977.
Goding, *In: Monoclonal Antibodies: Principles and Practice,* 2d ed., Orlando, Fla.,
Academic
Press, 60-61, 65-66, 71-74, 1986.
Gulbis and Galand, *Hum. Pathol.* 24(12), 1271-1285, 1993.
Guo et al., *Sci. Transl. Med.* 3:99 ra85, 2001.
Hodel et al., *Mol. Cell,* 10(2):347-58, 2002.
Huang et al., *Cancer Biol Ther.*, 2:702-706, 2003.
Huang et al., *Cancer Res.*, 65:10413-10422, 2005.
Jones et al., *Nature,* 321:522-525, 1986.
Kau et al., *Nat. Rev. Cancer,* 4(2):106-17, 2004.
Khatoon et al., *Ann. of Neurology,* 26, 210-219, 1989.
King et al., *J. Biol. Chem.*, 269, 10210-10218, 1989.
Kinlough et al., *J. Biol. Chem.*, 279(51):53071-53077, 2004.
Kinoshita et al., *Biochem. Biophys. Res. Commun.*, 394:205-210, 2010.
Kohler and Milstein, *Eur. J. Immunol.*, 6, 511-519, 1976. 95670519.1 71
Kohler and Milstein, *Nature,* 256, 495-497, 1975.
Kufe et al., *Hybridoma,* 3:223-232, 1984.
Kyte and Doolittle, *J. Mol. Biol.*, 157(1):105-132, 1982.
Leng et al., *J. Biol. Chem.*, 282:19321-19330, 2007.
Levitan et al., *J. Biol. Chem.*, 280:33374-33386, 2005.
Li et al., *Cancer Biol. Ther.*, 2:187-193, 2003b.
Li et al., *J. Biol. Chem.*, 276:35239-35242, 2001.
Li et al., *J. Biol. Chem.*, 276:6061-6064, 2001.
Li et al., *Mol. Cancer Res.*, 1:765-775, 2003c.
Li et al., *Mol. Cell Biol.*, 18:7216-7224, 1998.
Li et al., *Oncogene,* 22:6107-6110, 2003a.
Ligtenberg et al., *J. Biol. Chem.*, 267, 6171-6177, 1992.
Macao, *Nat. Struct. Mol. Biol.*, 13, 71-76, 2006.
Merlo et al., *Cancer Res.*, 49, 6966-6971, 1989.
Morrison, *Science,* 229(4719):1202-1207, 1985.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Owens and Haley, *J. Biol. Chem.*, 259, 14843-14848, 1987.
Owens and Haley, *J. Biol. Chem.*, 259:14843-14848, 1987.
PCT Application PCT/US86/02269
PCT Application WO 86/01533
Percipalle et al., *J. Mol. Biol.*, (4):722-32, 1997.
Perey et al., *Cancer Res.*, 52(22):6365-6370, 1992.
Persic et al., *Gene* 187:1, 1997
Posner et al., *Hybridoma* 6, 611-625, 1987.
Potter and Haley, *Meth. Enzymol.*, 91, 613-633, 1983.
Raina et al., *EMBO J.* 25:3774-3783, 2006.
Raina et al., *J. Biol. Chem.*, 279:20607-20612, 2004.

Remington's Pharmaceutical Sciences, 15th Ed., 3:624-652, 1990.
Ren et al., *Cancer Cell,* 5:163-175, 2004.
Ren et al., *J. Biol. Chem.,* 277:17616-17622, 2002.
Ryan and Wente, *Curr. Opin. Cell Biol.,* 12(3):361-71, 2000.
Schroeder et al., *J. Biol. Chem.,* 276(16):13057-13064, 2001.
Schroeder et al., *Oncogene,* 23:5739-5747, 2004.
Shaw et al., *J Natl. Cancer Inst.,* 80(19):1553-1559, 1988.
Siddiqui et al., *Proc. Natl. Acad. Sci. USA,* 85:2320-2323, 1988.
Suh and Gumbiner, *Exp. Cell Res.,* 290(2):447-56, 2003.
Sun et al., *J. Steroid Biochem.,* 26(1):83-92, 1987.
Tang et al., *J. Biol. Chem.,* 271:28324-28330, 1996.
Truscott et al., *J Cell Biol.,* 163(4):707-713, 2003.
Verhoeyen et al., *Science,* 239(4847):1534-1536, 1988.
Vermeer et al., *Nature,* 422(6929):322-6, 2003.
Wawrzynczak & Thorpe, In: *Immunoconjugates, Antibody Conuugates In Radioimaging And Therapy Of Cancer,* Vogel (Ed.), NY, Oxford University Press, 28, 1987.
Wei et al., *Cancer Cell,* 7:167-178, 2005.
Weis, *Cell,* 112(4):441-51, 2003.
Wen et al., *J Biol. Chem.,* 278:38029-38039, 2003.
Wood et al., *J Clin. Lab. Immunol.,* 17(4):167-171, 1985.
Yamamoto et al., *J Biol. Chem.,* 272:12492-12494, 1997.
Yin et al., *J Biol. Chem.,* 278:35458-35464, 2003.
Yin et al., *J Biol. Chem.,* 279:45721-45727, 2004.
Yin et al., *J. Biol. Chem.,* 282:257-266, 2007.
Young et al., *Cell.* 112(1):41-50, 2003.
Beniac, D. R., Melito, P. L., Devarennes, S. L., Hiebert, S. L., Rabb, M. J., Lamboo, L. L., Jones, S. M., and Booth, T. F. (2012). The organisation of Ebola virus reveals a capacity for extensive, modular polyploidy. PloS One 7, e29608.
Brauburger, K., Hume, A. J., Mühlberger, E., and Olejnik, J. (2012). Forty-five years of *Marburg* virus research. Viruses 4, 1878-1927.
Brochet, X., Lefranc, M. P., and Giudicelli, V. (2008). IMGT/V-QUEST: the highly customized and integrated system for IG and TR standardized V-J and V-D-J sequence analysis. Nucleic Acids Res. 36, W503-508.
Carette, J. E., Raaben, M., Wong, A. C., Herbert, A. S., Obernosterer, G., Mulherkar, N., Kuehne, A. I., Kranzusch, P. J., Griffin, A. M., Ruthel, G., et al. (2011). Ebola virus entry requires the cholesterol transporter Niemann-Pick Cl. Nature 477, 340-343.
Carragher, B., Kisseberth, N., Kriegman, D., Milligan, R. A., Potter, C. S., Pulokas, J., and Reilein, A. (2000). Leginon: An automated system for acquisition of images from vitreous ice specimens. J. Struct. Biol. 132, 33-45.
CDC (2009). Imported case of *Marburg* hemorrhagic fever—Colorado, 2008. MMWR 58, 1377-1381.
Chandran, K., Sullivan, N. J., Felbor, U., Whelan, S. P., and Cunningham, J. M. (2005). Endosomal proteolysis of the Ebola virus glycoprotein is necessary for infection. Science (New York, N.Y.) 308, 1643-1645.
Cook, J. D., and Lee, J. E. (2013). The secret life of viral entry glycoproteins: moonlighting in immune evasion. PLoS Path. 9, e1003258.
Côté, M., Misasi, J., Ren, T., Bruchez, A., Lee, K., Filone, C. M., Hensley, L., Li, Q., Ory, D.,
Chandran, K., et al. (2011). Small molecule inhibitors reveal Niemann-Pick Cl is essential for Ebola virus infection. Nature 477, 344-348.
Dias, J. M., Kuehne, A. I., Abelson, D. M., Bale, S., Wong, A. C., Halfmann, P., Muhammad, M. A., Fusco, M. L., Zak, S. E., Kang, E., Kawaoka, Y., Chandran, K., Dye, J. M., Saphire, E. O. (2011). A shared structural solution for neutralizing ebolaviruses. Nat. Struct. Mol. Biol. 18, 1424-7.
Dube, D., Brecher, M. B., Delos, S. E., Rose, S. C., Park, E. W., Schornberg, K. L., Kuhn, J. H., and White, J. M. (2009). The primed ebolavirus glycoprotein (19-kilodalton GP1,2): sequence and residues critical for host cell binding. J. Virol. 83, 2883-2891.
Dye, J. M., Herbert, A. S., Kuehne, A. I., Barth, J. F., Muhammad, M. A., Zak, S. E., Ortiz, R. A., Prugar, L. I., and Pratt, W. D. (2012). Postexposure antibody prophylaxis protects nonhuman primates from filovirus disease. Proc. Natl. Acad. Sci U.S.A. 109, 5034-5039.
Garbutt, M., Liebscher, R., Wahl-Jensen, V., Jones, S., Moller, P., Wagner, R., Volchkov, V., Klenk, H. D., Feldmann, H., and Stroher, U. (2004). Properties of replication-competent vesicular stomatitis virus vectors expressing glycoproteins of filoviruses and arenaviruses. J. Virol. 78, 5458-5465.
Giudicelli, V., Brochet, X., and Lefranc, M. P. (2011). IMGT/V-QUEST: IMGT standardized analysis of the immunoglobulin (IG) and T cell receptor (TR) nucleotide sequences. Cold Spring Harb. Protoc. 2011, 695-715.
Hashiguchi, T., Fusco, M. L., Bornholdt, Z. A., Lee J. E., Flyak A. I., Matsuoka, R., Kohda D., Yanagi Y., Hammel M., Crowe J. E. Jr., and Saphire, E. O. Cell 2015, in press.
Johnson, E. D., Johnson, B. K., Silverstein, D., Tukei, P., Geisbert, T. W., Sanchez, A. N., and Jahrling, P. B. (1996). Characterization of a new *Marburg* virus isolated from a 1987 fatal case in Kenya. Arch. Virol. Suppl. 11, 101-114.
Kajihara, M., Marzi, A., Nakayama, E., Noda, T., Kuroda, M., Manzoor, R., Matsuno, K., Feldmann, H., Yoshida, R., Kawaoka, Y., et al. (2012). Inhibition of *Marburg* virus budding by nonneutralizing antibodies to the envelope glycoprotein. J. Virol. 86, 13467-13474.
Ksiazek, T. G., West, C. P., Rollin, P. E., Jahrling, P. B., and Peters, C. J. (1999). ELISA for the detection of antibodies to Ebola viruses. J. Infect. Dis. 179 Suppl 1, S192-198.
Lander, G. C., Stagg, S. M., Voss, N. R., Cheng, A., Fellmann, D., Pulokas, J., Yoshioka, C., Irving, C., Mulder, A., Lau, P. W., et al. (2009). Appion: an integrated, database-driven pipeline to facilitate EM image processing. J. Struct. Bio. 166, 95-102.
Lee, J. E., Fusco, M. L., Hessell, A. J., Oswald, W. B., Burton, D. R., and Saphire, E. O. (2008). Structure of the Ebola virus glycoprotein bound to an antibody from a human survivor. Nature 454, 177-182.
Lubaki, N. M., Ilinykh, P., Pietzsch, C., Tigabu, B., Freiberg, A. N., Koup, R. A., and Bukreyev, A. (2013). The lack of maturation of Ebola virus-infected dendritic cells results from the cooperative effect of at least two viral domains. J. Virol. 87, 7471-7485.
Maruyama, T., Rodriguez, L. L., Jahrling, P. B., Sanchez, A., Khan, A. S., Nichol, S. T., Peters, C. J., Parren, P. W., and Burton, D. R. (1999). Ebola virus can be effectively neutralized by antibody produced in natural human infection. J. Virol. 73, 6024-6030.
Marzi, A., Yoshida, R., Miyamoto, H., Ishijima, M., Suzuki, Y., Higuchi, M., Matsuyama, Y., Igarashi, M., Nakayama, E., Kuroda, M., et al. (2012). Protective efficacy of neutralizing monoclonal antibodies in a nonhuman primate model of Ebola hemorrhagic fever. PloS One 7, e36192.
Murin, C. D., Fusco, M. L., Bornholdt, Z. A., Qiu, X., Olinger, G. G., Zeitlin, L., Kobinger, G. P., Ward, A. B., Saphire, E. O. (2014). Structures of protective antibodies reveal sites of vulnerability on Ebola virus. Proc. Natl. Acad. Sci. U.S.A 111, 17182-17187.

Nanbo, A., Imai, M., Watanabe, S., Noda, T., Takahashi, K., Neumann, G., Halfmann, P., and Kawaoka, Y. (2010). Ebolavirus is internalized into host cells via macropinocytosis in a viral glycoprotein-dependent manner. PLoS Pathog. 6, e1001121.

Olinger, G. G., Pettitt, J., Kim, D., Working, C., Bohorov, O., Bratcher, B., Hiatt, E., Hume, S. D., Johnson, A. K., Morton, J., et al. (2012). Delayed treatment of Ebola virus infection with plant-derived monoclonal antibodies provides protection in rhesus macaques. Proc. Natl. Acad. Sci U.S.A. 109, 18030-18035.

Pettersen, E. F., Goddard, T. D., Huang, C. C., Couch, G. S., Greenblatt, D. M., Meng, E. C., and Ferrin, T. E. (2004). UCSF Chimera—A visualization system for exploratory research and analysis. J. Comput. Chem. 25, 1605-1612.

Pettitt, J., Zeitlin, L., Kim, D. H., Working, C., Johnson, J. C., Bohorov, O., Bratcher, B., Hiatt, E., Hume, S. D., Johnson, A. K., Morton, J., Pauly, M. H., Whaley, K. J., Ingram, M. F., Zovanyi, A., Heinrich, M., Piper, A., Zelko, J., Olinger, G. G. (2103). Therapeutic intervention of Ebola virus infection in rhesus macaques with the MB-003 monoclonal antibody cocktail. Sci. Transl. Med. 5, 199ra113.

Potter, C. S., Chu, H., Frey, B., Green, C., Kisseberth, N., Madden, T. J., Miller, K. L., Nahrstedt, K., Pulokas, J., Reilein, A., et al. (1999). Leginon: A system for fully automated acquisition of 1000 electron micrographs a day. Ultramicroscopy 77, 153-161.

Qiu, X., Audet, J., Wong, G., Pillet, S., Bello, A., Cabral, T., Strong, J. E., Plummer, F., Corbett, C. R., Alimonti, J. B., et al. (2012). Successful treatment of Ebola virus-infected cynomolgus macaques with monoclonal antibodies. Sci. Trans. Med. 4, 138ra181-138ra181.

Qiu, X., Wong, G., Audet, J., Bello, A., Fernando, L., Alimonti, J. B., Fausther-Bovendo, H., Wei, H., Aviles, J., Hiatt, E., et al. (2014). Reversion of advanced Ebola virus disease in nonhuman primates with ZMapp. Nature 514, 47-53.

Saeed, M. F., Kolokoltsov, A. A., Albrecht, T., and Davey, R. A. (2010). Cellular entry of ebola virus involves uptake by a macropinocytosis-like mechanism and subsequent trafficking through early and late endosomes. PLoS Pathog. 6, e1001110.

Saphire, E. O. (2013). An update on the use of antibodies against the filoviruses. Immunotherapy 5, 1221-1233.

Smith, D. H., Johnson, B. K., Isaacson, M., Swanapoel, R., Johnson, K. M., Killey, M., Bagshawe, A., Siongok, T., and Keruga, W. K. (1982). *Marburg*-virus disease in Kenya. Lancet 1, 816-820.

Suloway, C., Pulokas, J., Fellmann, D., Cheng, A., Guerra, F., Quispe, J., Stagg, S., Potter, C. S., and Carragher, B. (2005). Automated molecular microscopy: the new Leginon system. J. Struct. Bio. 151, 41-60.

Tang, G., Peng, L., Baldwin, P. R., Mann, D. S., Jiang, W., Rees, I., and Ludtke, S. J. (2007). EMAN2: an extensible image processing suite for electron microscopy. J. Struct. Bio. 157, 38-46.

Thomas, D., Newcomb, W. W., Brown, J. C., Wall, J. S., Hainfeld, J. F., Trus, B. L., and Steven, A. C. (1985). Mass and molecular composition of vesicular stomatitis virus: a scanning transmission electron microscopy analysis. J. Virol. 54, 598-607.

Towner, J. S., Amman, B. R., Sealy, T. K., Carroll, S. A. R., Comer, J. A., Kemp, A., Swanepoel, R., Paddock, C. D., Balinandi, S., Khristova, M. L., et al. (2009). Isolation of genetically diverse *Marburg* viruses from Egyptian fruit bats. PLoS Path. 5, e1000536.

Towner, J. S., Khristova, M. L., Sealy, T. K., Vincent, M. J., Erickson, B. R., Bawiec, D. A., Hartman, A. L., Comer, J. A., Zaki, S. R., Stroller, U., et al. (2006). *Marburgvirus* genomics and association with a large hemorrhagic fever outbreak in Angola. J. Virol. 80, 6497-6516.

Towner, J. S., Paragas, J., Dover, J. E., Gupta, M., Goldsmith, C. S., Huggins, J. W., and Nichol, S. T. (2005). Generation of eGFP expressing recombinant Zaire ebolavirus for analysis of early pathogenesis events and high-throughput antiviral drug screening. Virology 332, 20-27.

van Heel, M., Harauz, G., Orlova, E. V., Schmidt, R., and Schatz, M. (1996). A new generation of the IMAGIC image processing system. J. Struct. Bio. 116, 17-24.

Warfield, K. L., Alves, D. A., Bradfute, S. B., Reed, D. K., VanTongeren, S., Kalina, W. V., Olinger, G. G., and Bavari, S. (2007). Development of a model for *marburgvirus* based on severe-combined immunodeficiency mice. Virol. J. 4, 108.

Warfield, K. L., Bradfute, S. B., Wells, J., Lofts, L., Cooper, M. T., Alves, D. A., Reed, D. K., VanTongeren, S. A., Mech, C. A., and Bavari, S. (2009). Development and characterization of a mouse model for *Marburg* hemorrhagic fever. J. Virol. 83, 6404-6415.

Warren, T. K., Wells, J., Panchal, R. G., Stuthman, K. S., Garza, N. L., Van Tongeren, S. A., Dong, L., Retterer, C. J., Eaton, B. P., Pegoraro, G., et al. (2014). Protection against Filovirus diseases by a novel broad-spectrum nucleoside analogue BCX4430. Nature 508, 402-405.

World Health Organization (2014a). Ebola Situation Report, in W. H. O. Global Alert and Response. 7 Jan. 2015.

World Health Organization (2014b). *Marburg* virus disease—Uganda, 10 Oct. 2014, in W. H. O. Global Alert and Response.

Yu, X., McGraw, P. A., House, F. S., and Crowe, J. E., Jr. (2008). An optimized electrofusion-based protocol for generating virus-specific human monoclonal antibodies. J. Immunol. Met. 336, 142-151.

What is claimed is:

1. An engineered cell producing an antibody or antibody fragment characterized by heavy chain CDR sequences of SEQ ID NOS: 104, 105 and 106 and light chain CDR sequences of SEQ ID NO: 150, DNN and SEQ ID NO: 151.

2. The engineered cell of claim 1, wherein said antibody or antibody fragment is encoded by light and heavy chain variable sequences comprising SEQ ID NO: 25 and SEQ ID NO: 24, respectively.

3. The engineered cell of claim 1, wherein said antibody or antibody fragment is encoded by light and heavy chain variable sequences having 90% identity to SEQ ID NO: 25 and SEQ ID NO: 24, respectively.

4. The engineered cell of claim 1, wherein said antibody or antibody fragment comprises light and heavy chain variable sequences of SEQ ID NO: 61 and SEQ ID NO: 60, respectively.

5. The engineered cell of claim 1, wherein said antibody or antibody fragment comprises light and heavy chain variable sequences having 95% identity to SEQ ID NO: 61 and SEQ ID NO: 60, respectively.

6. The engineered cell of claim 1, wherein the antibody fragment is a recombinant ScFv (single chain fragment variable) antibody, Fab fragment, $F(ab')_2$ fragment, or Fv fragment.

7. The engineered cell of claim 1, wherein said antibody is a chimeric antibody.

8. The engineered cell of claim 1, wherein said antibody is an IgG.

9. The engineered cell of claim 1, wherein said antibody or antibody fragment also binds to Ebola virus.

10. The engineered cell of claim 1, wherein said antibody or antibody fragment further comprises a cell penetrating peptide or is an intrabody.

11. A method of inhibiting a *Marburg* virus or Ebola virus in a subject comprising delivery to said subject an antibody or antibody fragment having heavy chain CDR sequences of SEQ ID NOS: 104, 105 and 106 and light chain CDR sequences of SEQ ID NO: 150, DNN and SEQ ID NO: 151.

12. The method of claim 11, wherein said antibody or antibody fragment is a chimeric antibody or is bispecific antibody.

13. The method of claim 12, wherein said antibody or antibody fragment is a bispecific antibody that (a) targets glycoprotein of a *Marburg* virus or Ebola virus, and (b) targets a structural feature of a *Marburg* or Ebola virus particle.

14. The method of claim 13, wherein said structural feature is a *Marburg* or Ebola virus glycoprotein domain other than the receptor binding domain.

15. The method of claim 13, wherein said structural feature is a *Marburg* or Ebola virus virion structure other than the glycoprotein.

16. The method of claim 15, wherein said virion structure is a lipid, carbohydrate or protein.

17. The method of claim 11, wherein said antibody or antibody fragment is a bispecific antibody that (a) targets a glycoprotein of a *Marburg* virus or Ebola virus particle and (b) targets a host cell surface structure cells that is trafficked to endosomes.

18. The method of claim 11, wherein said subject is infected with a *Marburg* virus.

19. The method of claim 11, wherein said subject is infected with an Ebola virus.

20. The method of claim 11, wherein said antibody or antibody fragment is encoded by light and heavy chain variable sequences comprising SEQ ID NO: 25 and SEQ ID NO: 24, respectively.

21. The engineered cell of claim 11, wherein said antibody or antibody fragment comprises light and heavy chain variable sequences of SEQ ID NO: 61 and SEQ ID NO: 60, respectively.

22. The method of claim 11, wherein the antibody fragment is a recombinant ScFv (single chain fragment variable) antibody, Fab fragment, $F(ab')_2$ fragment, or Fv fragment.

23. The method of claim 11, wherein said antibody is a chimeric antibody.

24. The method of claim 11, wherein said antibody is an IgG.

* * * * *

```
SEQUENCE LISTING

<160> NUMBER OF SEQ ID NOS: 169

<210> SEQ ID NO 1
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 1
```

-continued catgtacgac gcgtcaacat gaggacta 28

<210> SEQ ID NO 2
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 2
tctagcagct cgagctatcc aatatattta gtaaagatac gacaa 45

<210> SEQ ID NO 3

<400> SEQUENCE: 3

000

<210> SEQ ID NO 4
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 4
catgtacgac gcgtcaacat gaggacta 28

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
actaagccct gctgccaggt 20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
acaacaatgt accgaggcaa 20

<210> SEQ ID NO 7
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 7
tctagcagct cgagctatcc aatatattta gtaaagatac gacaa 45

<210> SEQ ID NO 8
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 8
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggcagg ggctggagtg ggtctcaggt attagtgcta ctggtggtaa cacatactac 180
ccagactccg tgaagggccg attcaccatc tccagagaca attccaagaa cacgctgtac 240
ctgcaaatga acagcctgag agccgaggac acggccgtat attactgtgc gagaccatta 300
caatttttga cctggttcga cccctggggc cagggaaccc tggtcaccgt ctcctca 357

<210> SEQ ID NO 9
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 9
gaaattgtgt tgacacagtc tccggccacc ctgtctttgt ctccagggga aagagccacc 60
ctctcctgca gggccagtca gagtgttaac aacttcttag cctggtacca acagaaacct 120
ggccagcctc ccaggctcct catctatgat gcaaccaaca gggccactgg catcccagcc 180
aggttcagtg gcagtgggtc tgggacagac ttcactctca ccatcagcag cctagagcct 240
gaagattttg cagtttatca ctgtcagcac cgtagcaact ggccctcgat caccttcggc 300
caagggacac gactggagat taaa 324

<210> SEQ ID NO 10
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 10
cagctgcagc tgcaggagtc gggcccagga ctggtgaagc cttcggagac cctgaacctc 60
tcctgcactg tctctggtga ctccatcaac aatactaatt actactgggc ctggatccgc 120
cagcccccag ggaaggggct ggagtacatt gggagtatct attatagtgg gagcacctac 180
tacaacccgt ccctcaagag ccgagtcacc atgtccgtag acgcgtccaa gaaccagttc 240
tccctgaggc tgagctctgt gaccgccgca gacacggctg tgtattactg tgcgacacac 300
cccacactgg gggcttttgt attactgtgg ttcggggcaa actttgacca ctggggccag 360
ggaaccctgg tcaccgtctc ctca 384

<210> SEQ ID NO 11
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 11
caggctgtgg tgacgcagcc gccctcagtg tctggggccc caggccagag ggtcaccatc 60
tcctgcactg ggagcagctc caacatcggg gcaaattatg atgtacactg gtaccagcag 120
cttccaggga cagcccccaa actcctcatg tatagtaaca ctaatcggcc ctcaggggtc 180
cctgaccgat tctctggctc caagtctggc acttcagcct ccctggccat cactgggctc 240
caggctgagg atgaggctga ttattactgc cagtcctatg acaacagcct gaacagttgg 300

-continued gtgttcggcg gagggaccca gctgaccgtc cta 333

<210> SEQ ID NO 12
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 12
cagctgcagc tgcaggagtc gggcccagga ctggtgaagc cttcggagac cctgtccctc 60
acctgcactg tgtctggtgg ctccatcagc agtagtagtt actactgggg ctggatccgc 120
cagcccccag ggaaggggct ggagtggatt gggagtgtct attatagtgg gggcgcctcc 180
tacaacccgt ccctgaagag tcgagccacc atatccgtag acacgtccaa gaaccagttc 240
tccctgaacc tggactctgt gagcgccgca gacacggcta tatattactg tgcgagtatt 300
tatggttcag ggacctttta ctactacttc tacatggacg tctggggcaa agggtccacg 360
gtcaccgtct cctca 375

<210> SEQ ID NO 13
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 13
gacatccaga tgacccagtc tccatcctcc ctgtctgcat ctgtaggaga cagagtcacc 60
atcacttgcc aggcgagtca ggtcattagc aactatttaa attggtatca acagaaacca 120
gggaaagccc ctaagctcct gatctacgac acatccaatt tgaaaacagg ggtcccatca 180
aggttcagtg gaagtggatc tgggacagat tttactttca ccatcagcag cctgcagcct 240
gaagatattg caacatatta ttgtcaacaa tatgaaaatc tccagttcac tttcggccct 300
gggaccaagg tggatatcaa a 321

<210> SEQ ID NO 14
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 14
caggtccagc ttgtgcagtc tggggctgag gtgaagaagc ctggggcctc agtgaaggtc 60
tcctgcaagg cttctggaca caccttcact acctatgcta tccattgggt gcgccaggcc 120
cccggacaag ggcttgagtg gatgggatgg atcaaccctg acaatgataa cacagaatat 180
tcacagaagt tccagggcag agtcaccatt accagggaca catccgcgag cacagcctac 240
atggagctga gcagcctgat atctgaggac acggctgtgt tttactgtgc gagcgcttct 300
tacacttttt ggagtggtta ttatagtggt ctggactact ggggccaggg aaccctggtc 360
accgtctcct ca 372

<210> SEQ ID NO 15
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 15
gaaattgtgt tgacgcagtc tccaggcacc ctgtctttgt ctccagggga aagagccacc 60
ctctcctgca gggccagtca gagtgttagc atcaactact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctcc gtggactttc 300
ggccctggga ccaaggtgga tatcaaa 327

<210> SEQ ID NO 16
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 16
caggttcagc tggtgcagtc tggagctgag gtgaagaagc ctggggcctc agtgaaggtc 60
tcctgcaagg cttctggtta tacctttagc aactatggta tcagctgggt gcgacaggcc 120
cctggacaag ggcttgagtg gatgggatgg gtcaacactt ataatggtaa cacatactat 180
gctcagagcc ttcagggcag agtcaccatg accacagaca catccacgag cacagcctac 240
atggagctga ggagcctgak atctgacgac acggccgtgt acttttgtgc gagagatcac 300
cccattacga tttttggagt gattattctt ggggagccaa caacctgggg ccagggaacc 360
ctggtcaccg tctcctca 378

<210> SEQ ID NO 17
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 17
gaaatagtga tgacgcagtc tccagccacc ctgtctgtgt ctccagggga aagagccacc 60
ctctcctgca gggccagtca gagtgttaac agcaacttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg aagtttatta ctgtcagcag tataataact ggccccggac gttcggccaa 300
gggaccaagg tggatatcaa a 321

<210> SEQ ID NO 18
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 18
caggtgcagc tgcaggagtc gggcccagga ctggtgaagc cttcggagac cctgtccctc 60
acctgcactg tctctggtga ctccatcaat aattattact ggagctggat ccggcagccc 120
ccagggaagg gactggagtg gattgggtat atctattaca gtaataccaa ctacaacccc 180
tccctcaaaa gtcgagtcac catatcagta gacacgtcca agaaccagtt ctccctgagg 240

-continued ctgagctctg tgaccgctgc ggacacggcc gtgtattact gtgcgagatc tccattattt 300
tggttcgggg agttcttttc ctcgcctgat cactttgact tttggggcca gggaaccctg 360

<210> SEQ ID NO 19
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 19
cagtctgccc tgactcagcc tgcctccgtg tctgggtctc ctggacagtc gatcaccatc 60
tcctgcactg gaaccagcag tgatgttggg agttatgacc ttgtctcctg gtaccaacag 120
cacccaggca aagcccccaa actcatgctt tatgagggca ctaagcggcc ctcaggggtt 180
tctaatcgct tctctggctc caagtctggc aacacggcct ccctgacaat ctctgggctc 240
caggctgagg acgaggctga ttattactgc tgctcatatg caggtggtag cactttggta 300
ttcggcggag ggacccaggt gaccgtccta 330

<210> SEQ ID NO 20
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 20
caggtgcagc tgcaggagtc gggcccagga ctggtgaagc cttcggagac cctgtccctc 60
acctgcactg tctctggtga ctccataagt agatactact ggagttggat ccggcagccc 120
ccagggaagg gactggagtg gattgggtat ctctattaca gtgggagtac cgactacaac 180
ccctccctca agagtcgagt caccatttca gtagacacgt ccaagaacca gttctccctg 240
aatctgacct ctgtgaccgc tgcggacacg gccgtgtatt actgtgcgag aggatcctcc 300
cggggtatag gagtggtgtc gcactggttc gacccctggg gccagggaac c 351

<210> SEQ ID NO 21
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 21
tcctatgtgc tgactcagcc accctcggtg tcagtggccc caggacagac ggccagaatc 60
acctgtgggg gatccaacat gggatataaa agtgtgcagt ggtaccagca gaggccaggc 120
caggcccctg tgctggtcgt ctatgatgat accgaccggc cctcagggat ccctgagcga 180
ttctctggct ccaactctgg ggccacggcc accctgacca tcagcagtgt cgaagccggg 240
gatgaggccg actattactg tcaggtgtgg gatagtagta gcgatcatca tgtggtattc 300
ggcggaggga cccaggtgac cgtccta 327

<210> SEQ ID NO 22
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 22

-continued

```
caggtgcagc tgcaggagtc gggcccagga ctggtgaagc cttcggagac cctgtccctc      60

tcctgcactg tctctggtgg ctccatcagt ggttactact ggagctggat ccggcagccc     120

ccagggaagg gactggagtg gattgggtat atctatcaca gtgggagtcc caactacaac     180

ccctccctca agagtcgagt caccatttca gtagacacgt ccaagaacca gttctccctg     240

aggctgagct ctgtgaccgc cgcagacacg gccatgtatt actgtgcgag aactgcttat     300

acggtgggtt ttttcgccta ctactacttg gatgtctggg gcagagggac caccctgtcc     360

ctctcctgc                                                             369


<210> SEQ ID NO 23
<211> LENGTH: 295
<212> TYPE: DNA
<213> ORGANISM: Artificial sequence
<220> FEATURE:
<223> OTHER INFORMATION: Synthetic oligonucleotide

<400> SEQUENCE: 23

gacatccaga tgacccagtc tccatcctcc ctgtctgcat ctgtagggga cagagtcacc      60

atcacttgcc aggcgagtca cgacattagc aactatttaa attggtatca gcaaaaacca     120

ggcaaagccc ctaagctcct gatctacgat gcatccaatt tggaaacggg ggtcccatca     180

aggttcagtg gagctggatc tgggacagat tttactttca ccatcagcag cctgcagcct     240

gaagatgttg caacatatta ctgtcaagta tatgataatc tcctcttcac ttcgg          295


<210> SEQ ID NO 24
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 24

cagctgcagc tgcaggagtc gggcccagga ctggtgaagc cttcggagac cctgtccctc      60

acctgcactg tctctggtgt ctccatcagc gataatagtt attactgggg ctggatccgc     120

cagcccccag ggaagggcct ggagtggatt gggactatct cttatagtgg gaacacctac     180

tacaacccgt ccctcaagag tcgagtcagc atatccggag acacgtccaa gcaccagctc     240

tccctgaagg tgagctctgt gaccgccgca gacacggctg tctattactg tgcgagacag     300

cggatagtat caggatttgt ggagtggcta tcaaaatttg actactgggg ccaggggacc     360

ctggtcaccg tctcctca                                                   378


<210> SEQ ID NO 25
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 25

cagtctgtgc tgacgcagcc gccctcagtg tctggggccc cagggcagag ggtcaccatc      60

tcctgcactg ggagcagctc caacatcggg gcaggttttg atgtacactg gtaccagcaa     120

cttccaggaa cagcccccaa actcctcatc tatgataaca acaatcggcc ctcaggggtc     180

cctgaccgat tctctggctc caagtctggc acctcagcct ccctggccat cactgggctc     240

caggctgagg atgaggctga ttattactgc cagtcctatg acaccagcct gagtggtccc     300
```

gtggtgttcg gcggagggac caagctgacc gtccta 336

<210> SEQ ID NO 26
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 26
caggtgcagc tgcaggagtc gggcccagga ctggtgaagc cttcacagac cctgtccctc 60
tcctgcactg tctctggtgg ctccatcagc agtgatagtt actactggaa ctggatccgc 120
cagcacccag ggaagggcct ggagtggatt gggtacgtct attatagtgg gagcaccaac 180
tacaacccgt ccctcaagag tcgagttatc atatcactag acacgtctaa gaaccagttc 240
tccctgaagc tgaactctgt gactgccgcg gacacggccg tgtattactg tgcgagagcc 300
gattattatg gttcagggag tttcttctac tactaccaca tggacgtctg gggcaaaggg 360

<210> SEQ ID NO 27
<211> LENGTH: 297
<212> TYPE: DNA
<213> ORGANISM: Artificial sequence
<220> FEATURE:
<223> OTHER INFORMATION: Synthetic oligonucleotide

<400> SEQUENCE: 27
gacatccaga tgacccagtc tccttccacc ctgtctgcat ctgtaggaga cagagtcacc 60
atcacttgcc gggccagtca gagtatttat acctggttgg cctggtatca gcagaaacca 120
gggaaagccc ctaagctcct gatccataag tcgtctagtt tagaaagtgg ggtcccttca 180
aggttcagcg gcagtggatc tgggacagaa ttcactctca ccatcagcag cctgcagcct 240
gatgattttg cgacttatta ctgccaccag tattatgttt atccttgcac gtcggcc 297

<210> SEQ ID NO 28
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 28
cagctgcagc tgcaggagtc gggcccagga ctggtgaagc cttcggagac tctgtttctc 60
agttgcgctg tctctggtgg ctccatcgcc ggtagcactc actactgggg ctggatccgc 120
cagcccccag ggaaggggct ggagtggatt gggagtatct ctgaaagtgg gagcacctac 180
cacaatccgt ccctcaagag tcgagtcacc atatccgtgg acacgtccaa aaattacttc 240
tccctgaact tgagctctgt gaccgccgca gacacggctg tgtattactg tgcgagaata 300
gtgggtcaat ctggtacctt tatctactac tattacgcca tggacgtctg gggcacaggg 360
accctggtca ccgtctcctc a 381

<210> SEQ ID NO 29
<211> LENGTH: 309
<212> TYPE: DNA
<213> ORGANISM: Artificial sequence
<220> FEATURE:
<223> OTHER INFORMATION: Synthetic oligonucleotide

<400> SEQUENCE: 29
gacatccagt tgacccagtc tccatccttc ctgtctgcat ctgtaggaga cagagtcacc 60

-continued atcacttgcc gggccagtca gggcattagt agttatttag cctggtatca gcaaaaacca 120
gggaaagccc ctaagctcct gatctatgct gcctccactt tgcaacgtgg ggtcccatca 180
aggttcagcg gcagtggatc tgggacagag ttcactctca caatcagcag cctgcagcct 240
gaagactctg caacttatta ctgtcaacag cttaatagtt atctcgcgct cattttcggc 300
ggagggacc 309

<210> SEQ ID NO 30
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 30
caggtgcagc tgcaggagtc gggcccagga ctggtgaagc cttcggagac cctgtccctc 60
acctgcagtg tctctggtga ctccgtcagc agtggtgatt actattggag ctggctccgg 120 cagcccccg ggaagggact ggagtggatt ggctatatct attacagtgg ggccaccaac 180
tacaacccct ccctcaagag tcgagtcacc atttcactag acacgtccaa gaaccagttc 240
tccctgaaac tgacctctgt gaccgctgcg gacacggccg tctattactg tgcgagagaa 300
cgggcgggat tttggagtg gttatttttt gaagattggg gccagggaac c 351

<210> SEQ ID NO 31
<211> LENGTH: 309
<212> TYPE: DNA
<213> ORGANISM: Artificial sequence
<220> FEATURE:
<223> OTHER INFORMATION: Synthetic oligonucleotide

<400> SEQUENCE: 31
gacatccaga tgacccagtc tccatcctcc ctgtctgcat ctgtaggaga cagagtcacc 60
attttttgcc gggcaagtca gagcattggc acctatttaa gttggtatca acagaaacca 120
gggaaagccc ctaaggtctt gatctatgct acatccaatt tgcaaagtgg ggtcccatca 180
aggttcagtg gcagtggatc tgggacagaa ttcactctca ccatcagcag tctgcaacct 240
gaagattttg caacatacta ctgtcaacaa agtaggacat tcggccaagg gaccaaggtg 300
gatatgaaa 309

<210> SEQ ID NO 32
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 32
cagctgcagc tgcaggagtc gggcccagga ctggtgaagc cttcggagac cctgtccctc 60
acctgcactg tcgctggtgg ccccatcacc agtaataatt actactgggg ctggatccgt 120
cagtccccag ggaaggggct ggagtggatt gggagtgttt attatagtgg gaacacctac 180
tataatccgt ccatcaagac tcgagtcacc atgtccgtgg acacgtcgaa gagccagttc 240
tccctaaaac tgaactccgt gaccgccgca gacacggctg tctattactg tgcgagacag 300
tttaggcttt tacaatttgt ggagtggcta caccactttg actcctgggg cccagggaac 360

<210> SEQ ID NO 33

-continued

<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 33
tcctatgtgc tgactcagcc accctcggtg tcagtggccc caggacagac ggccaggatt 60
ccctgtgggg gcaatgatat tgcgaataaa cgtgtgcact ggtaccagca gaagccaggc 120
caggccccta tgctggtcgt ctatgatgat ggcgaccggc cctcagggat ccctgagcga 180
ttctctggct ccaactctgg gaacacggcc accctgacca tcagccgggt cgaagccggg 240
gatgaggccg actattactg tcaggtgtgg gaaaatagta gtgatctttg tgtggtattc 300
ggcggaggga ccaagctgac cgtccta 327

<210> SEQ ID NO 34
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 34
gaggtgcagc tggtggagtc tgggggaggc ttggtaaagc caggggggtc cctgagaatc 60
tcctgtgtaa cttctggatt cacctttggt gattatgcta tgagttggtt ccgccaggct 120
ccagggaagg ggctggagtg ggtaggtttc attagaaaca aaggttatgg tgggacaata 180
gattacgccg cgtctgtgaa aggcagattc accatctcaa gagatgattc caagagtatc 240
gcctatctgc aaatgaacag cctgaaaacc gaggacacag ccgtttatta ctgtaccgga 300
gtccgattgc attacgattt ctggagtggt tatgatgatg attcttttca tatatggggc 360
caagggacaa tg 372

<210> SEQ ID NO 35
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 35
gatggtgtga tgactcagtc tccactctcc ctgcccgtca cccctggaca gccggcctcc 60
atctcctgca ggtctactca aagcctcgta cacggagatg gagacaccta cttatattgg 120
tttcagcaga ggccaggcca atctccaagg cgcctaattt ataaggtttc taatcgggac 180
tctggggtcc cagacagatt cagcggcagt gggtcaggca ctgatttcac actgaaaatc 240
agcagggtgg aggctgagga tgttggggtt tattactgca tgcaaagtac acactggcct 300
ccgacttttg gccag 315

<210> SEQ ID NO 36
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 36
cagctgcagc tgcaggagtc gggcccagga ctggtgaagc cttcggagac cctgtccctc 60
acctgcgctg tgtcaggtgg ctccatcagc agtagtggtt actgctgggg ctggatccgc 120
cagcccccag ggaaggggct ggagtggatc gcgagtatct gctctagtgg gaccacctac 180
ttcaattcgt ccctcaagag tcgagtctcc atatccatag acacgtccag gccccagttc 240
ttactgaacc tgcgctctct gaccgccgca gacacggctg tctactattg tgcgagacaa 300
agaatggagt tacatttttt ggagtggttg tttccttttg actcctgggg ccagggaacc 360
ctggtcaccg tctcctca 378

<210> SEQ ID NO 37
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 37
gacatagtga tgacgcagtc tccagccacc ctgtctgtgt ctccaggaga gagagccacc 60
ctctcctgca gggccagtca gagtgttagc agcaacttag cctggtacca gcagaaacct 120
ggccaggctc ccaggctcct catctctggt gcatccacta gggccactgg tatcccagcc 180
agattcagtg gcagtgggtc tgggacagag ttcactctca ccatcagcag cctgcagtct 240
gaagattttg cagtttatta ctgtcagcag tatattaact ggccgtgcag ttttggccag 300
gggaccaagg tggatatcaa a 321

<210> SEQ ID NO 38
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 38
gaggtgcagc tggtggagtc tgggggaggc ttggtccagc ctggggggtc cctgagactc 60
tcctgtgcag cctctggatt cacctttagt agttattgga tgaactgggt ccgccaggct 120
ccagggaagg ggctggagtg ggtggccaac gtaaaggaag atggaagtaa gaagtactat 180
gtggactctg tgaaggggcg attcaccatc tccagagaca acgccaagaa ctctctgtat 240
ctgcaaatga acagcctgag agtcgaggac acggctctct attactgtgt gagaggagag 300
gattgtagtg gtggaaggtg ctcctcccta tttttccgc agcactactt tgactactgg 360
ggcccaggga ac 372

<210> SEQ ID NO 39
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 39
gacatccaga tgacccagtc tccatcttcc gtgtctgcat ctgtaggaga cagagtcacc 60
atcacttgtc gggcgagtca gggtattctc aactggttag cctggtatca gcagaaacca 120
gggaaagccc ctaaactcct gatctatgct gcatccagtg tacaaagtgg ggtcccatca 180
aggttcagcg gcagtggatc tggcacagat ttcaccctca ccattagcag cctgcagcct 240
gacgattttg caacttacta ttgtcagcaa actaacagtt tccctctcac tttcgccgga 300
gggaccaagg tggagatcaa a 321

<210> SEQ ID NO 40
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 40
caggtgcagc tgcaggagtc gggccccgga ctggtgaagc cttcggagac cctgtccctc 60
acctgcactg tctctggtgc ctccatcagt ggtaacttct ggagctggat ccggcagccc 120
ccagggaagg gactggaata tattggttat atgtctgaca ttgggaccac caactacagc 180
ccctccctca agagtcgagt caccatttca gtagacacgt ccaagaacca gttctccctg 240
aatctgacct ctgtgaccgc tgcggacgcg gccgtgtatt actgtgcgag acttgtagca 300
gtgcctggtt tcttctatca ctactacatg gacgtctggg gwgaggggac cctggtcacc 360
gtctcctca 369

<210> SEQ ID NO 41
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 41
gacatygtga tgacccagtc tccatcttcc gtgtctgcat ctgtaggaga cagagtcacc 60
atcacttgtc gggcgagtca gggtattagt ggctggttgg cctggtatca gcagaaacca 120
gggaaagccc ctaagctcct gatctatgct acatccactt tgcaaagtgg ggtcccgtca 180
aggttcagcg gcagtgaatc tgggacagct ttcactctca ccatcagcag cctgcagcct 240
gaagattttg caacttacta ttgtcaacag gctaacagtt tccctctcac tttcggcgga 300
gggaccaagg tggagatcaa a 321

<210> SEQ ID NO 42
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 42
caggtgcagc tggtggagtc tgggggaggc gtggtccagc ctgggggggtc cctgaggatc 60 tcctgtgcag ccgctggatt cacctttagt agaagtggca tgcactgggt ccgccaggct 120
ccaggcaagg ggctggagtg ggtggcagtc atttcatatg acggaaatac tgaacactat 180
gcagactcca tggagggccg agtcaccgtc tccagagaca actccaacaa cacgctgtac 240
ctgcaaatga acagcctgag agcgggggac acggctgtgt attattgtgc gaaagatcga 300
catactacag ggagtaatta taatggcgga ctcttggacc actggggcca gggaaccctg 360
gtcaccgtct cctca 375

<210> SEQ ID NO 43
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 43

-continued

```
gaaaccgtga tgacccagtc tccagactcc ctggctgtgt ctctgggcga gagggccacc      60

atcaactgca agtccagcca gagtgtttta cacagctcca agaatagaaa ctacttggct     120

tggtaccagc agaagccagg acagcctcct aagttgctca tttactgggc atctacccgg     180

gaatccgggg tccctgaccg cttcagtggc agcgggtctg ggacagattt cactctcacc     240

atcagcagcc tgcaggctga agatgtggca ctttattact gtcagcaata ttatactagt     300

ccgctgactt tcggccaagg gacacgactg gagattaaa                            339


<210> SEQ ID NO 44
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Gln Gly Leu Glu Trp Val
        35                  40                  45

Ser Gly Ile Ser Ala Thr Gly Gly Asn Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Gln Phe Leu Thr Trp Phe Asp Pro Trp Gly Gln Gly
            100                 105                 110

Thr Leu Val Thr Val Ser Ser
        115


<210> SEQ ID NO 45
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Phe
            20                  25                  30

Leu Ala Trp Tyr Gln Gln Lys Pro Gly Gln Pro Pro Arg Leu Leu Ile
        35                  40                  45

Tyr Asp Ala Thr Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr His Cys Gln His Arg Ser Asn Trp Pro Ser
                85                  90                  95

Ile Thr Phe Gly Gln Gly Thr Arg Leu Glu Ile Lys
            100                 105
```

<210> SEQ ID NO 46
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asn Thr
            20                  25                  30

Asn Tyr Tyr Trp Ala Trp Ile Arg Gln Pro Pro Gly Lys Gly Leu Glu
        35                  40                  45

Tyr Ile Gly Ser Ile Tyr Tyr Ser Gly Ser Thr Tyr Tyr Asn Pro Ser
    50                  55                  60

Leu Lys Ser Arg Val Thr Met Ser Val Asp Ala Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Thr His Pro Thr Leu Gly Ala Phe Val Leu Leu Trp Phe Gly
            100                 105                 110

Ala Asn Phe Asp His Trp Gly Gln Gly Thr Leu Val Thr Val Ser Ser
        115                 120                 125

<210> SEQ ID NO 47
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 47

Gln Ala Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asn
            20                  25                  30

Tyr Asp Val His Trp Tyr Gln Gln Leu Pro Gly Thr Ala Pro Lys Leu
        35                  40                  45

Leu Met Tyr Ser Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Asn Ser Trp Val Phe Gly Gly Gly Thr Gln Leu Thr Val Leu
            100                 105                 110

<210> SEQ ID NO 48
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 48

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
35 40 45

Trp Ile Gly Ser Val Tyr Tyr Ser Gly Gly Ala Ser Tyr Asn Pro Ser
50 55 60

Leu Lys Ser Arg Ala Thr Ile Ser Val Asp Thr Ser Lys Asn Gln Phe
65 70 75 80

Ser Leu Asn Leu Asp Ser Val Ser Ala Ala Asp Thr Ala Ile Tyr Tyr
85 90 95

Cys Ala Ser Ile Tyr Gly Ser Gly Thr Phe Tyr Tyr Tyr Phe Tyr Met
100 105 110

Asp Val Trp Gly Lys Gly Ser Thr Val Thr Val Ser Ser
115 120 125

<210> SEQ ID NO 49
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 49

Asp Ile Gln Met Thr Gln Ser Pro Ser Ser Leu Ser Ala Ser Val Gly
1 5 10 15

Asp Arg Val Thr Ile Thr Cys Gln Ala Ser Gln Val Ile Ser Asn Tyr
20 25 30

Leu Asn Trp Tyr Gln Gln Lys Pro Gly Lys Ala Pro Lys Leu Leu Ile
35 40 45

Tyr Asp Thr Ser Asn Leu Lys Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Glu Asn Leu Gln Phe
85 90 95

Thr Phe Gly Pro Gly Thr Lys Val Asp Ile Lys
100 105

<210> SEQ ID NO 50
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 50

Gln Val Gln Leu Val Gln Ser Gly Ala Glu Val Lys Lys Pro Gly Ala
1 5 10 15

Ser Val Lys Val Ser Cys Lys Ala Ser Gly His Thr Phe Thr Thr Tyr
20 25 30

Ala Ile His Trp Val Arg Gln Ala Pro Gly Gln Gly Leu Glu Trp Met
35 40 45

Gly Trp Ile Asn Pro Asp Asn Asp Asn Thr Glu Tyr Ser Gln Lys Phe
50 55 60

Gln Gly Arg Val Thr Ile Thr Arg Asp Thr Ser Ala Ser Thr Ala Tyr
65 70 75 80

Met Glu Leu Ser Ser Leu Ile Ser Glu Asp Thr Ala Val Phe Tyr Cys
85 90 95

Ala Ser Ala Ser Tyr Thr Phe Trp Ser Gly Tyr Tyr Ser Gly Leu Asp

```
            100                 105                 110

Tyr Trp Gly Gln Gly Thr Leu Val Thr Val Ser Ser
        115                 120


<210> SEQ ID NO 51
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Pro Gly Thr Lys Val Asp Ile Lys
            100                 105


<210> SEQ ID NO 52
<211> LENGTH: 126
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (87)..(87)
<223> OTHER INFORMATION: Xaa can be any naturally occurring amino acid

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Ile Ser Trp Val Arg Gln Ala Pro Gly Gln Gly Leu Glu Trp Met
        35                  40                  45

Gly Trp Val Asn Thr Tyr Asn Gly Asn Thr Tyr Tyr Ala Gln Ser Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Xaa Ser Asp Asp Thr Ala Val Tyr Phe Cys
                85                  90                  95

Ala Arg Asp His Pro Ile Thr Ile Phe Gly Val Ile Ile Leu Gly Glu
            100                 105                 110

Pro Thr Thr Trp Gly Gln Gly Thr Leu Val Thr Val Ser Ser
        115                 120                 125


<210> SEQ ID NO 53
<211> LENGTH: 107
<212> TYPE: PRT
<213> ORGANISM: Artificial sequence
```

<220> FEATURE:
<223> OTHER INFORMATION: Synthetic polypeptide

<400> SEQUENCE: 53

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Glu Val Tyr Tyr Cys Gln Gln Tyr Asn Asn Trp Pro Arg
                85                  90                  95

Thr Phe Gly Gln Gly Thr Lys Val Asp Ile Lys
            100                 105
```

<210> SEQ ID NO 54
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 54

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Asn Thr Asn Tyr Asn Pro Ser Leu Lys Ser
    50                  55                  60

Arg Val Thr Ile Ser Val Asp Thr Ser Lys Asn Gln Phe Ser Leu Arg
65                  70                  75                  80

Leu Ser Ser Val Thr Ala Ala Asp Thr Ala Val Tyr Tyr Cys Ala Arg
                85                  90                  95

Ser Pro Leu Phe Trp Phe Gly Glu Phe Phe Ser Ser Pro Asp His Phe
            100                 105                 110

Asp Phe Trp Gly Gln Gly Thr Leu
        115                 120
```

<210> SEQ ID NO 55
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 55

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asp Leu Val Ser Trp Tyr Gln Gln His Pro Gly Lys Ala Pro Lys Leu
        35                  40                  45
```

Met Leu Tyr Glu Gly Thr Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Gly
85 90 95

Ser Thr Leu Val Phe Gly Gly Gly Thr Gln Val Thr Val Leu
100 105 110

<210> SEQ ID NO 56
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 56

Gln Val Gln Leu Gln Glu Ser Gly Pro Gly Leu Val Lys Pro Ser Glu
1 5 10 15

Thr Leu Ser Leu Thr Cys Thr Val Ser Gly Asp Ser Ile Ser Arg Tyr
20 25 30

Tyr Trp Ser Trp Ile Arg Gln Pro Pro Gly Lys Gly Leu Glu Trp Ile
35 40 45

Gly Tyr Leu Tyr Tyr Ser Gly Ser Thr Asp Tyr Asn Pro Ser Leu Lys
50 55 60

Ser Arg Val Thr Ile Ser Val Asp Thr Ser Lys Asn Gln Phe Ser Leu
65 70 75 80

Asn Leu Thr Ser Val Thr Ala Ala Asp Thr Ala Val Tyr Tyr Cys Ala
85 90 95

Arg Gly Ser Ser Arg Gly Ile Gly Val Val Ser His Trp Phe Asp Pro
100 105 110

Trp Gly Gln Gly Thr
115

<210> SEQ ID NO 57
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 57

Ser Tyr Val Leu Thr Gln Pro Pro Ser Val Ser Val Ala Pro Gly Gln
1 5 10 15

Thr Ala Arg Ile Thr Cys Gly Gly Ser Asn Met Gly Tyr Lys Ser Val
20 25 30

Gln Trp Tyr Gln Gln Arg Pro Gly Gln Ala Pro Val Leu Val Val Tyr
35 40 45

Asp Asp Thr Asp Arg Pro Ser Gly Ile Pro Glu Arg Phe Ser Gly Ser
50 55 60

Asn Ser Gly Ala Thr Ala Thr Leu Thr Ile Ser Ser Val Glu Ala Gly
65 70 75 80

Asp Glu Ala Asp Tyr Tyr Cys Gln Val Trp Asp Ser Ser Ser Asp His
85 90 95

His Val Val Phe Gly Gly Gly Thr Gln Val Thr Val Leu
100 105

<210> SEQ ID NO 58

<211> LENGTH: 123
<212> TYPE: PRT
<213> ORGANISM: Artificial sequence
<220> FEATURE:
<223> OTHER INFORMATION: Synthetic polypeptide

<400> SEQUENCE: 58

```
Gln Val Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr His Ser Gly Ser Pro Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Met Tyr Tyr Cys Ala
                85                  90                  95

Arg Thr Ala Tyr Thr Val Gly Phe Phe Ala Tyr Tyr Tyr Leu Asp Val
            100                 105                 110

Trp Gly Arg Gly Thr Thr Leu Ser Leu Ser Cys
        115                 120
```

<210> SEQ ID NO 59
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ala Gly Ser Gly Thr Asp Phe Thr Phe Thr Ile Ser Ser Leu Gln Pro
65                  70                  75                  80

Glu Asp Val Ala Thr Tyr Tyr Cys Gln Val Tyr Asp Asn Leu Leu Phe
                85                  90                  95

Thr Ser
```

<210> SEQ ID NO 60
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 60

```
Gln Leu Gln Leu Gln Glu Ser Gly Pro Gly Leu Val Lys Pro Ser Glu
1               5                   10                  15

Thr Leu Ser Leu Ser Cys Thr Val Ser Gly Val Ser Ile Ser Asp Asn
            20                  25                  30

Ser Tyr Tyr Trp Gly Trp Ile Arg Gln Pro Pro Gly Lys Gly Leu Glu
```

```
        35                  40                  45

Trp Ile Gly Thr Ile Ser Tyr Ser Gly Asn Thr Tyr Tyr Asn Pro Ser
    50                  55                  60

Leu Lys Ser Arg Val Ser Ile Ser Gly Asp Thr Ser Lys His Gln Leu
65                  70                  75                  80

Ser Leu Lys Val Ser Ser Val Thr Ala Ala Asp Thr Ala Val Tyr Tyr
                85                  90                  95

Cys Ala Arg Gln Arg Ile Val Ser Gly Phe Val Glu Trp Leu Ser Lys
            100                 105                 110

Phe Asp Tyr Trp Gly Gln Gly Thr Leu Val Thr Val Ser Ser
        115                 120                 125


<210> SEQ ID NO 61
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 61

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Ser Gly Pro Val Val Phe Gly Gly Gly Thr Lys Leu Thr Val Leu
            100                 105                 110


<210> SEQ ID NO 62
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 62

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ile Ser Ser Asp
            20                  25                  30

Ser Tyr Tyr Trp Asn Trp Ile Arg Gln His Pro Gly Lys Gly Leu Glu
        35                  40                  45

Trp Ile Gly Tyr Val Tyr Tyr Ser Gly Ser Thr Asn Tyr Asn Pro Ser
    50                  55                  60

Leu Lys Ser Arg Val Ile Ile Ser Leu Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Ala Asp Tyr Tyr Gly Ser Gly Ser Phe Phe Tyr Tyr Tyr
            100                 105                 110
```

His Met Asp Val Trp Gly Lys Gly
115 120

<210> SEQ ID NO 63
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 63

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Tyr Thr Trp
20 25 30

Leu Ala Trp Tyr Gln Gln Lys Pro Gly Lys Ala Pro Lys Leu Leu Ile
35 40 45

His Lys Ser Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys His Gln Tyr Tyr Val Tyr Pro Cys
85 90 95

Thr Ser Ala

<210> SEQ ID NO 64
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 64

Gln Leu Gln Leu Gln Glu Ser Gly Pro Gly Leu Val Lys Pro Ser Glu
1 5 10 15

Thr Leu Phe Leu Ser Cys Ala Val Ser Gly Gly Ser Ile Ala Gly Ser
20 25 30

Thr His Tyr Trp Gly Trp Ile Arg Gln Pro Pro Gly Lys Gly Leu Glu
35 40 45

Trp Ile Gly Ser Ile Ser Glu Ser Gly Ser Thr Tyr His Asn Pro Ser
50 55 60

Leu Lys Ser Arg Val Thr Ile Ser Val Asp Thr Ser Lys Asn Tyr Phe
65 70 75 80

Ser Leu Asn Leu Ser Ser Val Thr Ala Ala Asp Thr Ala Val Tyr Tyr
85 90 95

Cys Ala Arg Ile Val Gly Gln Ser Gly Thr Phe Ile Tyr Tyr Tyr Tyr
100 105 110

Ala Met Asp Val Trp Gly Thr Gly Thr Leu Val Thr Val Ser Ser
115 120 125

<210> SEQ ID NO 65
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 65

Asp Ile Gln Leu Thr Gln Ser Pro Ser Phe Leu Ser Ala Ser Val Gly
1 5 10 15

-continued

```
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Gln Gln Leu Asn Ser Tyr Leu Ala
                85                  90                  95

Leu Ile Phe Gly Gly Gly Thr
            100


<210> SEQ ID NO 66
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Ser Val Ser Gly Asp Ser Val Ser Ser Gly
            20                  25                  30

Asp Tyr Tyr Trp Ser Trp Leu Arg Gln Pro Pro Gly Lys Gly Leu Glu
        35                  40                  45

Trp Ile Gly Tyr Ile Tyr Tyr Ser Gly Ala Thr Asn Tyr Asn Pro Ser
    50                  55                  60

Leu Lys Ser Arg Val Thr Ile Ser Leu Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Arg Ala Gly Phe Leu Glu Trp Leu Phe Phe Glu Asp
            100                 105                 110

Trp Gly Gln Gly Thr
        115


<210> SEQ ID NO 67
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Phe Cys Arg Ala Ser Gln Ser Ile Gly Thr Tyr
            20                  25                  30

Leu Ser Trp Tyr Gln Gln Lys Pro Gly Lys Ala Pro Lys Val Leu Ile
        35                  40                  45

Tyr Ala Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
```

```
                85                  90                  95

Gly Thr Lys Val Asp Met Lys
            100


<210> SEQ ID NO 68
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 68

Gln Leu Gln Leu Gln Glu Ser Gly Pro Gly Leu Val Lys Pro Ser Glu
1               5                   10                  15

Thr Leu Ser Leu Thr Cys Thr Val Ala Gly Gly Pro Ile Thr Ser Asn
            20                  25                  30

Asn Tyr Tyr Trp Gly Trp Ile Arg Gln Ser Pro Gly Lys Gly Leu Glu
        35                  40                  45

Trp Ile Gly Ser Val Tyr Tyr Ser Gly Asn Thr Tyr Tyr Asn Pro Ser
    50                  55                  60

Ile Lys Thr Arg Val Thr Met Ser Val Asp Thr Ser Lys Ser Gln Phe
65                  70                  75                  80

Ser Leu Lys Leu Asn Ser Val Thr Ala Ala Asp Thr Ala Val Tyr Tyr
                85                  90                  95

Cys Ala Arg Gln Phe Arg Leu Leu Gln Phe Val Glu Trp Leu His His
            100                 105                 110

Phe Asp Ser Trp Gly Pro Gly Asn
        115                 120


<210> SEQ ID NO 69
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 69

Ser Tyr Val Leu Thr Gln Pro Pro Ser Val Ser Val Ala Pro Gly Gln
1               5                   10                  15

Thr Ala Arg Ile Pro Cys Gly Gly Asn Asp Ile Ala Asn Lys Arg Val
            20                  25                  30

His Trp Tyr Gln Gln Lys Pro Gly Gln Ala Pro Met Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Asn Ser Ser Asp Leu
                85                  90                  95

Cys Val Val Phe Gly Gly Gly Thr Lys Leu Thr Val Leu
            100                 105


<210> SEQ ID NO 70
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 70
```

Glu Val Gln Leu Val Glu Ser Gly Gly Gly Leu Val Lys Pro Gly Gly
1 5 10 15

Ser Leu Arg Ile Ser Cys Val Thr Ser Gly Phe Thr Phe Gly Asp Tyr
20 25 30

Ala Met Ser Trp Phe Arg Gln Ala Pro Gly Lys Gly Leu Glu Trp Val
35 40 45

Gly Phe Ile Arg Asn Lys Gly Tyr Gly Gly Thr Ile Asp Tyr Ala Ala
50 55 60

Ser Val Lys Gly Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

Tyr Cys Thr Gly Val Arg Leu His Tyr Asp Phe Trp Ser Gly Tyr Asp
100 105 110

Asp Asp Ser Phe His Ile Trp Gly Gln Gly Thr Met
115 120

<210> SEQ ID NO 71
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 71

Asp Gly Val Met Thr Gln Ser Pro Leu Ser Leu Pro Val Thr Pro Gly
1 5 10 15

Gln Pro Ala Ser Ile Ser Cys Arg Ser Thr Gln Ser Leu Val His Gly
20 25 30

Asp Gly Asp Thr Tyr Leu Tyr Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ser
85 90 95

Thr His Trp Pro Pro Thr Phe Gly Gln
100 105

<210> SEQ ID NO 72
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 72

Gln Leu Gln Leu Gln Glu Ser Gly Pro Gly Leu Val Lys Pro Ser Glu
1 5 10 15

Thr Leu Ser Leu Thr Cys Ala Val Ser Gly Gly Ser Ile Ser Ser Ser
20 25 30

Gly Tyr Cys Trp Gly Trp Ile Arg Gln Pro Pro Gly Lys Gly Leu Glu
35 40 45

Trp Ile Ala Ser Ile Cys Ser Ser Gly Thr Thr Tyr Phe Asn Ser Ser
50 55 60

Leu Lys Ser Arg Val Ser Ile Ser Ile Asp Thr Ser Arg Pro Gln Phe

```
65                  70                  75                  80

Leu Leu Asn Leu Arg Ser Leu Thr Ala Ala Asp Thr Ala Val Tyr Tyr
                85                  90                  95

Cys Ala Arg Gln Arg Met Glu Leu His Phe Leu Glu Trp Leu Phe Pro
            100                 105                 110

Phe Asp Ser Trp Gly Gln Gly Thr Leu Val Thr Val Ser Ser
        115                 120                 125


<210> SEQ ID NO 73
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 73

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Asn Trp Pro Cys
                85                  90                  95

Ser Phe Gly Gln Gly Thr Lys Val Asp Ile Lys
            100                 105


<210> SEQ ID NO 74
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Val Lys Glu Asp Gly Ser Lys Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Val Arg Gly Glu Asp Cys Ser Gly Gly Arg Cys Ser Ser Leu Phe Phe
            100                 105                 110

Pro Gln His Tyr Phe Asp Tyr Trp Gly Pro Gly Asn
        115                 120


<210> SEQ ID NO 75
<211> LENGTH: 107
```

<212> TYPE: PRT
<213> ORGANISM: Artificial sequence
<220> FEATURE:
<223> OTHER INFORMATION: Synthetic polypeptide

<400> SEQUENCE: 75

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Leu Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Val Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Ala Gly Gly Thr Lys Val Glu Ile Lys
            100                 105

<210> SEQ ID NO 76
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Gly Asn
            20                  25                  30

Phe Trp Ser Trp Ile Arg Gln Pro Pro Gly Lys Gly Leu Glu Tyr Ile
        35                  40                  45

Gly Tyr Met Ser Asp Ile Gly Thr Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Asn Leu Thr Ser Val Thr Ala Ala Asp Ala Ala Val Tyr Tyr Cys Ala
                85                  90                  95

Arg Leu Val Ala Val Pro Gly Phe Phe Tyr His Tyr Tyr Met Asp Val
            100                 105                 110

Trp Gly Glu Gly Thr Leu Val Thr Val Ser Ser
        115                 120

<210> SEQ ID NO 77
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 77

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Leu Leu Ile

```
        35                  40                  45

Tyr Ala Thr Ser Thr Leu Gln Ser Gly Val Pro Ser Arg Phe Ser Gly
    50                  55                  60

Ser Glu Ser Gly Thr Ala Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105


<210> SEQ ID NO 78
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 78

Gln Val Gln Leu Val Glu Ser Gly Gly Gly Val Val Gln Pro Gly Gly
1               5                   10                  15

Ser Leu Arg Ile Ser Cys Ala Ala Ala Gly Phe Thr Phe Ser Arg Ser
            20                  25                  30

Gly Met His Trp Val Arg Gln Ala Pro Gly Lys Gly Leu Glu Trp Val
        35                  40                  45

Ala Val Ile Ser Tyr Asp Gly Asn Thr Glu His Tyr Ala Asp Ser Met
    50                  55                  60

Glu Gly Arg Val Thr Val Ser Arg Asp Asn Ser Asn Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Asp Arg His Thr Thr Gly Ser Asn Tyr Asn Gly Gly Leu Leu
            100                 105                 110

Asp His Trp Gly Gln Gly Thr Leu Val Thr Val Ser Ser
        115                 120                 125


<210> SEQ ID NO 79
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 79

Glu Thr Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30

Ser Lys Asn Arg Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Tyr Thr Ser Pro Leu Thr Phe Gly Gln Gly Thr Arg Leu Glu Ile
            100                 105                 110
```

Lys

<210> SEQ ID NO 80
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 80

Gly Phe Thr Phe Ser Ser Tyr Ala
1               5

<210> SEQ ID NO 81
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 81

Ile Ser Ala Thr Gly Gly Asn Thr
1               5

<210> SEQ ID NO 82
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 82

Ala Arg Pro Leu Gln Phe Leu Thr Trp Phe Asp Pro
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 83

Gly Asp Ser Ile Asn Asn Thr Asn Tyr Tyr
1               5                   10

<210> SEQ ID NO 84
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 84

Ile Tyr Tyr Ser Gly Ser Thr
1               5

<210> SEQ ID NO 85
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 85

Ala Thr His Pro Thr Leu Gly Ala Phe Val Leu Leu Trp Phe Gly Ala
1               5                   10                  15

Asn Phe Asp His
20

<210> SEQ ID NO 86
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 86

Gly Gly Ser Ile Ser Ser Ser Ser Tyr Tyr
1 5 10

<210> SEQ ID NO 87
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 87

Val Tyr Tyr Ser Gly Gly Ala
1 5

<210> SEQ ID NO 88
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 88

Ala Ser Ile Tyr Gly Ser Gly Thr Phe Tyr Tyr Tyr Phe Tyr Met Asp
1 5 10 15

Val

<210> SEQ ID NO 89
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 89

Gly His Thr Phe Thr Thr Tyr Ala
1 5

<210> SEQ ID NO 90
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 90

Ile Asn Pro Asp Asn Asp Asn Thr
1 5

<210> SEQ ID NO 91
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 91

Ala Ser Ala Ser Tyr Thr Phe Trp Ser Gly Tyr Tyr Ser Gly Leu Asp
1 5 10 15

Tyr

<210> SEQ ID NO 92
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 92

Gly Tyr Thr Phe Ser Asn Tyr Gly
1 5

<210> SEQ ID NO 93
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 93

Val Asn Thr Tyr Asn Gly Asn Thr
1 5

<210> SEQ ID NO 94
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 94

Ala Arg Asp His Pro Ile Thr Ile Phe Gly Val Ile Ile Leu Gly Glu
1 5 10 15

Pro Thr Thr

<210> SEQ ID NO 95
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 95

Gly Asp Ser Ile Asn Asn Tyr Tyr
1 5

<210> SEQ ID NO 96
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 96

Ile Tyr Tyr Ser Asn Thr
1 5

<210> SEQ ID NO 97
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 97

Ala Arg Ser Pro Leu Phe Trp Phe Gly Glu Phe Phe Ser Ser Pro Asp
1               5                   10                  15

His Phe Asp Phe
            20

<210> SEQ ID NO 98
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 98

Gly Asp Ser Ile Ser Arg Tyr Tyr
1               5

<210> SEQ ID NO 99
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 99

Leu Tyr Tyr Ser Gly Ser Thr
1               5

<210> SEQ ID NO 100
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 100

Ala Arg Gly Ser Ser Arg Gly Ile Gly Val Val Ser His Trp Phe Asp
1               5                   10                  15

Pro

<210> SEQ ID NO 101
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 101

Gly Gly Ser Ile Ser Gly Tyr Tyr
1               5

<210> SEQ ID NO 102
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 102

Ile Tyr His Ser Gly Ser Pro
1               5

<210> SEQ ID NO 103
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 103

Ala Arg Thr Ala Tyr Thr Val Gly Phe Phe Ala Tyr Tyr Tyr Leu Asp
1 5 10 15

Val

<210> SEQ ID NO 104
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 104

Gly Val Ser Ile Ser Asp Asn Ser Tyr Tyr
1 5 10

<210> SEQ ID NO 105
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 105

Ile Ser Tyr Ser Gly Asn Thr
1 5

<210> SEQ ID NO 106
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 106

Ala Arg Gln Arg Ile Val Ser Gly Phe Val Glu Trp Leu Ser Lys Phe
1 5 10 15

Asp Tyr

<210> SEQ ID NO 107
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 107

Gly Gly Ser Ile Ser Ser Asp Ser Tyr Tyr
1 5 10

<210> SEQ ID NO 108
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 108

Val Tyr Tyr Ser Gly Ser Thr

-continued 1 5

<210> SEQ ID NO 109
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 109

Ala Arg Ala Asp Tyr Tyr Gly Ser Gly Ser Phe Phe Tyr Tyr Tyr His
1 5 10 15

Met Asp Val

<210> SEQ ID NO 110
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 110

Gly Gly Ser Ile Ala Gly Ser Thr His Tyr
1 5 10

<210> SEQ ID NO 111
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 111

Ile Ser Glu Ser Gly Ser Thr
1 5

<210> SEQ ID NO 112
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 112

Ala Arg Ile Val Gly Gln Ser Gly Thr Phe Ile Tyr Tyr Tyr Tyr Ala
1 5 10 15

Met Asp Val

<210> SEQ ID NO 113
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 113

Gly Asp Ser Val Ser Ser Gly Asp Tyr Tyr
1 5 10

<210> SEQ ID NO 114
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 114

Ile Tyr Tyr Ser Gly Ala Thr
1 5

<210> SEQ ID NO 115
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 115

Ala Arg Glu Arg Ala Gly Phe Leu Glu Trp Leu Phe Phe Glu Asp
1 5 10 15

<210> SEQ ID NO 116
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 116

Gly Gly Pro Ile Thr Ser Asn Asn Tyr Tyr
1 5 10

<210> SEQ ID NO 117
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 117

Val Tyr Tyr Ser Gly Asn Thr
1 5

<210> SEQ ID NO 118
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 118

Ala Arg Gln Phe Arg Leu Leu Gln Phe Val Glu Trp Leu His His Phe
1 5 10 15

Asp Ser

<210> SEQ ID NO 119
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 119

Gly Phe Thr Phe Gly Asp Tyr Ala
1 5

<210> SEQ ID NO 120
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 120

Ile Arg Asn Lys Gly Tyr Gly Gly Thr Ile
1               5                   10

<210> SEQ ID NO 121
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 121

Thr Gly Val Arg Leu His Tyr Asp Phe Trp Ser Gly Tyr Asp Asp Asp
1               5                   10                  15

Ser Phe His Ile
            20

<210> SEQ ID NO 122
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 122

Gly Gly Ser Ile Ser Ser Ser Gly Tyr Cys
1               5                   10

<210> SEQ ID NO 123
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 123

Ile Cys Ser Ser Gly Thr Thr
1               5

<210> SEQ ID NO 124
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 124

Ala Arg Gln Arg Met Glu Leu His Phe Leu Glu Trp Leu Phe Pro Phe
1               5                   10                  15

Asp Ser

<210> SEQ ID NO 125
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 125

Gly Phe Thr Phe Ser Ser Tyr Trp
1               5

<210> SEQ ID NO 126
<211> LENGTH: 8

<212> TYPE: PRT
<213> ORGANISM: Artificial sequence
<220> FEATURE:
<223> OTHER INFORMATION: Synthetic polypeptide

<400> SEQUENCE: 126

Val Lys Glu Asp Gly Ser Lys Lys
1 5

<210> SEQ ID NO 127
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 127

Val Arg Gly Glu Asp Cys Ser Gly Gly Arg Cys Ser Ser Leu Phe Phe
1 5 10 15

Pro Gln His Tyr Phe Asp Tyr
20

<210> SEQ ID NO 128
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 128

Gly Ala Ser Ile Ser Gly Asn Phe
1 5

<210> SEQ ID NO 129
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 129

Met Ser Asp Ile Gly Thr Thr
1 5

<210> SEQ ID NO 130
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 130

Ala Arg Leu Val Ala Val Pro Gly Phe Phe Tyr His Tyr Tyr Met Asp
1 5 10 15

Val

<210> SEQ ID NO 131
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 131

Gly Phe Thr Phe Ser Arg Ser Gly
1 5

<210> SEQ ID NO 132
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 132

Ile Ser Tyr Asp Gly Asn Thr Glu
1               5

<210> SEQ ID NO 133
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 133

Ala Lys Asp Arg His Thr Thr Gly Ser Asn Tyr Asn Gly Gly Leu Leu
1               5                   10                  15

Asp His

<210> SEQ ID NO 134
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 134

Gln Ser Val Asn Asn Phe
1               5

<210> SEQ ID NO 135
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 135

Gln His Arg Ser Asn Trp Pro Ser Ile Thr
1               5                   10

<210> SEQ ID NO 136
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 136

Ser Ser Asn Ile Gly Ala Asn Tyr Asp
1               5

<210> SEQ ID NO 137
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 137

Gln Ser Tyr Asp Asn Ser Leu Asn Ser Trp Val 1 5 10

<210> SEQ ID NO 138
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 138

Gln Val Ile Ser Asn Tyr
1 5

<210> SEQ ID NO 139
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 139

Gln Gln Tyr Glu Asn Leu Gln Phe Thr
1 5

<210> SEQ ID NO 140
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 140

Gln Ser Val Ser Ile Asn Tyr
1 5

<210> SEQ ID NO 141
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 141

Gln Gln Tyr Gly Ser Ser Pro Pro Trp Thr
1 5 10

<210> SEQ ID NO 142
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 142

Gln Ser Val Asn Ser Asn
1 5

<210> SEQ ID NO 143
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 143

Gln Gln Tyr Asn Asn Trp Pro Arg Thr
1 5

<210> SEQ ID NO 144
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 144

Ser Ser Asp Val Gly Ser Tyr Asp Leu
1 5

<210> SEQ ID NO 145
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 145

Cys Ser Tyr Ala Gly Gly Ser Thr Leu Val
1 5 10

<210> SEQ ID NO 146
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 146

Asn Met Gly Tyr Lys Ser
1 5

<210> SEQ ID NO 147
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 147

Gln Val Trp Asp Ser Ser Ser Asp His His Val Val
1 5 10

<210> SEQ ID NO 148
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 148

His Asp Ile Ser Asn Tyr
1 5

<210> SEQ ID NO 149
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 149

Gln Val Tyr Asp Asn Leu Leu Phe Thr
1 5

<210> SEQ ID NO 150
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 150

Ser Ser Asn Ile Gly Ala Gly Phe Asp
1               5

<210> SEQ ID NO 151
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 151

Gln Ser Tyr Asp Thr Ser Leu Ser Gly Pro Val Val
1               5                   10

<210> SEQ ID NO 152
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 152

Gln Ser Ile Tyr Thr Trp
1               5

<210> SEQ ID NO 153
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 153

His Gln Tyr Tyr Val Tyr Pro Cys Thr
1               5

<210> SEQ ID NO 154
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 154

Gln Gly Ile Ser Ser Tyr
1               5

<210> SEQ ID NO 155
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 155

Gln Gln Leu Asn Ser Tyr Leu Ala Leu Ile
1               5                   10

<210> SEQ ID NO 156
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 156

Gln Ser Ile Gly Thr Tyr
1               5

<210> SEQ ID NO 157
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 157

Gln Gln Ser Arg Thr
1               5

<210> SEQ ID NO 158
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 158

Asp Ile Ala Asn Lys Arg
1               5

<210> SEQ ID NO 159
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 159

Gln Val Trp Glu Asn Ser Ser Asp Leu Cys Val Val
1               5                   10

<210> SEQ ID NO 160
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 160

Gln Ser Leu Val His Gly Asp Gly Asp Thr Tyr
1               5                   10

<210> SEQ ID NO 161
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 161

Met Gln Ser Thr His Trp Pro Pro Thr
1               5

<210> SEQ ID NO 162

<211> LENGTH: 6
<212> TYPE: PRT
<213> ORGANISM: Artificial sequence
<220> FEATURE:
<223> OTHER INFORMATION: Synthetic polypeptide

<400> SEQUENCE: 162

Gln Ser Val Ser Ser Asn
1               5

<210> SEQ ID NO 163
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 163

Gln Gln Tyr Ile Asn Trp Pro Cys Ser
1               5

<210> SEQ ID NO 164
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 164

Gln Gly Ile Leu Asn Trp
1               5

<210> SEQ ID NO 165
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 165

Gln Gln Thr Asn Ser Phe Pro Leu Thr
1               5

<210> SEQ ID NO 166
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 166

Gln Gly Ile Ser Gly Trp
1               5

<210> SEQ ID NO 167
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 167

Gln Gln Ala Asn Ser Phe Pro Leu Thr
1               5

<210> SEQ ID NO 168
<211> LENGTH: 12

-continued

<212> TYPE: PRT
<213> ORGANISM: Artificial sequence
<220> FEATURE:
<223> OTHER INFORMATION: Synthetic polypeptide

<400> SEQUENCE: 168

Gln Ser Val Leu His Ser Ser Lys Asn Arg Asn Tyr
1 5 10

<210> SEQ ID NO 169
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 169

Gln Gln Tyr Tyr Thr Ser Pro Leu Thr
1 5